US009851332B2

(12) United States Patent
Yusuf et al.

(10) Patent No.: US 9,851,332 B2
(45) Date of Patent: Dec. 26, 2017

(54) PROCESS FOR DETERMINING WELD QUALITY USING FLEXURAL CHARACTERISTICS

(71) Applicant: King Fahd University of Petroleum and Minerals, Dhahran (SA)

(72) Inventors: Adesina Akeem Yusuf, Dhahran (SA); Iyad T. Alzaharnah, Dhahran (SA); Bekir S. Yilbas, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 290 days.

(21) Appl. No.: 14/841,903

(22) Filed: Sep. 1, 2015

(65) Prior Publication Data
US 2016/0084802 A1    Mar. 24, 2016

Related U.S. Application Data

(60) Provisional application No. 62/052,983, filed on Sep. 19, 2014.

(51) Int. Cl.
*G01N 29/12* (2006.01)
*G01N 29/44* (2006.01)
*G01N 29/04* (2006.01)
*G01N 29/30* (2006.01)

(52) U.S. Cl.
CPC .......... *G01N 29/12* (2013.01); *G01N 29/045* (2013.01); *G01N 29/30* (2013.01); *G01N 29/4436* (2013.01); *G01N 2291/02827* (2013.01); *G01N 2291/2675* (2013.01)

(58) Field of Classification Search
CPC ...... G01N 29/12; G01N 29/045; G01N 29/30; G01N 29/4436; G01N 2291/02827; G01N 2291/2675

USPC .......................................................... 73/582
See application file for complete search history.

(56) References Cited

U.S. PATENT DOCUMENTS 4,007,631 A * 2/1977 Saifi ...................... G01N 29/14
                                                219/121.64
2002/0144984 A1* 10/2002 Mori ...................... B23K 26/03
                                                219/121.64

FOREIGN PATENT DOCUMENTS

| CN | 103995051 B | * | 8/2014 |
| JP | 3-243285 A | | 10/1991 |
| JP | 2004-122205 A | | 4/2004 |
| JP | 2004122205 A | * | 4/2004 |
| JP | 4619092 B2 | | 1/2011 |

(Continued)

OTHER PUBLICATIONS

Translation JP 2004122205 Japanese application # JP20020292414.*

(Continued)

*Primary Examiner* — Natalie Huls
*Assistant Examiner* — Monica S Young
(74) *Attorney, Agent, or Firm* — Oblon, McClelland, Maier & Neustadt, L.L.P.

(57) ABSTRACT

A process for determining the quality of a laser weld-seam, whereby a welded plate and a geometrically equivalent non-welded plate are subjected to a physical impact to generate a natural vibration frequency. The natural vibration frequency of the welded plate and the non-welded plate is then measured with an accelerometer and compared. The uniformity of the weld is then determined by the similarity between the natural vibration frequency of the welded plate and the geometrically equivalent non-welded plate.

18 Claims, 111 Drawing Sheets

(56) References Cited

FOREIGN PATENT DOCUMENTS

| JP | 4873854 B2 | 2/2012 |
|----|------------|--------|
| JP | 2014-155929 A | 8/2014 |
| WO | WO 2008/026299 A1 | 3/2008 |

OTHER PUBLICATIONS iitg.vlab.co.in,. (2011). Free Vibration of a Cantilever Beam (Continuous System). Retrieved Aug. 10, 2017, from iitg.vlab.co.in/?sub=62&brch=175&sim=1080&cnt=1.*
Translation CN 103995051 B.*

* cited by examiner absorption spontaneous emission stimulated emissoin

PROCESS FOR DETERMINING WELD QUALITY USING FLEXURAL CHARACTERISTICS

CROSS REFERENCE TO RELATED APPLICATIONS

This application claims the benefit of U.S. Provisional Application No. 62/052,983 filed Sep. 19, 2014.

BACKGROUND OF THE INVENTION

Technical Field

The present invention relates to a process for determining weld quality using flexural characteristics, whereby a welded plate and a geometrically equivalent non-welded plate are subjected to a physical impact to generate a natural vibration frequency, which is measured and compared.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

BACKGROUND

Laser welding applications have increased over the past two decades, due to advantages including noncontact welding process with minimal thermal distortion, high precision and relatively high welding speed/high energy density. Laser welding has been adopted in automobile, aircraft, marine, aerospace and medical device manufacturing industries in lieu of other welding techniques due to fine grain structure/excellent weld quality, low costs and increased productivity. Material versatility of laser welding is another advantage that has made the process more acceptable to the industries. Low carbon steels are considered a good candidate for laser welding processes because high carbon content can lead to solidification cracking. The 316L stainless steel is an extra-low carbon version of grade 316, it minimizes harmful carbide precipitation due to welding. Due to this property (low carbon: 0.03% max) amongst other austenitic stainless steels, 316L steel has become an important material both to researchers and manufacturers.

Laser Welding

Laser welding is a high energy-density, low heat input process with specific advantages over the conventional fusion welding process. In some applications, laser welding is commonly replacing metal inert gas (MIG), metal active gas (MAG) and resistance spot weld processes, "See A. Ribolla, G. L. Damoulis, and G. F. Batalha, "The use of Nd: YAG laser weld for large scale volume assembly of automotive body in white," *Journal of materials processing technology*, vol. 164, pp. 1120-1127, 2005; and "See X. B. Liu, G. Yu, J. Guo, Y. J. Gu, M. Pang, C. Y. Zheng, and H. H. Wang, "Research on laser welding of cast Ni-based superalloy K418 turbo disk and alloy steel 42CrMo shaft," *Journal of Alloys and Compounds*, vol. 453, pp. 371-378, 2008 (reference), each incorporated herein by reference in their entirety."

Principle of Laser Generation

Laser generation is the result of energy emission this is associated with the transition of an electron from a higher to a lower energy level or orbit within an atom "See E. Kannatey-Asibu Jr, *Principles of laser materials processing* vol. 4: Wiley, 2009 (reference), incorporated herein by reference in its entirety."

The generation of a laser beam is essentially a three step process that occurs almost instantaneously as follows (FIG. 1):

When an atom is irradiated with photons, the electrons are excited or stimulated to a higher energy level by absorbing the energy of the incident photons. This process is referred to as absorption or stimulated absorption. The energy absorption rate depends proportionally on the number of atoms at the lower energy level and the energy density of the incident photons. Due to the excitation of electrons to higher energy levels, the atom becomes unstable and seeks to return to the ground state, thereby emitting some of its energy as photons. The emission process can occur in two ways, either by spontaneous and/or stimulated emission.

The spontaneous emission happens when the transition from a higher energy level to a lower energy level occurs naturally without being stimulated by incident radiation. If the atom is fully stable in its excited state, then no spontaneous emission will occur. If the atom in its excited state is irradiated again with photons, the photons will stimulate the atom to undergo a transition to the lower energy level, called stimulated emission. The energy release due to this transition in the form of photons is the same as the incident stimulating photons, thus strengthening the emitted photons. This results in stimulated emission, where the incident and emitted photons have the same characteristics, are in phase, resulting in a high degree of coherence, and the direction, frequency, and state of polarization of the emitted photons are essentially the same as those of the incident photons. The two photons can generate an avalanche of photons within the atom by repetitive occurrence of the stimulated emission also referred to as amplification by stimulated emission as illustrated in FIG. 2 "See M. Griot, "Basic Laser Principles," in *Introduction to Laser Technology*, 36. vol. 36: Melles Griot, pp. 2-32 (reference), incorporated herein by reference in its entirety."

Laser Welding Types

Laser welding is a process that melts and joins metals by heating them with a laser beam. The laser beam is produced using a gas mix of $CO_2$, $N_2$ and He, which is continually excited by electrodes, to produce a collimated photon beam "See J. Kell, J. R. Tyrer, R. L. Higginson, and R. C. Thomson, "Microstructural characterization of autogenous laser welds on 316L stainless steel using EBSD and EDS," *Journal of microscopy*, vol. 217, pp. 167-173, 2005 (reference), incorporated herein by reference in its entirety." Laser welding became heavily used in various industries due to its various advantages ranging from higher speed/precision, welding of complex joint geometry, low heat application, less microstructural alterations, low thermal distortion, and relatively cavity-free welds.

The often used lasers for welding are the $CO_2$ and neodymium:yttrium-aluminum-garnet (Nd:YAG) Lasers. $CO_2$ lasers are conventionally used for continuous welds because high power continuous wave (CW) beams can be achieved. Nd:YAG have been historically used for spot welding of small components like medical instruments, razor blades etc. "See C. Joachim Berkmanns and U. Mark Faerber, "Facts About Laser Technology," in 43490816 0105—1.1 *BBDO*. vol. http://www.linde-gas.com: Linde Gas (reference), incorporated herein by reference in its entirety."

Material Selection Consideration

Lasers can weld a wide range of materials, but some materials are more suitable for laser welding. The material properties important for laser welding are a) material reflectivity, b) the effect of the high thermal cycling and c) the vaporization of volatile alloying elements. The most widely laser welded material is steel, specifically steel with a carbon content below 0.12% "See U. Miyachi, "Nd:YAG Laser Welding Guide," Unitek Miyachi Corporation (http://www.unitekmiyachi.com), 2003 (reference), incorporated herein by reference in its entirety." Materials with a carbon content above 0.25% may require heat treatment before welding to avoid the formation of brittle microstructures.

Laser Welding Parameters

The major parameters that affect laser welding process include the laser power, the traverse velocity, the shielding gas, the joint type, the beam characteristics and the focusing distance, which is the distance between specimen and the optical focal points. It was reported that the penetration depth increases with increasing laser power (FIG. 3). Laser power has less influence on both weld profile and the heat affected zone (HAZ) width in comparison with its effect on penetration depth "See A. M. El-Batahgy, "Effect of laser welding parameters on fusion zone shape and solidification structure of austenitic stainless steels," *Materials Letters*, vol. 32, pp. 155-163, 1997 (reference), incorporated herein by reference in its entirety." The welding speed plays a significant role in the size and shape of the fusion zone. An increase in the welding speed will lead to an increase in the weld-depth to width ratio which means a decrease in the fusion zone size. The welding (shielding) gas often plays an active role in the welding process, such as increasing the welding speed and improving the mechanical properties of the joint.

Mechanism of Laser Welding

When the laser beam is irradiated on a workpiece surface, a significant percentage of the beam energy is reflected away from the surface, while the remaining percentage is absorbed by the surface. The absorbed energy heats up the surface thereby increasing its temperature. With the raise in temperature, the surface absorptivity increases which increases the temperature further. A level is reached where melting and possible evaporation of the metal are localized which creates a vapor cavity within the metal. Hence, laser welding can be of two types based on the mechanism:

a. The conduction mode (Conduction Limited) welding
b. The keyhole (Deep Penetration) welding The conduction mode is usually employed for welding foils and thin sheets, while keyhole mode welding is used for relatively thick workpiece.

a. The Conduction Mode Welding

This mode of laser welding occurs at a low power density (less than $10^6$ W/cm$^2$) with minimal workpiece vaporization. The laser beam is first focused on the surface and then transferred to the surroundings by conduction, forming a nugget that is shallow and has a wider heat-affected zone compared to keyhole welding. FIG. 4 illustrates a conduction mode welding. The shape of the weld pool in conduction mode welding is primarily determined by the flow in the weld pool and surface active elements.

b. Keyhole Mode Welding

Keyhole mode welding is characterized by deep narrow welds. A high power density of above $10^6$ W/cm$^2$, the workpiece material is vaporized to form a cavity (the keyhole), which is surrounded by molten metal, which in turn is surrounded by the solid material. The molten material fills the cavity which contains vapor, plasma (or both) as the laser beam progresses along the joint "See M. Sokolov, A. Salminen, V. Somonov, and A. F. H. Kaplan, "Laser welding of structural steels: Influence of the edge roughness level," *Optics & Laser Technology* (reference); and See N. S. Shanmugam, Buvanashekaran, G., Sankaranarayanasamy, K., "Experimental investigation and finite element simulation of laser beam welding of AISI 304 stainless steel sheet," *Experimental Techniques*, vol. 34, pp. 25-36, 2010 (reference), each incorporated herein by reference in their entirety."

About 70-90% of the laser energy formed at the keyhole is transferred deeper into the material, which results in absorption and very narrow and deep penetration welds to be achieved. The high energy in laser welding coupled with minimal distortion makes laser keyhole welding useful for machined component and aerospace engine components. The keyhole shape is best represented with a vertical cylinder which is generally bent in the direction of the workpiece travel as shown in FIG. 5.

Microstructural Defects in Laser Welding

Despite the aforementioned merits of laser welding, it may also cause undesirable defects that reduce the mechanical properties of the material and hence affect the reliability and performance of the material. The defects include coring or macro-segregation, solidification cracking, and porosity:

a. Coring or Macro-segregation: In laser processing, the high cooling rates make achieving equilibrium during diffusion difficult. Hence there is a composition gradient formed across the solid. The variation in the composition across the solid is a result of the segregation of impurities and alloying elements during the solidification process, which consequently causes variation in the material properties across the fusion. Therefore, a region within the fusion zone will have poor microstructural composition thereby adversely affecting the region's mechanical properties.

b. Porosity: In laser processing, voids (or cavities) may be formed due to entrapment of gas during solidification processes. It is formed by the absorption of gases into the melt and their subsequent escape during solidification as a result of limited solubility of the gas in the solid. Surface contamination such as oils, moisture and paints, and chemical reactions are major sources of gases in the molten metal.

c. Cracking: Cracking is caused by the residual stresses resulting from the fusion zone contracting during cooling. If the crack occurs just after the solidification process in the temperature range of about 200-300° C. below the melting temperature, it is referred to as hot cracking. Cold cracking occurs when the bead has cooled down to room temperature (FIG. 6A-B). Other forms of cracking that may occur include liquid cracking, lamellar cracking and reheat cracking. Cracks are the most devastating of all defects and also difficult to detect "See A. P. Kyriakongonas, "3D Numerical Modeling of Austenitic Stainless Steel 316L Multi-pass Butt Welding and Comparison with Experimental Results," in *Mechanical Engineering*: Marine Science and Technology (reference), incorporated herein by reference in its entirety."

Natural Frequency

Recently, modal analysis has become a widespread means of finding the modes of vibration and the natural frequency of a structure for evaluating the structure's integrity. Structural dynamics testing on product prototypes is used to assess the real dynamic behavior. From the many nondestructive test now available, dynamic methods have grown in importance when compared to conventional diagnostic methods, like that based on visual inspection or ultrasonic analysis "See Z. I. Praisach, G. R. Gillbert, and D. E. Birdeanu, "Considerations on natural frequency changes in damaged cantilever beams using FEM," in *Proceedings of the 3rd WSEAS International Conference on Engineering Mechanics, Structures, Engineering Geology (EMESEG '10)*, Corfu Island, Greece (reference), incorporated herein by reference in its entirety." Many researchers have employed dynamic Non-Destructive Testing (NDT) to investigate the viability of a structure system. The shift in the position of the natural frequency has been the key factor for evaluating the viability of structures. The presence of defects developed in a component changes its flexural characteristics, e.g. a reduction in the stiffness, increase in the damping and a reduction in the natural frequency "See A. A. V. Deokar and B. V. D. Wakchaure, "Experimental Investigation of Crack Detection in Cantilever Beam Using Natural Frequency as Basic Criterion," *International Conference on Current Trend in technology NUiCONE*, 2011 (reference), incorporated herein by reference in its entirety." This change in the natural frequency results from the changes in material properties of the structure during welding. During an experiment on the vibration of welded steel boxes it was noticed that there were frequency changes of up to 20% for certain modes of a particular box when tested in the "as welded" condition and after stress relieving "See M. M. Kaldas and S. M. Dickinson, "The flexural vibration of welded rectangular plates," *Journal of Sound and Vibration*, vol. 75, pp. 163-178, 1981 (reference); and "See S. M. DICKINSON, "Flexural vibration of rectangular plate systems.," in *Mechanical Engineering* Nottingham: The University of Nottingham., 2006 (reference), each incorporated herein by reference in their entirety."

The flexural motion of the system involves the to and fro oscillation between potential and kinetic energy. The system may also be subjected to damping, wherein the system loses energy, free vibration decreases and the system eventually comes to rest. However the forced vibration can remain at the exciting frequency with supplied energy. The damping of the system also influences the natural frequency of system "See S. Patarabunditkul, "Natural Frequency Statistics of an Uncertain Plate," in *Mechatronics*: The University Of New South Wales, 2009, p. 89 (reference), incorporated herein by reference in its entirety."

The Research Motivation

Welds are often an essential part of engineering structures; therefore their contribution to the dynamic behavior cannot be neglected. Residual stresses and microstructural changes near the weld and in the welded regions due to the nonlinear thermal processes during welding, will most certainly influence the mechanical and hence the dynamic properties of the structure as a whole. Though extensive research that investigates the microstructural properties, temperature distribution and residual stresses of welded steels as a result of welding has been conducted, studies of the dependency of the mechanical and metallurgical properties on laser welding parameters of 316L ASS and the influence of the samples geometry on these properties are scarce.

Modal Testing for Flexural Analysis

Several authors have studied the effect of welding and heating on the modal parameters and flexural behavior of mechanical structures. In 1966, Dickinson observed that there was up to 20% changes in the frequency when a rectangular plate was welded and Kaldas et al performed a theoretical and an experimental study of the effect of weld runs on the flexural characteristics of a rectangular plate. They utilized a finite difference method for the prediction of residual stresses in centrally welded plates to evaluate the induced in-plane stresses, including shear and both components of normal stress. The plates were of different configuration with respect to location of the weld: the central welds, the single edge weld and two parallel edge welds.

AlZaharnah investigated the flexural motion of a cantilever assembly heated at the fixed end and the effect of the size of heat affected zone (HAZ) in the flexural motion was simulated by correlating it with the frequency and amplitude of the motion employing the finite element (FE) method "See I. T. AlZaharnah, "Flexural Characteristics of a Cantilever Plate Subjected to Heating at Fixed End," *Journal of Mechanics*, vol. 25, pp. 1-8, 2009 (reference), incorporated herein by reference in its entirety." AlZaharnah assumed a temperature heat source with varying size at the fixed edge while an impulsive load is applied at the cantilever free end. It was found that because of the temperature field in the plate during heating which modifies the modulus of elasticity of the plate, the maximum amplitude difference increases with the size of the heat source. In another study the same author examined the flexural motion of a cantilever plate heated at the fixed end with a moving laser heat source "See I. T. AlZaharnah, B. S. Yilbas, and S. A. Al-Kaabi, "Flexural Characteristics of a Laser Welded Cantilever Plate: Influence of Speed of the Heating Source," *Lasers in Engineering*, vol. 18, p. 337, 2008 (reference), incorporated herein by reference in its entirety." The Finite Element (FE) software ANSYS was used to examined the effect of the moving laser heat source on the flexural characteristics by computing the displacement difference for heating and no-heating situations and the time shift between peaks while considering different heat source speeds. In a separate study, AlZaharnah et al presented how the flexural wave characteristics at the free end during the welding of one end of a bar depends on the heating duration. The finite element software ANSYS was used to compute the wave characteristic as a function of time "See I. T. AlZaharnah, S. Al-Kaabi, and B. S. Yilbas, "Effect of Temperature Field on Flexural Wave Characteristics of a Bar Resembling Welding to Rigid Body," *Advanced Materials Research*, vol. 83, pp. 1212-1219, 2010 (reference), incorporated herein by reference in its entirety."

Investigation into the effect of heat source location on the flexural characteristics of a bar subjected to welding-liked process has also been carried out "See I. T. AlZaharnah and B. S. Yilbas, "Investigation into flexural characteristics of a bar subjected to local heating: the effect of heat source location," *Proceedings of the Institution of Mechanical Engineers, Part B: Journal of Engineering Manufacture*, vol. 222, pp. 1355-1362, 2008 (reference), incorporated herein by reference in its entirety." It was concluded that an amplitude difference variation with heat source location is not in a simple form due to the variation non-linearity. Hyder et al used the finite element method to investigate the flexural motion upon a high magnitude of recoil pressure acting on the plate and the resulting stress field inside a cantilever plate during laser evaporative/non-conductive heating "See S. J. Hyder, B. S. Yilbas, and S. Z. Shuja, "Flexural motion in laser evaporative heated cantilever workpiece: Three-dimensional analysis," *Optical and quantum electronics*, vol. 35, pp. 111-128, 2003 (reference), incorporated herein by reference in its entirety."

Another study analyzed the thermal stresses developed in a substrate subjected to laser heating process and the flexural wave propagation due to axial stress component in the surface vicinity of the substrate "See B. S. Yilbas, M. Faisal, S. Z. Shuja, and A. F. M. Arif, "Laser pulse heating of steel surface and flexural wave analysis," *Optics and lasers in engineering*, vol. 37, pp. 63-83, 2002 (reference), incorporated herein by reference in its entirety."

The stress field developed during the flexural motion of workpiece when ablated by a laser beam was considered by Yilbas et al "See B. S. Yilbas, S. J. Hyder, and S. Z. Shuja, "Flexural wave generation and stress analysis during laser evaporative heating of steel," *Proceedings of the Institution of Mechanical Engineers, Part C: Journal of Mechanical Engineering Science*, vol. 216, pp. 531-542, 2002 (reference), incorporated herein by reference in its entirety." Both the normal pressure force and the resulting amplitude and frequency of the flexural waves as well as the stress levels in the substrate material were computed using the finite element method (FEM). In a similar study, the authors carried out a 3D flexural wave analysis for a locally imbedded single aluminum cell in steel substrate, to study the effect of the location of this impurity element on the flexural wave motion of the substrate by varying its location "See S. J. Hyder, B. S. Yilbas, and S. Z. Shuja, "Laser induced flexural wave analysis: an aluminum element in steel substrate," *Journal of materials processing technology*, vol. 136, pp. 24-34, 2003 (reference), incorporated herein by reference in its entirety." After observing the flexural behavior of seven different locations for a third element, they concluded that the displacement difference is influenced significantly by the axial locations of the additional element and that this behavior reduces as the additional element location moves close to the free end.

Laser induced flexural wave propagation due to recoil pressure at the vapor-liquid interface of the evaporated surface was investigated by analytically formulating the temperature rise during heating "See B. S. Yilbas and S. J. Hyder, "Laser pulse heating and flexural wave generation during treatment of metallic surfaces," *Journal of materials processing technology*, vol. 141, pp. 1-8, 2003 (reference), incorporated herein by reference in its entirety." Both ends free-supported, both ends fixed and cantilever workpiece configurations were considered. The researchers realized that flexural wave characteristics change noticeably as the configuration varies. Damping was high i.e. flexural wave dies rapidly when both ends were fixed and except for the cantilever configuration the amplitude decreases considerably close to the workpiece ends.

Material Characterization of Laser Welding

The metallurgical study of laser welded materials has also received interest, with most investigations focused on the microstructural properties for different materials after exposure to laser beam welding. Mai et al researched the laser welding of dissimilar metals without filler materials using a pulse Nd:YAG laser with 30 W power "See T. A. Mai and A. C. Spowage, "Characterisation of dissimilar joints in laser welding of steel-kovar, copper-steel and copper-aluminium," *Materials Science and Engineering: A*, vol. 374, pp. 224-233, 2004 (reference), incorporated herein by reference in its entirety." They investigated material interaction during melting, microstructure, defects, hardness and the residual stresses at the weld zone. In a related research, the authors presented an investigation of the intermetallic compound (IMC) layers formed in a defocused laser beam welded low carbon steel and aluminum alloy in a lap joint "See K. Lee and S. Kumai, "Characterization of intermetallic compound layer formed at the weld interface of the defocused laser welded low carbon steel/6111 aluminum alloy lap joint," *Materials transactions*, vol. 47, p. 1178, 2006 (reference), incorporated herein by reference in its entirety." X-ray diffraction analysis and Transmission electron microscope with EDX analyzer (TEM-EDX) were used for the characterization of the IMC layer, the use of TEM-EDX was due to the thin IMC layer compared to the beam diameter. The tensile strength of the lap joint using an Instron-type tester under a cross-head speed of $1.7 \times 10^{-5}$ ms$^{-1}$ at room temperature and the relationship between the morphology of the IMC and the joint strength has previously been investigated "See K. Lee, S. Kumai, and T. Arai, "Interfacial microstructure and strength of steel to aluminum alloy lap joints welded by a defocused laser beam," *Materials transactions*, vol. 46, p. 1847, 2005 (reference), incorporated herein by reference in its entirety."

Yao et al developed a new method for the laser welding of copper and low carbon steel by controlling the dilution ratio of Cu to be lower than 7.2 wt % to solve the problems of material mismatches inherent in welding these dissimilar metals, the dilution ratio of Cu was controlled by carefully monitoring the laser beam interaction with Cu plate "See C. Yao, B. Xu, X. Zhang, J. Huang, J. Fu, and Y. Wu, "Interface microstructure and mechanical properties of laser welding copper-steel dissimilar joint," *Optics and lasers in engineering*, vol. 47, pp. 807-814, 2009 (reference), incorporated herein by reference in its entirety." Optical microscopy (OM) was used to study the weld morphology while the elemental distribution at microstructural level of the interface were characterized by using scanning electron microscopy (SEM) with an embedded energy dispersive spectroscopy (EDS). Taban et al studied the joints achieved by laser welding of chromium modified stainless steel by observing the microstructural and mechanical properties of the joint, as well the impact toughness, fatigue and corrosion resistance of the joint "See E. Taban, E. Deleu, A. Dhooge, and E. Kaluc, "Laser welding of modified 12% Cr stainless steel: Strength, fatigue, toughness, microstructure and corrosion properties," *Materials & Design*, vol. 30, pp. 1193-1200, 2009 (reference), incorporated herein by reference in its entirety."

In a related research by Kell et al, microstructural characterization of laser welded 316L stainless steel was performed. By combining electron backscatter diffraction (EBSD) and energy dispersion spectroscopic (EDS), they studied different phases formed on solidification as a consequence of varying welding procedures. An investigation was carried out to evaluate microstructural change after laser welding and its consequent effect on the tensile and fatigue properties of steel (type: DP600 steel) with more attention on the failure mechanism "See N. Farabi, D. L. Chen, J. Li, Y. Zhou, and S. J. Dong, "Microstructure and mechanical properties of laser welded DP600 steel joints," *Materials Science and Engineering: A*, vol. 527, pp. 1215-1222, 2010 (reference), incorporated herein by reference in its entirety." They determined that the formation of large amount of martensitic structure was responsible for the hardness; this martensitic structure was attributed to rapid cooling.

Studies were carried out by Liu et al to investigate the laser welding of K418 and 42CrMo steels "See X. B. Liu, M. Pang, J. Guo, and G. Yu, "Transmission electron microscopy characterization of laser welding cast Ni-based superalloy K418 turbo disk and alloy steel 42CrMo shaft," *Journal of Alloys and Compounds*, vol. 461, pp. 648-653, 2008 (reference); and "See X. B. Liu, G. Yu, M. Pang, J. W. Fan, H. H. Wang, and C. Y. Zheng, "Dissimilar autogenous full penetration welding of superalloy K418 and 42CrMo steel by a high power CW Nd: YAG laser," *Applied surface science*, vol. 253, pp. 7281-7289, 2007 (reference), each incorporated herein by reference in their entirety." In these studies, the microstructure of the phases present in the seam zone was characterized using X-ray diffraction (XRD) analysis, scanning electron microscope (SEM), transmission electron microscope (TEM) and energy-dispersive spectrometer (EDS). Yilbas et al carried out a study to investigate the mechanical and metallurgical properties of electron beam welded austenitic 321 stainless steel. Analysis of the first and second law of thermodynamics of the welding process was carried out. It was found that the heat-affected zone increased as the work piece thickness increased and micro cracks were present at the fusion "See B. S. Yilbas, M. Sami, J. Nickel, A. Coban, and S. A. M. Said, "Introduction into the electron beam welding of austenitic 321-type stainless steel," *Journal of materials processing technology*, vol. 82, pp. 13-20, 1998 (reference), incorporated herein by reference in its entirety."

Numerical Study of Laser Welding

Several authors have numerically investigated the laser welding process, including a heating process with a gas-assisted laser "See S. Z. Shuja and B. S. Yilbas, "3-Dimensional conjugate laser heating of a moving slab," *Applied surface science*, vol. 167, pp. 134-148, 2000 (reference), incorporated herein by reference in its entirety." Additionally, a numerical analysis was performed to study residual stresses of a butt-weld of two plates using ABAQUS and ANSYS software packages "See M. Perić, D. Stamenković, and V. Milković, "Comparison of Residual Stresses in Butt-Welded Plates Using Software Packages Abaqus and Ansys," *Scientific Technical Review* vol. Vol. 60, pp. 22-26, 2010 (reference), incorporated herein by reference in its entirety."

The electron beam welding process was numerically simulated using the finite element method "See P. Lacki and K. Adamus, "Numerical simulation of the electron beam welding process," *Computers & Structures*, vol. 89, pp. 977-985, 2011 (reference), incorporated herein by reference in its entirety." The authors analyzed the thermal field generated by the process, determined the heat-affected zone and the residual stresses in the joint. Turňa et al conducted the numerical simulation of the thermal and stress fields during the laser welding of a stainless CrNi steel type AISI 304 using a pulsed Nd: YAG laser "See M. Turňa, B. Taraba, P. Ambrož, and M. Sahul, "Contribution to Numerical Simulation of Laser Welding," *Physics Procedia*, vol. 12, pp. 638-645, 2011 (reference), incorporated herein by reference in its entirety." A 3-dimensional finite-element model employed in ANSYS program was used for simulating the welding while the heat source was parameterized by the combination of a circular disk source with a Gaussian distribution of thermal flux with center on the top surface and a line source through the thickness of workpiece.

Kazemi and Goldak developed a very simple 3-dimensional finite element method model for laser full penetration welding "See K. Kazemi and J. A. Goldak, "Numerical simulation of laser full penetration welding," *Computational Materials Science*, vol. 44, pp. 841-849, 2009 (reference), incorporated herein by reference in its entirety." Osamah performed numerical heat transfer analysis during a laser spot welding process aimed at using the double ellipsoidal representation of the laser beam, thereby including volumetric heat input from a heat source "See A. F. Osamah, "Investigation of Thermal Stress Distribution in Laser Spot Welding Process," *Al-Khwarizmi Engineering Journal*, vol. 5, pp. 33-41, 2009 (reference), incorporated herein by reference in its entirety."

Andrea et al investigated the numerical procedure for the thermal and mechanical simulation of the welding process using a 3D FEM model in ANSYS "See A. Capriccioli and P. Frosi, "Multipurpose ANSYS FE procedure for welding processes simulation," *Fusion engineering and Design*, vol. 84, pp. 546-553, 2009 (reference), incorporated herein by reference in its entirety."

Literature on numerical studies of the flexural analysis of a laser welded steel considering the post-weld effects like residual stresses and possible defects within the weld zone are not well developed. Some studies were performed on the modeling of the flexural analysis of a non-welded sample to show that the problem of the deflections of a cantilever beam in both the case of large and small deflections can be handled using simple, easy-to-assemble and low-cost experiments "See T. Belendez, C. Neipp, and A. Belendez, "Large and small deflections of a cantilever beam," *European Journal of Physics*, vol. 23, p. 371, 2002 (reference); and "See C. Neipp, "Numerical and experimental analysis of a cantilever beam: a laboratory project to introduce geometric nonlinearity in mechanics of materials," 2003 (reference), each incorporated herein by reference in their entirety."

Most research (both experimental and numerical) presented in the literature focuses on the parametric study of laser welding process, some have been directed to flexural analysis during the welding and heating processes, while the remaining concentrate on effect of welding parameters and weld runs on the modal parameters. The study of the effect of welding parameters and weld runs on the modal parameters is less researched and further investigation in this area will improve non-destructive testing techniques.

In view of the forgoing, the objective of the present invention is to develop a process for determining the quality of a post-weld laser weld-seam using flexural characteristics, whereby a welded plate and a geometrically equivalent non-welded plate are subjected to a physical impact to generate a natural vibration frequency, which is measured and compared.

BRIEF SUMMARY OF THE INVENTION

According to a first aspect, the present invention relates to a process for determining the quality of a laser weld-seam. The process involves i) subjecting a welded plate and a geometrically equivalent non-welded plate to a physical impact to generate a natural vibration frequency ii) measuring the natural vibration frequency of the welded plate and the non-welded plate with an accelerometer iii) comparing the natural vibration frequency of the welded plate to the natural vibration frequency obtained from the geometrically equivalent non-welded plate and iv) determining the uniformity of the weld by the similarity between the natural vibration frequency of the welded plate and the geometrically equivalent non-welded plate.

In one embodiment, the welded and non-welded plate comprise a low-carbon steel, and the process is non-destructive.

In one embodiment, the low-carbon steel is 316L austenitic stainless steel.

In one embodiment, the welded plate and a geometrically equivalent non-welded plate are oriented in a cantilever beam configuration with a fixed end, and the physical impact is imparted on the plates at a distance ranging from greater than x to less than L, wherein x is a distance of the weld from the fixed end, and L is a total length of the plate from the fixed end.

In one embodiment, the laser-weld seam is considered non-uniform when the % difference between the natural vibration frequency of the welded plate and the geometrically equivalent non-welded plate is greater than 13%, in the frequency range between 70-260 Hz.

In one embodiment, the natural vibration frequency of the welded and non-welded plate is determined empirically and compared to a theoretical fundamental natural frequency obtained through mathematical analysis to validate the process.

In one embodiment, the theoretical fundamental natural frequency ($\omega_{nf1}$) is calculated by the formula $$\omega_{nf1} = \sqrt{\frac{K}{M_1}}$$

where K is the stiffness and $M_1 = m_{c1} + m_{ac}$, $m_{c1}$ is the effective mass at the tip of the plate, and $m_{ac}$ is the mass of the accelerometer at the free end of the plate.

In one embodiment, the empirically determined natural vibration frequency of the welded plate does not differ by more than 10% from the theoretical fundamental natural frequency of the non-welded plate with plate thickness ranging from 1.5-3.0 mm.

In one embodiment, the natural vibration frequency of the steel plates is 100-300 Hz with a thickness ranging from 1.5-3.0 mm.

In one embodiment, the natural vibration frequency of a welded plate that has been welded with a welding speed of 200-400 mm/min is 100-140 Hz.

In one embodiment, the natural vibration frequency of a welded plate that has been welded with a laser beam power of 2-4 KW is 90-140 Hz.

In one embodiment, the physical impact is generated by an impact hammer.

According to a second aspect, the present invention relates to a process for predicting the quality of a laser weld-seam by calculating the Natural Vibration Frequency (NF) of a welded plate according to formula:

NF=−47.4−2842*(WS)+85678*(ST)+0.0168*(LP)

where WS is welding speed (mm/min), ST is sample thickness (mm), and LP is laser beam power (KW).

In one embodiment, the accuracy in terms of the coefficient of determination of the calculating is 95-99.9%.

In one embodiment, the calculating does not differ from the natural frequency measured empirically by more than 13% with a laser beam power of 1.5-4.5 KW.

In one embodiment, the calculating does not differ from the natural frequency measured empirically by more than 20% with a sample thickness of 1.5-2.5 mm.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
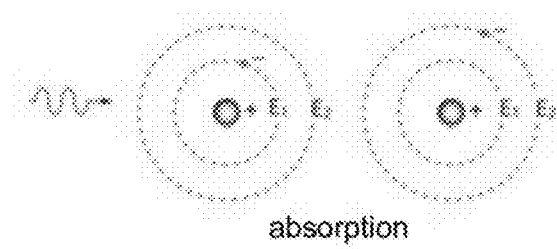
FIG. 1A is a schematic of absorption.
Figure 1B:
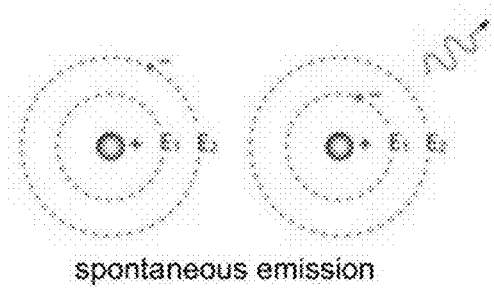
FIG. 1B is a schematic of spontaneous emission.
Figure 1C:
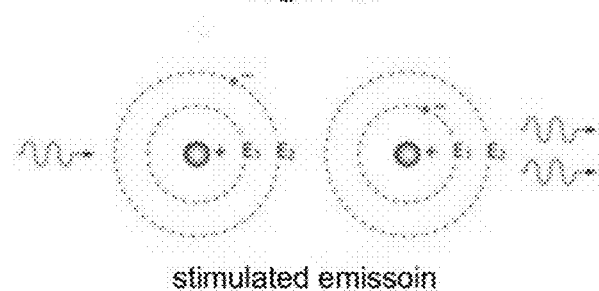
FIG. 1C is a schematic of stimulated emission.
Figure 2:
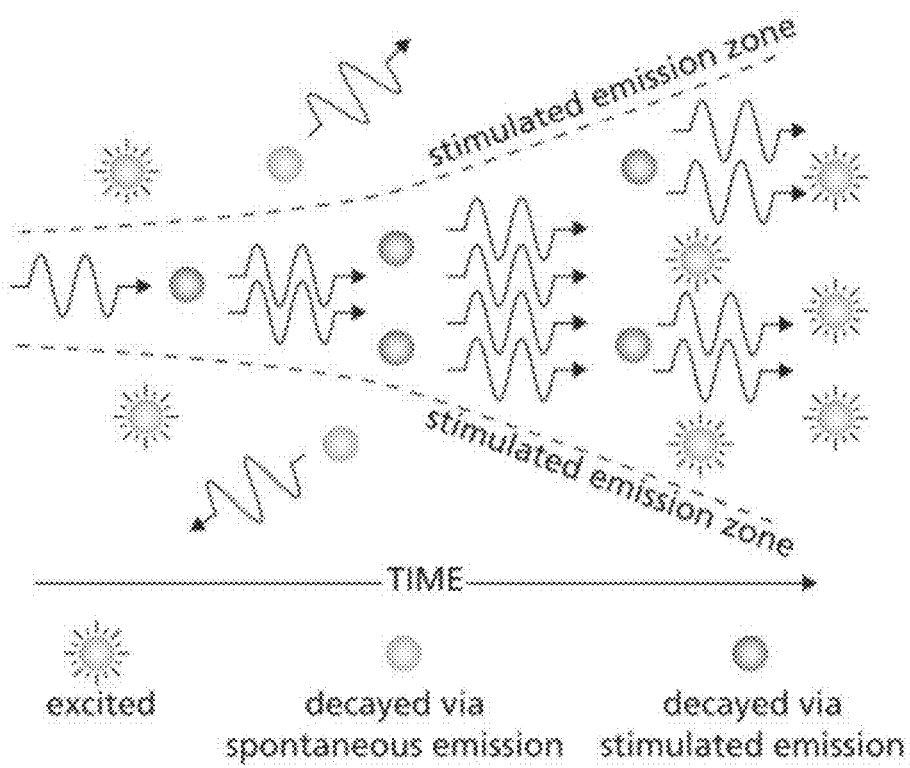
FIG. 2 is a schematic of amplification by stimulated emission.
Figure 3:
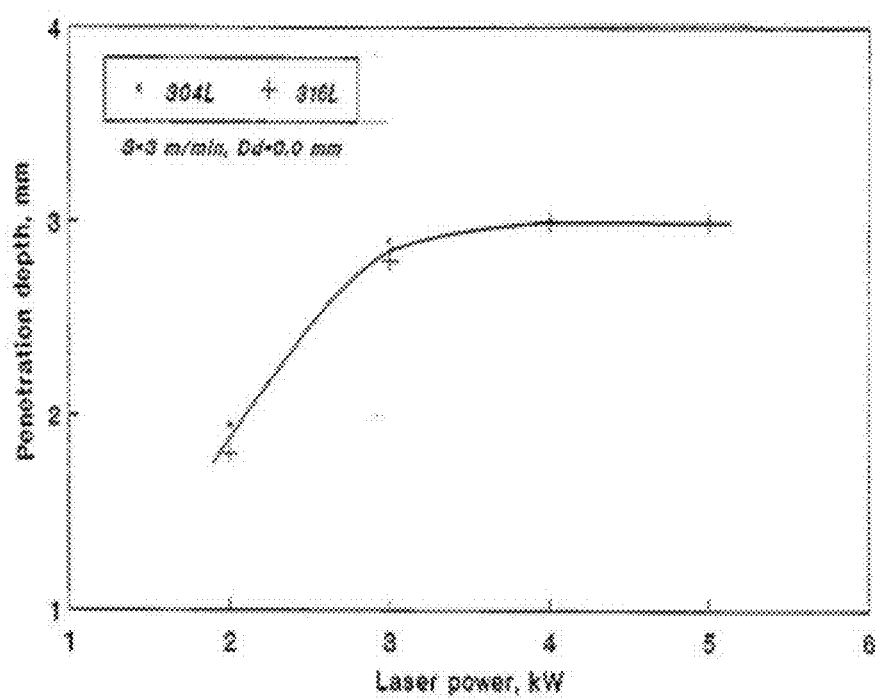
FIG. 3 is an illustration of the effect of laser power on penetration depth of type 304 and type 316L steel welds.
Figure 4:
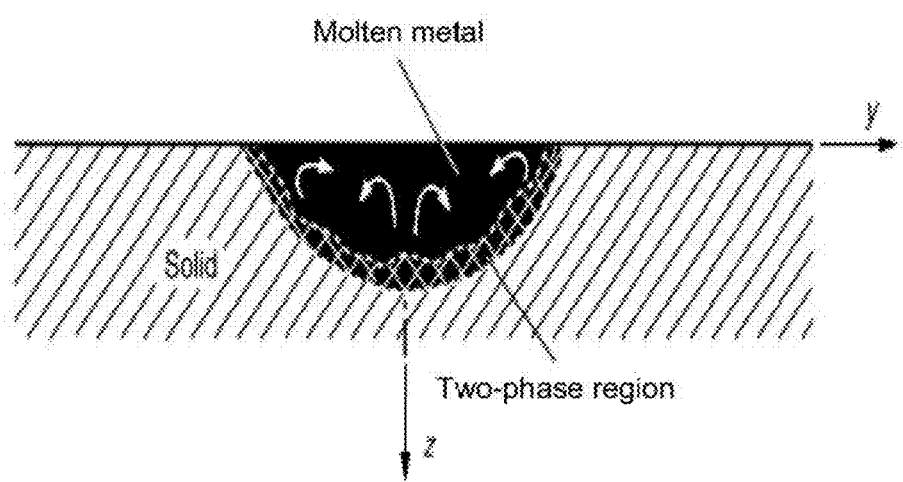
FIG. 4 is a schematic of Conduction Mode Welding.
Figure 5:
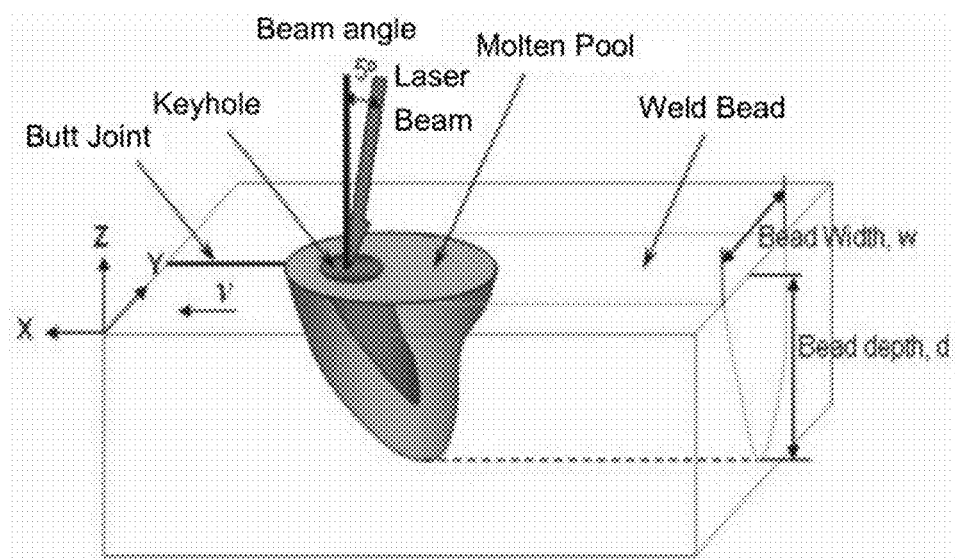
FIG. 5 is a schematic of the keyhole mode laser welding process illustrating bending of the keyhole in the direction of workpiece travel.
Figure 6A:
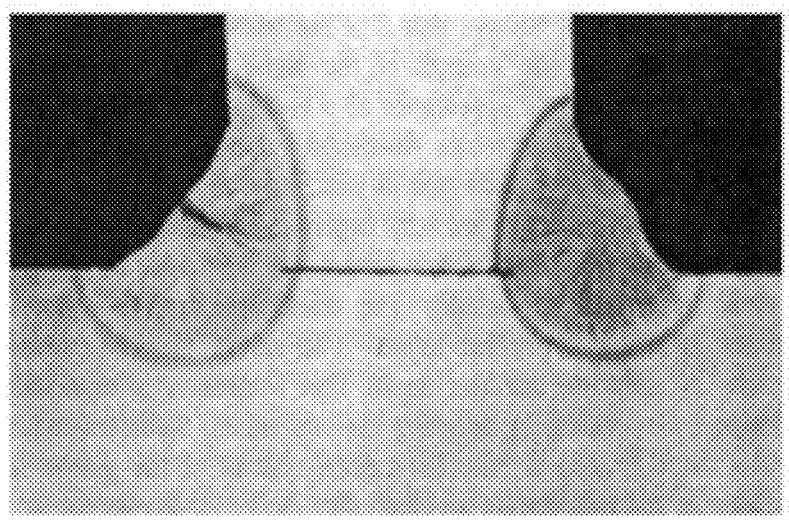
FIG. 6A is an image of a hot crack in a fillet weld.
Figure 6B:
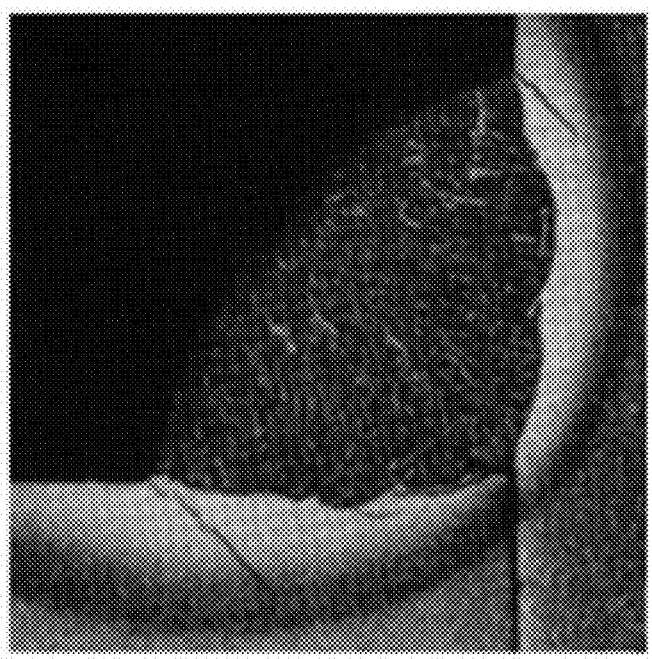
FIG. 6B is an image of a cold crack in the heat-affected zone of a fillet weld.

Referring now to the drawings, wherein like reference numerals designate identical or corresponding parts throughout the several views.

According to a first aspect, the present invention relates to a process for determining the quality of a laser weld-seam 1001. The process involves i) subjecting a welded plate 1002 and a geometrically equivalent non-welded plate to a physical impact to generate a natural vibration frequency ii) measuring the natural vibration frequency of the welded plate and the non-welded plate with an accelerometer iii) comparing the natural vibration frequency of the welded plate to the natural vibration frequency obtained from the geometrically equivalent non-welded plate and iv) determining the uniformity of the weld by the similarity between the natural vibration frequency of the welded plate and the geometrically equivalent non-welded plate.

Welding is a fabrication or sculptural process that joins materials or joins the same material together, by causing coalescence. This is often done by melting the workpieces and forming a pool of molten material that cools to become a strong joint, with pressure sometimes used in conjunction with heat, or by itself, to produce the weld. Laser beam welding is a welding technique used to join multiple pieces of metal through the use of a laser. A laser differs from other sources of light because it emits light coherently. Spatial coherence allows a laser to be focused to a tight spot, and also allows a laser beam to stay narrow over long distances. The beam provides a concentrated heat source, allowing for narrow, deep welds and high welding rates. When subjected to a physical impact, every material exhibits natural flexural characteristics (e.g. stiffness, damping, and natural vibrational frequency). The laser welding process, as with any welding process, induces defects and residual stresses in the welded region and structure respectively. The presence of defects developed in a component changes its flexural characteristics, such as the natural vibrational frequency, as a result of changing the material properties of the structure during welding. In this invention, the shift in the position of the natural vibrational frequency is then used to determine the viability of welded structure.

Two or more workpieces can be welded together in several ways with differing geometries. The five basic types of weld joints that may be used are the butt joint, lap joint, corner joint, edge joint, and T-joint.

After welding, a number of distinct regions can be identified in the weld area. The weld itself is called the fusion zone. This zone may also be referred to as the weld bead. It is surrounded by the heat-affected zone, the area that had its microstructure and properties altered by the weld, but is not part of the workpiece fusion. These properties depend on the base material's behavior when subjected to heat. The metal in the heat affected zone is often weaker than both the base material and the fusion zone, and is also where residual stresses are commonly found. Outside of the heat affected zone is the base material, which is unaltered from the welding process.

The dimensions of the fusion zone may be characterized by the width of the weld bead and the thickness of the weld bead (i.e. how deeply the weld penetrates into the sample). The weld bead width is the linear distance of the weld measured perpendicular to the weld line. The thickness of the weld is a measurement of how deep the weld penetrates into the workpiece, measured from the surface of the weld line. During laser welding, the shape of the fusion zone is affected by several factors, including the laser beam power, welding speed, and sample thickness. Therefore, the shape of a fusion zone tends to be non-uniform and the weld bead width and thickness varies across the weld. In regards to the present invention, the weld bead width refers to a mean value of the weld bead width measured at the top (surface), center (mid-point), and the bottom (longest sub-surface distance of the weld bead from the surface). The weld bead thickness refers to a mean value of the weld bead measured as the longest sub-surface distance of the weld bead from the surface.

In one embodiment, the weld bead width is 0.4-1.2, preferably 0.5-1.1, more preferably 0.6-1.0 mm with a welding speed of 200-400 mm/min and a laser beam power of 2.5-3.5 KW.

In one embodiment, the weld bead width is 0.3-0.9, preferably 0.35-0.8, more preferably 0.4-0.7 mm with a welding speed of 200-400 mm/min and a laser beam power of 3.5-4.5 KW.

In one embodiment, the weld bead thickness/width ratio is 1.0-3.0, preferably 1.3-2.5, more preferably 1.5-2.3 with a welding speed of 200-400 mm/min and a laser beam power of 2.5-3.5 KW.

In one embodiment, the weld bead thickness/width ratio is 3.0-7.0, preferably 3.5-6.5, more preferably 4.0-6.0 with a welding speed of 200-400 mm/min and a laser beam power of 3.5-4.5 KW.

In one embodiment, the weld bead width is 0.45-1.0, preferably 0.5-0.95, more preferably 0.55-0.90 mm with a welding speed of 380-420 mm/min and a laser beam power of 2-4 KW.

In one embodiment, the weld bead thickness/width ratio is 1.0-3.0, preferably 1.3-2.8, more preferably 1.5-2.75 with a welding speed of 380-420 mm/min and a laser beam power of 1.5-4.5 KW.

In one embodiment, the weld bead width is 0.40-1.2, preferably 0.45-1.0, more preferably 0.5-0.95 mm with a sample thickness of 1.5-3.0 mm, a welding speed of 280-320 mm/min and a laser beam power of 3.5-4.5 KW.

In one embodiment, the weld bead thickness/width ratio is 0.8-7.0, preferably 0.9-6.5, more preferably 1.0-6.0 with a sample thickness of 1.5-3.0, a welding speed of 280-320 mm/min and a laser beam power of 3.5-4.5 KW.

In terms of the present invention, the welded and non-welded plates are square-like or rectangular in shape. In one embodiment, the welded and non-welded samples can be, but are not limited to circular, oval, or triangular shapes. In one embodiment, a "geometrically equivalent" non-welded plate refers to a plate with the same general shape and substantially the same length, width, and thickness as a welded plate. In one embodiment, the welded samples are welded with a butt-joint autogenously to form rectangular shaped samples. In one embodiment, the welded samples have a length of 35-45 mm, a width of 18-26 mm, and a thickness of 1.0-4.0 mm. As the non-welded samples are "geometrically equivalent", the non-welded samples also have a length of 35-45 mm, a width of 18-26 mm, and a thickness of 1.0-4.0 mm. In the present invention, it is envisaged that the welded and the non-welded plate may take on the form of other shapes besides rectangles, and may also have dimensions that differ from the dimensions above. In this regard, it is envisaged that the dimensions of the welded plate and the "geometrically equivalent" non-welded plate do not differ by more than 10%, preferably 5%, more preferably 3%, even more preferably 1% in any single dimension, which includes length, width, and depth, measured at any location within the shape of the plate samples. The geometrically equivalent plate also refers to a plate composed of substantially the same material (i.e. the same grade of steel, etc.).

Steel is an alloy of iron and carbon that is widely used in construction and other applications because of its high tensile strength and low cost. Carbon, other elements, and inclusions within iron act as hardening agents that prevent the movement of dislocations that naturally exist in the iron atom crystal lattices. The carbon in typical steel alloys may contribute up to 2.1% of its weight. Steels can be broadly categorized into four groups based on their chemical compositions: carbon steels, alloy steels, stainless steels, and tool steels.

Carbon steels contain trace amounts of alloying elements and account for 90% of total steel production. Carbon steels can be further categorized into three groups depending on their carbon content: low carbon steels/mild steels contain up to 0.3% carbon, medium carbon steels contain 0.3-0.6% carbon, and high carbon steels contain more than 0.6% carbon.

Alloy steels contain alloying elements (e.g. manganese, silicon, nickel, titanium, copper, chromium and aluminum) in varying proportions in order to manipulate the steel's properties, such as its hardenability, corrosion resistance, strength, formability, weldability or ductility.

Stainless steels generally contain between 10-20% chromium as the main alloying element and are valued for high corrosion resistance. With over 11% chromium, steel is about 200 times more resistant to corrosion than mild steel. These steels can be divided into three groups based on their crystalline structure: austenitic steels, ferritic steels, and martensitic steels.

Tool steels contain tungsten, molybdenum, cobalt and vanadium in varying quantities to increase heat resistance and durability, making them ideal for cutting and drilling equipment.

In one embodiment, the welded and the non-welded plates comprise a carbon steel, an alloy steel, a stainless steel, or a tool steel.

In one embodiment, the welded and non-welded plate comprise a low-carbon steel.

Austenite, also known as gamma-phase iron ($\gamma$-Fe), is a metallic, non-magnetic allotrope of iron or a solid solution of iron, with an alloying element. 300 Series austenitic stainless steel has austenite as its primary phase (face centered cubic crystal). Austenitic stainless steels can be tested with non-destructive testing.

In one embodiment, the low-carbon steel is 316L austenitic stainless steel. In one embodiment, the 316L austenitic stainless steel is composed of C, Mg, P, S, Si, Cr, Ni, Mo, N, and Fe.

In one embodiment, the welded plate is welded with a laser by a conduction mold welding process or a keyhole mold welding process.

In one embodiment, the welded plates are welded without the use of filler material.

In one embodiment, the process is non-destructive.

In one embodiment, the physical impact is generated by an impact hammer 1003. In the present invention, the natural vibrational frequency of welded and non-welded samples are measured with an accelerometer 1004. An accelerometer is a device that measures proper acceleration ("g-force"), and may therefore be used to detect and measure vibration as a change in proper acceleration. The accelerometer is in communication with a computer 1006.

A cantilever is a beam anchored at only one end. The beam carries the load to the support where it is forced against by a moment and shear stress. Cantilever construction allows for overhanging structures without external bracing. In one embodiment, the welded plate and a geometrically equivalent non-welded plate are oriented in a cantilever beam configuration with a fixed end 1005.

In one embodiment, in terms of the fixed end being 0% and the total length of the welded or non-welded plate from the fixed end being 100%, the weld is located 20-80%, preferably 30-70%, more preferably 40-60% of the length of the welded or non-welded plate.

In one embodiment, the accelerometer is located on, and rests upon the top side of the welded or non-welded plate.

In one embodiment, in terms of the fixed end being 0% and the total length of the welded plate from the fixed end being 100%, the accelerometer is located 60-100%, preferably 70-100%, more preferably 80-100%, even more preferably 90-100% of the length of the welded or non-welded plate.

In one embodiment, the physical impact is imparted on the welded or non-welded plate at a distance ranging from greater than x to less than L, wherein x is a distance of the weld from the fixed end, and L is a total length of the welded plate from the fixed end.

In one embodiment, the physical impact is generated from the top of the welded or non-welded plate, on the same side as the accelerometer.

In an alternative embodiment, the physical impact is generated from the bottom of the welded or non-welded plate, opposite of the accelerometer.

Applying a physical impact to a system will induce flexural motion and the system will oscillate. Natural frequency is the frequency at which a system tends to oscillate in the absence of any driving or damping force. A common example of such a phenomenon is a tuning fork. A tuning fork is an acoustic resonator in the form of a two-pronged fork with the prongs formed from a U-shaped bar of elastic metal, usually steel. It resonates at a specific constant pitch when set vibrating by striking it against a surface or with an object, and emits a pure musical tone after waiting a moment to allow some high overtones to die out. The pitch that a particular tuning fork generates depends on the length and mass of the two prongs. It is frequently used as a standard of pitch to tune musical instruments. A tuning fork produces a very pure tone, with most of the vibrational energy at the fundamental frequency, and little at the overtones (harmonics). Therefore, in a plot of vibrational frequency vs amplitude, most of the frequency will be in a tight range, regardless of the physical impact imparted on the tuning fork. In other words, rather than a system producing a single frequency with a single amplitude, the vibrational frequency of the oscillations tend to exhibit a Gaussian-like distribution as a function of amplitude, with most frequency values in a tight range. Similar to a tuning fork, when welded or non-welded plates are oriented in a cantilever beam configuration and a physical impact is applied, the sample will oscillate, with most of the vibrational energy at the fundamental frequency, irrespective of the force of physical impact. When the empirically determined vibrational frequency is plotted as a function of amplitude, a Gaussian-like distribution is produced, with most of the frequency values in a tight range. In terms of the present invention, the natural vibration frequency refers to the frequency value at the apex of the signal amplitude in a plot of frequency vs amplitude. Alternatively, the natural vibrational frequency values, when used for comparison to another sample, may refer to any point within the frequency curve as a function of amplitude, as long as the comparison value is also selected from the same point of the respective frequency curve of the compared sample. For example, the two frequency values (one with a higher frequency and one with a lower frequency) determined from the amplitude mid-point of a frequency curve from a welded sample may be compared with the two frequency values at the amplitude mid-point of a frequency curve of a non-welded sample.

In the present invention, a natural vibration frequency of less than 65, preferably less than 61 Hz is considered electrical noise.

In terms of the present invention, the natural vibration frequency of a welded plate may depend on the sample thickness, the welding speed, and/or the laser beam power.

Moment of inertia is the mass property of a rigid body that determines the torque needed for a desired angular acceleration about an axis of rotation. A larger moment of inertia around a given axis requires more torque to increase the rotation, or to stop the rotation, of a body about that axis. Moment of inertia depends on the amount and distribution of its mass, and can be found through the sum of moments of inertia of the masses making up the whole object, under the same conditions.

Thickness of the plate is one variable which can affect the natural vibration frequency of a material. A large plate thickness results in an increased moment of inertia of the plate, which in turn increases the resistance of the plate to flexure motion and an increase of the natural frequency.

In one embodiment, the natural vibration frequency of the non-welded steel plates is 80-350, preferably 90-320, more preferably 100-300 Hz with a thickness ranging from 1.0-4.0, preferably 1.3-3.5, more preferably 1.5-3.0 mm.

In one embodiment, the natural vibration frequency of welded steel plates, that are welded with a laser beam power of 2-4 KW with 350-450 mm/min welding speed, is 80-250, preferably 90-220, more preferably 100-200 Hz with a thickness ranging from 1.0-3.0, preferably 1.3-2.8, more preferably 1.5-2.5 mm.

Welding speed, or the rate at which a laser traverses a distance per amount of time, is another variable that may affect the flexural motion properties of welded samples. Often, higher welding speed leads to a finer weld microstructure due to an increase in both solidification and cooling rates of the welded area. A finer microstructure typically increases the material stiffness and resistance to deformation, which results in lower natural frequency.

In one embodiment, the natural vibration frequency of a welded plate that has been welded with a welding speed of 150-450, preferably 180-420, more preferably 200-400 mm/min is 80-160, preferably 90-150, more preferably 100-140 Hz.

Laser beam power used during a welding process is another factor that influences the natural vibration frequency of welded samples. An increase in laser beam power results in a coarser weld microstructure and reduced resistance to deformation. Increasing laser beam power thus increases the natural vibration frequency of welded samples.

In one embodiment, the natural vibration frequency of a welded plate that has been welded with a laser beam power of 1-5 KW, preferably 2-4 KW is 70-160, preferably 80-150, more preferably 90-140 Hz.

In the present invention, the natural vibration frequency of a welded sample and a geometrically equivalent non-welded sample is compared to determine the uniformity of the weld.

In the present invention, "% difference" when comparing two numerical values refers to the absolute difference between the two values, divided by the average of the two values, all multiplied by 100. In one embodiment, the frequency values obtained empirically for a welded and a non-welded plate using the cantilever beam configuration are compared. The frequency values obtained for a welded and a geometrically equivalent non-welded plate are compared as a % difference, wherein the frequency values are selected from the apex of the signal amplitude in a plot of frequency vs signal amplitude.

In one embodiment, the laser-weld seam is considered non-uniform when the % difference between the natural vibration frequency of the welded plate and the geometrically equivalent non-welded plate, determined empirically, is greater than 15%, preferably 14%, more preferably 13%, in the frequency range between 60-280, preferably 65-270, more preferably 70-260 Hz.

It is envisaged that this method could be used by one of skill in the art to determine weld quality of a welded sample as a quality control procedure. For instance, it is envisaged that the method of the present invention may be used as a feedback mechanism by which a welder/manufacturer compares the uniformity between a welded sample and a non-welded sample, then if a welded sample is deemed non-uniform, the welding process is repeated with differing welding parameters (e.g. weld speed, laser beam power, etc.) until the welded sample is deemed uniform with respect to the non-welded sample.

In one embodiment, the natural vibration frequency of the welded and non-welded plate is determined empirically and compared to a theoretical fundamental natural frequency obtained through mathematical analysis to validate the empirical process. In the present invention, the theoretical fundamental natural frequency ($\omega_{nf1}$) is calculated by the formula $$\omega_{nf1} = \sqrt{\frac{K}{M_1}}$$

where K is the stiffness and $M_1=m_{c1}+m_{ac}$, $m_{c1}$ is the effective mass at the tip of the plate, and $m_{ac}$ is the mass of the accelerometer at the free end of the plate.

In one embodiment, the frequency value obtained empirically for a welded plate using the cantilever beam configuration is compared to the theoretical natural frequency obtained through mathematical analysis of a geometrically equivalent non-welded plate to provide a % difference.

In one embodiment, the empirically determined natural vibration frequency of the welded plate does not differ by more than 15%, preferably, 13%, more preferably 11%, even more preferably 10% from the theoretical fundamental natural frequency of the non-welded sample with plate thickness ranging from 1.0-4.0, preferably 1.3-3.5, more preferably 1.5-3.0 mm.

It is envisaged that the method of comparing the empirical vibration frequency of a welded sample to the theoretical calculated frequency of a non-welded sample may be used as a feedback mechanism to determine the quality of the cantilever beam experimental setup. As such, if the empirically determined frequency of a welded sample differs by a % that is not considered acceptable from the theoretical natural frequency obtained through mathematical analysis, the cantilever beam experimental setup may be modified so that the empirical and theoretical frequency values fall into an acceptable % difference range.

According to a second aspect, the present invention relates to a process for predicting the quality of a laser weld-seam by calculating the Natural Vibration Frequency (NF) of a welded plate according to formula:

$$NF=-47.4-2842*(WS)+85678*(ST)+0.0168*(LP)$$

where WS is welding speed (mm/min), ST is sample thickness (mm), and LP is laser beam power (KW).

In one embodiment, the accuracy in terms of the coefficient of determination of the calculating is 90-99.9%, preferably 93-99.9%, more preferably 95-99.9%.

In one embodiment, the calculating does not differ from the natural frequency measured empirically by more than 15%, preferably 14%, more preferably 13% with a laser beam power of 1.5-4.5 KW.

In one embodiment, the calculating does not differ from the natural frequency measured empirically by more than 25%, preferably 23%, preferably 20% with a sample thickness of 1.5-2.5 mm.

Figure 69:
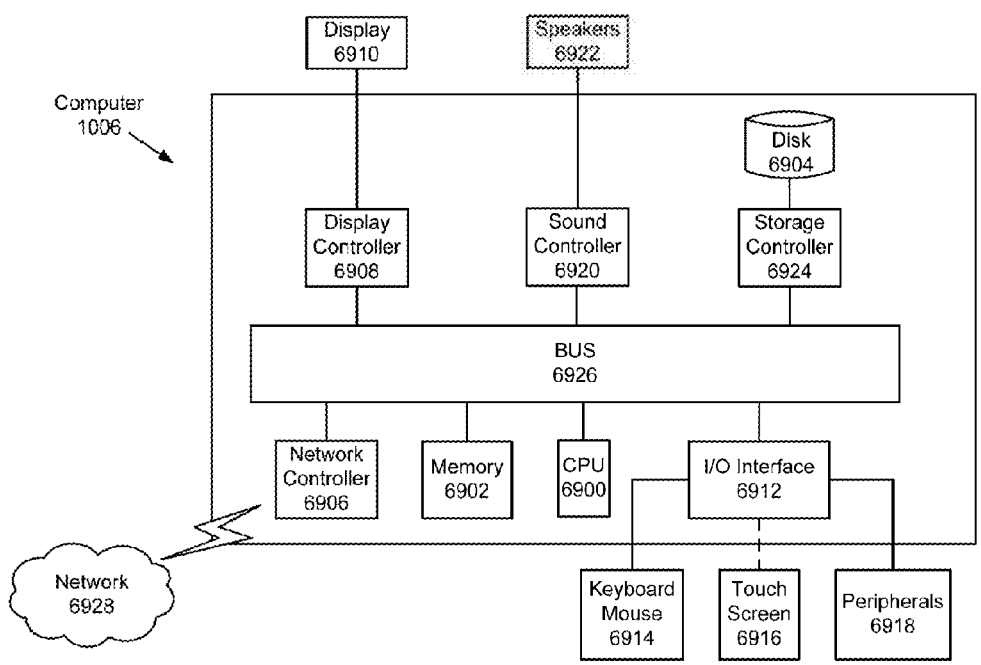
FIG. 69 is a block diagram of the computer 1006.

Next, a hardware description of the computer 1006 according to exemplary embodiments is described with reference to FIG. 69. In FIG. 69, the computer 1006 includes a CPU 6900 which performs the processes described above. The process data and instructions may be stored in memory 6902. These processes and instructions may also be stored on a storage medium disk 6904 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computer 1006 communicates, such as a server or computer.

Further, the claimed advancements may be provided as a utility application, background daemon, or component of an operating system, or combination thereof, executing in conjunction with CPU 6900 and an operating system such as Microsoft Windows 7, UNIX, Solaris, LINUX, Apple MAC-OS and other systems known to those skilled in the art.

CPU 6900 may be a Xenon or Core processor from Intel of America or an Opteron processor from AMD of America, or may be other processor types that would be recognized by one of ordinary skill in the art. Alternatively, the CPU 6900 may be implemented on an FPGA, ASIC, PLD or using discrete logic circuits, as one of ordinary skill in the art would recognize. Further, CPU 6900 may be implemented as multiple processors cooperatively working in parallel to perform the instructions of the inventive processes described above.

The computer 1006 in FIG. 69 also includes a network controller 6906, such as an Intel Ethernet PRO network interface card from Intel Corporation of America, for interfacing with network 6928. As can be appreciated, the network 6928 can be a public network, such as the Internet, or a private network such as an LAN or WAN network, or any combination thereof and can also include PSTN or ISDN sub-networks. The network 6928 can also be wired, such as an Ethernet network, or can be wireless such as a cellular network including EDGE, 3G and 4G wireless cellular systems. The wireless network can also be WiFi, Bluetooth, or any other wireless form of communication that is known.

The computer 1006 further includes a display controller 6908, such as a NVIDIA GeForce GTX or Quadro graphics adaptor from NVIDIA Corporation of America for interfacing with display 6910, such as a Hewlett Packard HPL2445w LCD monitor. A general purpose I/O interface 6912 interfaces with a keyboard and/or mouse 6914 as well as a touch screen panel 6916 on or separate from display 6910. General purpose I/O interface also connects to a variety of peripherals 6918 including printers and scanners, such as an OfficeJet or DeskJet from Hewlett Packard.

A sound controller 6920 is also provided in the computer 1006, such as Sound Blaster X-Fi Titanium from Creative, to interface with speakers/microphone 6922 thereby providing sounds and/or music.

The general purpose storage controller 6924 connects the storage medium disk 6904 with communication bus 6926, which may be an ISA, EISA, VESA, PCI, or similar, for interconnecting all of the components of the computer 1006. A description of the general features and functionality of the display 6910, keyboard and/or mouse 6914, as well as the display controller 6908, storage controller 6924, network controller 6906, sound controller 6920, and general purpose I/O interface 6912 is omitted herein for brevity as these features are known.

The examples below are intended to further illustrate protocols for preparing and characterizing welded samples, and testing and predicting the flexural characteristics of the welded and non-welded samples, and are not intended to limit the scope of the claims.

Example 1

Experimentation and Methodology

The following sections outline the laser welding process, modal testing for flexural analysis and the characterization of the samples conducted in this study.

Laser Welding Experimental Setup and Welding Parameters

The $CO_2$ laser (LC-ALPHAIII) delivering nominal output power of 2 kW at pulse mode with different frequencies was used to irradiate the workpiece surface. The nominal focal length of the focusing lens is 127 mm. Argon assisting gas emerging from the conical nozzle and co-axially with the laser beam was used. The welding conditions are given in Table 1.

Several commercial 316L austenitic stainless steel (ASS) blanks were laser welded with different geometrical and welding parameters. Table 2 shows the chemical composition of 316L steel. Rectangular machined surface samples were prepared with dimension 40 mm×22 mm×thickness mm and butt jointed autogenously using a carbon dioxide laser with the continuous wave mode. It should be mentioned that these samples were welded without filler material.

TABLE 1

Laser Welding Conditions

| Laser Power [W] | Scanning Speed (mm/min) | Nozzle Gap [mm] | Nozzle Dia. [mm] | Focus Setting [mm] | Focus Dia. [mm] | Argon Pressure [KPa] |
|---|---|---|---|---|---|---|
| 2000-4000 | 100-400 | 1.5 | 1.5 | 127 | 0.8 | 600 |

TABLE 2

316L Steel chemical composition

| | Element | | | | | | | | |
|---|---|---|---|---|---|---|---|---|---|
| | C | Mg | P | S | Si | Cr | Ni | Mo | N | Fe |
| Composition (wt %) | 0.03 | 2.00 | 0.045 | 0.03 | 0.75 | 16.00 | 10.00 | 2.00 | 0.10 | Balance |

The welding parameters considered in this study are the feed rate (or welding speed) and the welding power while thickness of the blanks were varied. Other laser welding parameters not stated here were kept constant throughout the welding process. Tables 3-6 respectively illustrate the parametric variation for the feed rate, laser welding power and thickness of the blanks.

TABLE 3

Samples with varied beam feed rate only

| Sample # | Thickness | Power (W) | Feed(mm/min) |
|---|---|---|---|
| 10 | 1.5 | 3000 | 200 |
| 11 | 1.5 | 3000 | 300 |
| 12 | 1.5 | 3000 | 400 |

TABLE 4

Samples with varied beam feed rate only at higher power

| Sample # | Thickness | Power (W) | Feed(mm/min) |
|---|---|---|---|
| 142 | 2.5 | 4000 | 200 |
| 143 | 2.5 | 4000 | 300 |
| 144 | 2.5 | 4000 | 400 |

TABLE 5

Samples with varied power only

| Sample # | Thickness | Power (W) | Feed(mm/min) |
|---|---|---|---|
| 8 | 1.5 | 2000 | 400 |
| 12 | 1.5 | 3000 | 400 |
| 16 | 1.5 | 4000 | 400 |

TABLE 6

Samples with varied geometry only

| Sample # | Thickness | Power (W) | Feed(mm/min) |
|---|---|---|---|
| Set A | | | |
| 12 | 1.5 | 3000 | 400 |
| 76 | 2 | 3000 | 400 |
| 140 | 2.5 | 3000 | 400 |
| Set B | | | |

TABLE 6-continued

Samples with varied geometry only

| Sample # | Thickness | Power (W) | Feed(mm/min) |
|---|---|---|---|
| 15 | 1.5 | 4000 | 300 |
| 143 | 2.5 | 4000 | 300 |
| 207 | 3 | 4000 | 300 |

Modal Testing for Flexural Analysis

In order to investigate the flexural behavior of the welded 3161 blanks, a first order modal analysis was carried out to determine modal parameters like natural frequency and stiffness. This section presents the mathematical formulations governing the analysis.

Theoretical Modal Analysis

Figure 7:
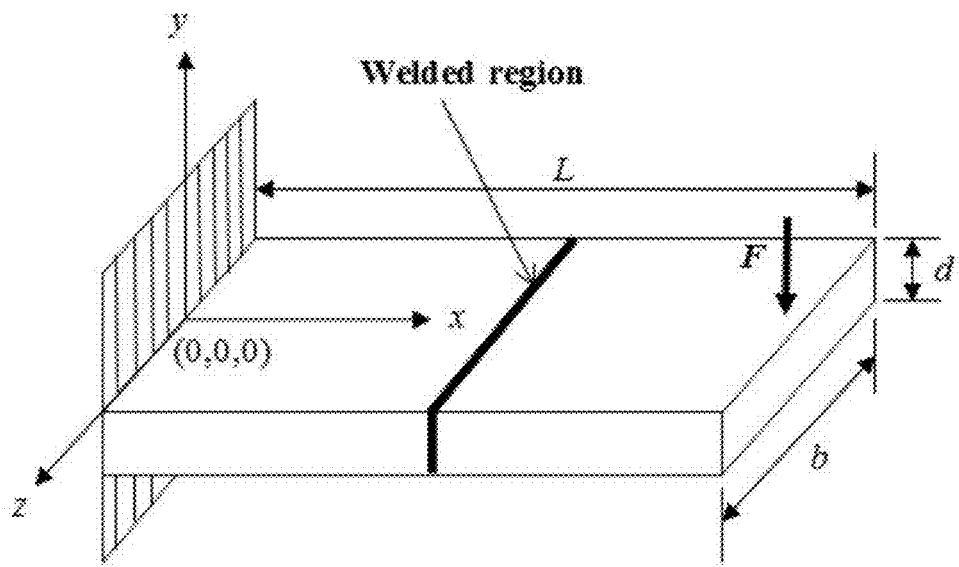
FIG. 7 is a schematic diagram of the cantilever configuration of a plate.

The analysis of the response of a vibrational system relies on constructing a mathematical model or an equation of motion in order to calculate natural frequencies and mode shapes. The vibration is characterized by amplitude, speed, acceleration and frequency spectrum. The measures which characterize the movement (vibration) of the system that is the displacement (d), speed (v) and acceleration (a) can be defined. FIG. 7 shows schematics diagram of laser welded plates and the coordinate system. The acceleration of a bar resembling the plate can be written as "See D. V. Florica Novăcescu, and Horia Ciocârlie, "The Study of Vibrations of an Elastic System Using the LabView Graphic Programming Medium," *International Journal of Modeling and Optimization*, vol. 2, pp. 208-212, 2012 (reference), incorporated herein by reference in its entirety":

$$d = D\sin\omega t \quad (1)$$

$$v = dd/dt = D\omega\cos\omega t \quad (2)$$

$$a = \frac{dv}{dt} = \frac{d^2d}{dt^2} = D\omega^2\sin\omega t \tag{3}$$

where D is the amplitude, w is the angular velocity and t is the time.

A cantilever beam can be considered as two-dimensional, since it has a uniformly distributed mass and stiffness across the length of the beam with finite thickness, which is significantly less than its breadth and length. When the beam is subjected to a free flexural motion the geometry equation can be expressed as:

$$\frac{d^4z}{dx^4} - \left(\frac{\omega_{nf}^2 m}{EI}\right)y = 0 \tag{4}$$

where $\omega_{nf}$ represents the natural frequency values. E is the modulus of elasticity of the plate material, I is the moment of inertia, m is the mass per unit length of the plates and x, y, z are the distances in the x, y, z coordinates system (FIG. 7). The general solution of the differential equation presented in Eqn. (4) and describing the flexural motion of a blank without welding can be written as:

$$z = A\cosh\left[\left(\frac{m\omega_{nf}^2}{EI}\right)^{1/4} x\right] + B\sinh\left[\left(\frac{m\omega_{nf}^2}{EI}\right)^{1/4} x\right] + C\cos\left[\left(\frac{m\omega_{nf}^2}{EI}\right)^{1/4} x\right] + D\sin\left[\left(\frac{m\omega_{nf}^2}{EI}\right)^{1/4} x\right] \tag{5}$$

where A, B, C, and D are the integration constants and can be found after substituting the following boundary conditions in equation (5). The boundary conditions can be expressed as:

At the clamped end of the uniform bar where x=0:

$$y|_{x=0} = 0 \text{ and } \frac{dy(x)}{dx}\bigg|_{x=0} = 0 \tag{5a}$$

And at the free end where x=1:

$$\frac{d^2y(x)}{dx^2}\bigg|_{x=l} = 0 \text{ and } \frac{d^3y(x)}{dx^3}\bigg|_{x=l} = 0 \tag{5b}$$

Therefore equation (5) reduces to $$\cosh\left[\left(\frac{m\omega^2}{EI}\right)^{1/4} l\right]\cos\left[\left(\frac{m\omega^2}{EI}\right)^{1/4} l\right] + 1 = 0 \tag{6}$$

According to previous studies "See J. S. Wu and T. L. Lin, "Free vibration analysis of a uniform cantilever beam with point masses by an analytical-and-numerical-combined method," *Journal of Sound and Vibration*, vol. 136, pp. 201-213, 1990 (reference); and "See J. P. Chopade and R. B. Barjibhe, "Free Vibration Analysis of Fixed Free Beam with Theoretical and Numerical Approach Method," *International Journal of Innovations In Engineering and Technology (IJIET)*, vol. 2, pp. 352-356, 2013 (reference), each incorporated herein by reference in their entirety", the resulting fundamental natural frequency corresponding to the first mode of motion for the uniform blank is $$\omega_{nf} = 1.875^2 \sqrt{\frac{EI}{ml^4}} \tag{7}$$

The flexural properties of a cantilever beam are shown in the FIG. 7. The damped natural frequency is calculated according to the well-known formula "See S. G. Kelly, *Fundamentals of Mechanical Vibrations*, Second Edition ed.: McGraw-Hill Higher Education, 2000 (reference); and "See L. Meirovitch, *Elements of Vibration Analysis*, Second Edition ed.: McGraw-Hill Book Company, 1986 (reference), each incorporated herein by reference in their entirety":

$$\omega_d = \omega_{nf}\sqrt{1-\xi^2} \tag{8}$$

where $\xi$ is the damping coefficient of the uniform blank. From eqn. (7), natural frequency of the first mode in radian is given by:

$$\omega_{nf} = 1.875^2 \sqrt{\frac{EI}{mL^4}} \tag{9}$$

In this case of equation (9), $$m = \rho bLd \tag{10}$$

Where b is the breadth, d is the width (thickness) and L is the length of the blanks For rectangular blanks the moment of inertial I is given by "See L. Daniel J. Marquez-Chisolm, USAF, "Natural Frequencies and Mode Shapes of a Nonlinear, Uniform Cantilevered Beam (MSc Thesis)" in *Department of Aeronautics and Astronautics* Ohio: Air Force Institute of Technology, 2006, p. 195 (reference), incorporated herein by reference in its entirety":

$$I = \frac{bd^3}{12} \tag{11}$$

The circular natural frequency in hertz is related by:

$$f_n = \frac{\omega_{nf}}{2\pi} \tag{12}$$

The natural frequency, $\omega_{nf}$ of undamped system is related to the stiffness, K of the system by:

$$\omega_{nf} = \sqrt{\frac{K}{m}} \tag{13}$$

However the above frequency has to be modified since there is a mass in the form of an accelerometer at the free end of the continuous blanks. By continuous approach the solution is difficult since with tip mass the boundary condition at free end is now time dependent. A simpler approach will be to include the accelerometer mass in the total mass of the blank. A procedure for the calculating the first mode natural frequency by considering the total mass is illustrated below. With the total mass, $M_1$ (kg), the natural frequency could be measured as accurate as possible.

Considering the blank as a mass-less specimen with stiffness K and a discrete effective (concentrated) mass, $m_{ef}$ (kg/m) at the free end, produces the same frequency as a continuous blank specimen without any tip mass. Hence, the natural frequency of discrete model of the blank without an accelerometer can be written as:

$$\omega_{nf1} = \sqrt{\frac{K}{m_{ef1}}} \qquad (14)$$

Where the stiffness of the cantilever beam at it end is $$K = \frac{3EI}{L^3} \qquad (15)$$

"See T. Sakiyama and M. Huang, "Free vibration analysis of rectangular plates with variable thickness," *Journal of Sound and Vibration*, vol. 216, pp. 379-397, 1998 (reference), incorporated herein by reference in its entirety."

From which the effective mass m_eff1 at tip can be written by combining eqns. (14) and (15) as:

$$m_{ef1} = \frac{3EI}{\omega_{nf1}^2 L^3} \qquad (16)$$

Comparing eqn. (9) with eqn. (14), then the effective mass becomes:

$$m_{ef1} = \frac{3EI}{L^3} \frac{L^3 m}{1.875^4 EI} = \frac{33}{140} m \qquad (17)$$

Therefore, the effective mass at the tip of the blank is about 0.236 times the mass per unit length of the blank.

So, considering the mass of accelerometer, $m_a$, at the free end of the blank, the total mass at free end will be:

$$M_1 = m_{ef1} + m_a \qquad (18)$$

Hence, for the discrete blank with accelerometer, the theoretical fundamental natural frequency considering the mass of accelerometer will be:

$$\omega_{nf1} = \sqrt{\frac{K}{M_1}} \qquad (19)$$

Experimental Modal Analysis

The Components of the System Used for Data Acquisition and Data Processing

A. Data Acquisition Board NI 9234

NI 9234 is 4-channel dynamic signal acquisition (DSA) modules for making high-accuracy measurements from IEPE sensors. This C Series analog input module delivers 102 dB of dynamic range and incorporate IEPE (2 mA constant current) signal conditioning for accelerometers and microphones. The four input channels simultaneously acquire at rates from 2 to 50 kHz or, with the NI 9234, up to 51.2 kS/s. In addition, the modules include built-in antialiasing filters that automatically adjust to sampling rate. NI 9233/9234 modules are ideal for a wide variety of mobile/portable applications such as industrial machine condition monitoring and in-vehicle noise, vibration, and harshness testing. NI 9234 module use a method of A/D conversion known as delta-sigma modulation. If, for example, the data rate is 25 kS/s, then each ADC actually samples its input signal at 3.2 MS/s (128 times the data rate) and produces samples that are applied to a digital filter. This filter then expands the data to 24 bits, rejects signal components greater than 12.5 kHz (the Nyquist frequency), and digitally re-samples the data at the chosen data rate of 25 kS/s. This combination of analog and digital filtering provides an accurate representation of desirable signals while rejecting out-of-band signals. The built-in antialiasing filters automatically adjust themselves to discriminate between signals based on the frequency range, or bandwidth, of the signal.

B. Brüel & Kjær Impact Hammer—Type 8206

Type 8206 B & K impact hammer has been designed to excite and measure impact forces on small to medium structures such as engine blocks, car frames and automotive components. An accelerometer (or laser velocity transducer) is used to measure the response of the structure.

By using a multichannel fast Fourier transformation (FFT) analyzer, such as the PULSE™ system, the frequency response function and mode shapes of the test structure can then be derived. Contrary to using an electrodynamic exciter, an impact hammer does not apply additional mass loading to the test object and it provides a very portable solution for excitation. The output sensitivity is expressed in terms of voltage per unit force (mV/N or mV/lbf). The hammer also has built-in acceleration compensation that removes unwanted noise from the resonance of the hammer from the output signal. This results in a clean, smooth output signal representing the excitation in both amplitude and phase.

C. B & K Accelerometer Type—4371

The piezoelectric accelerometer converts the acceleration into an electric measure which is proportional with the force applied on the internal ceramic element (piezoelectric), the mechanic variable (acceleration) being obtained by a measurement of the force.

The assembly is composed of a central shaft, a ceramic piezoelectric element, a seismic body and a pre-load arrow. During operation, the unit sends a perpendicular movement towards the basis. When the accelerometer is attached to a vibrant structure, the seismic mass exacts a force on the ceramic piezoelectric element. This applied force determines the piezoelectric material to produce an electric measure. The force is equal to the mass multiplied by acceleration (Newton's second law: F=m*a), the result obtained is proportional to the acceleration as long as the mass m is constant.

D. B & K Charge Amplifier—Type 2635

Charge Amplifier Type 2635 is a comprehensively equipped charge conditioning amplifier. The output can be routed to portable tape recorders and level recorders, electronic voltmeters, measuring amplifiers and frequency analyzers. It can be powered from internal batteries or an external DC power supply, making it useful both in the field and in the laboratory. Other features of this amplifier are charge input, digit conditioning to transducer sensitivity, unified output ratings for simplified system calibration, high sensitivity up to 10V/pC, built-in integrators for displacement and velocity among others.

E. Computer System

The laptop PC with the configuration below was used as an interface where the other devices are linked to the labview software installed on the PC.

Figure 8:
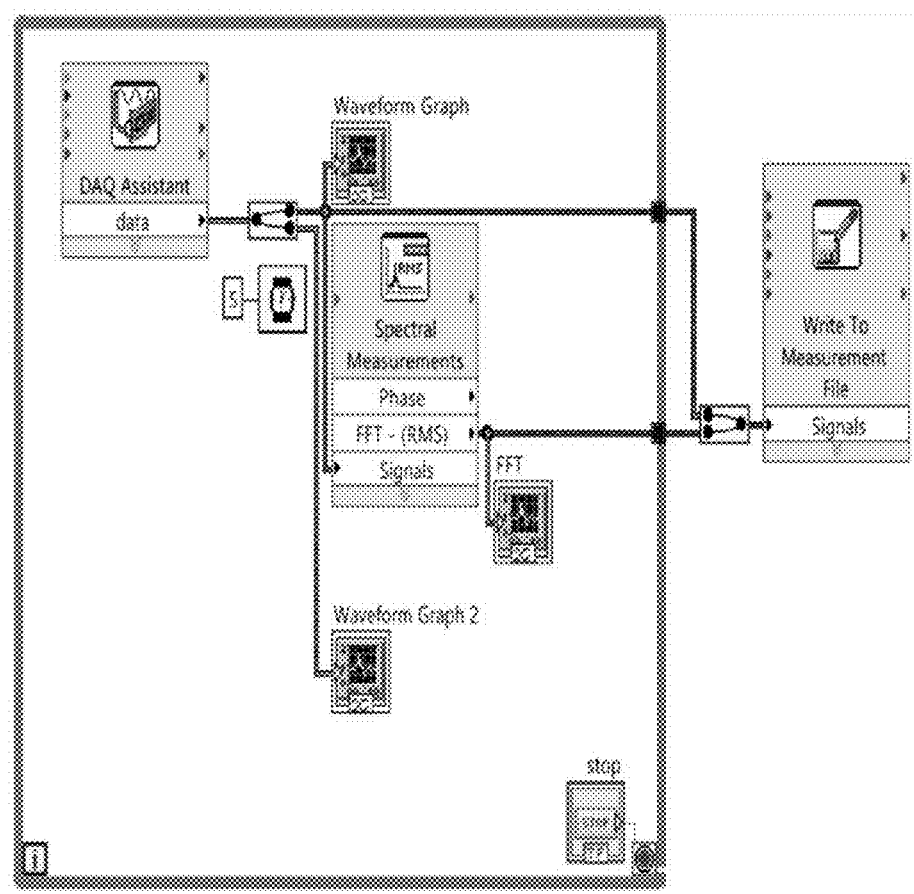
FIG. 8 is the block diagram of the virtual instrument achieved for data acquisition.

Brand: DELL, Inspiron N4030
CPU: Intel® Core™ i5 M480 @ 2.67 GHz 2.66 GHz
RAM: 3.00 GB (2.87 GB usable)
Weight: 2.1-2.5 kg
Screen Size: 14-14.5 in F. Labview Software In the processing of the acquired data through the medium of the acquisition board of the SCXI 1600 module the LabView development medium was used through which the used module was controlled with the help of the NI-DAQmx. The use of DAQ Assistant can simplify the development of the application. National Instruments recommends the creation of the tasks through the medium of DAQ Assistant at the use of sensors (paper cited in). In FIG. 8, the block diagram of the virtual instrument achieved for the proper acquisition of data is presented. The acquired data are written in a text file from which later they are read in order to be processed.

Figure 9:
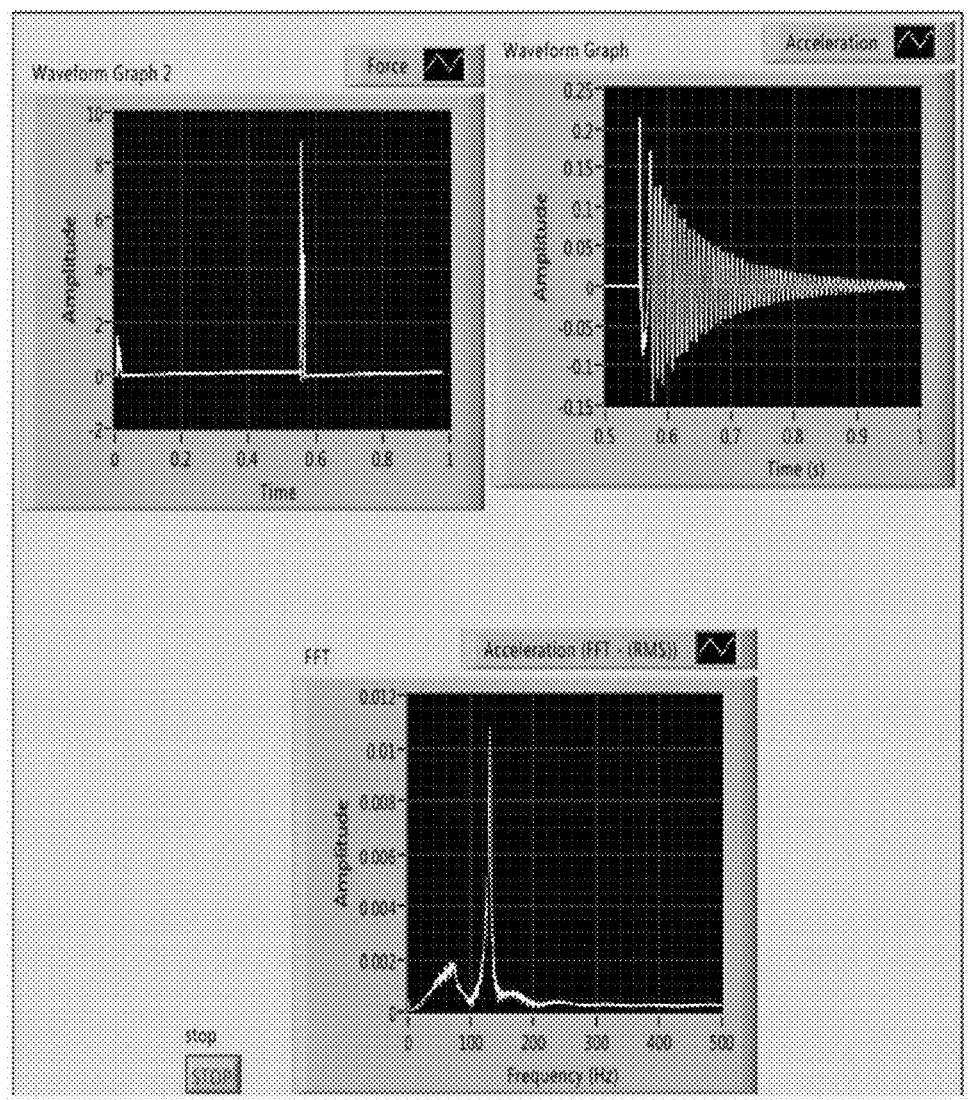
FIG. 9 is a window view of Labview software with three different plot displays.

The front panel of Labview software with three different plot displays is shown in FIG. 9. The input force (N) and output acceleration (in/sec 2) responses are shown on the top row of the main display. The frequency response function is shown on the bottom row of the main display. The frequency response function represents the ratio of output over input signals. The frequency response is a function of frequency and reaches its maximum value at natural frequency.

Figure 10:
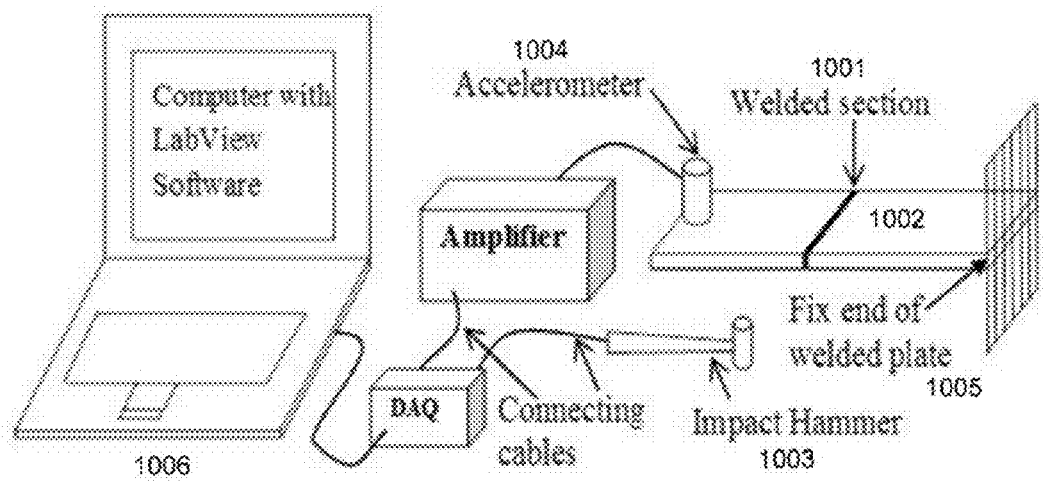
FIG. 10 is a schematic of modal analysis experimental set-up.

To obtain the natural frequency of the cantilever plate experimentally, a setup, as shown in the schematics in FIG. 10, was used. The impact hammer (Brüel & Kjær Impact Hammer—Type 8206) was used to set the sample into flexural motion. The accelerometer (B & K Accelerometer Type—4371) attached to the sample relays this flexural signal of the sample (due the impact) to the DAQ (Data Acquisition Board NI 9234) system which converts this analog signal to digital based signal. The signal from accelerometer was amplified by a charge amplifier (B & K Charge Amplifier—Type 2635) to increase the signal to noise ratio before reaching the DAQ. The DAQ's combination of analog and digital filtering provides an accurate representation of desirable signals. The filtered digital data is then transfer to the LabView software for further processing. The interfaced system (DAQ and virtual instruments—VIs) allows real time monitoring of the signals from the experimental setup. The time history (Displacement-Time), and Fast Fourier Transformation (FFT) plots of the data can be programmed in Labview software. The natural frequencies of the system were obtained directly by observing the FFT plot. The location of peak corresponds to the natural frequencies of the system.

The data acquisition system includes a data acquisition box (DAQ) and a host computer which displays the data in real-time and provides a graphical-user interface (Labview software).

Material Characterization

After welding, the samples were visually inspected then sectioned across the width parallel to welding direction to reduce the sample into a square like sample to ease further preparation for material characterization and mechanical testing.

Sample Preparation

These samples (square-like) were again sectioned transversely i.e. perpendicular to the welding direction resulting into two parts labeled X and Y for each sample. All samples (X of each sample only) were then hot-mounted using Buehler transoptic powder (polymer) in a mounting machine (Evolution, IPA 40 Remet, Bologna, Italy) at temperature of 200° C. for about 35 min including cooling time, to enable handling during grinding and polishing. The samples were then grinded using Buehler roll grinder (Handimet 2 Roll Grinder Buehler, Japan) with 240, 320, 400 and 600 grits and polished on Buehler grinding and polishing table until a mirror-like plane surface is achieved. The samples were sonicated for 10 min then etched with aqua *regia* solution (ratio HCl to $HNO_3$=3 to 1) for 3 to 4 minutes for microstructural micrograph imaging. Metallurgical optical microscope (MEIJI Techno MX7100, USA) was utilized to observe the shape and microstructure of the fusion zone. FIB-FESEM (LYRA3XM, Tescan, Germany) was also used to substantiate the images from optical microscope and to better understand the solidification nature and resulting microstructure during cooling across the heat affected and fusion zones. The Y section of each samples were prepared for X-Ray Diffraction (XRD).

A XRD D8 Advance (XRD D8Advance Bruker AXS, Germany) machine was used to reveal the interaction between the compositional elements of the material during welding and the resulting compound(s) formed at the fusion zone. For mechanical characterization, MMT-3 Digital Microhardness Tester, Buehler (Lake Bluff, Ill., USA) was used for the hardness scan across the welded region including the heat affected zone.

Example 2

Thermal Analysis

To determine the thermal field during the welding process, a thermal analysis is required, incorporating the moving heat source. The most significant factors affecting the analysis are the heat input rate, the moving speed of the heat source and the thickness of the plate material "See N. S. Shanmugam, Buvanashekaran, G., Sankaranarayanasamy, K., Ramesh Kumar, S., "A transient finite element simulation of the temperature and bead profiles of T-joint laser welds," *Materials & Design*, vol. 31, pp. 4528-4542, 2010 (reference), incorporated herein by reference in its entirety."

Heating Analysis

The fundamental behavior of heat conduction is that of a flux "See H. S. Carslaw and J. C. Jaeger, "Conduction of heat in solids," *Oxford: Clarendon Press*, 1959, 2nd ed., vol. 1, 1959 (reference), incorporated herein by reference in its entirety", q, of energy flows from a hot region to cooler regions, which is linearly dependent on the temperature gradient, (VT), i.e.:

$$q = -k\left(\frac{\partial T}{\partial x} + \frac{\partial T}{\partial y} + \frac{\partial T}{\partial z}\right) \qquad (20)$$

Where k is the thermal conductivity and it should be noted that the minus sign is necessary in order to keep q positive. The energy required to change the temperature of the materials is defined by specific heat $c_p$ or enthalpy H. The conservation of energy is expressed in a differential form having the terms for specific heat, thermal flux and a distributed volume heat-source term $S_0$ (W/m³) and it is given as:

$$\rho c_p \partial T/\partial t - \nabla(k\nabla T) - S_0 = 0 \quad (21)$$

where t is the time parameter and p is the density of the material.

The thermal boundary conditions at all surfaces of the plate are assumed to be the same for the numerical simulation. Convection and radiation losses from the surfaces are considered and the heat transfer coefficients h are divided to include radiation and convection effects. Given a body temperature T, radiation to the surrounding medium at the temperature $T_0$ follows the Stefan-Boltzmann law, so the resulting temperature difference causes a flux (power loss) defined as:

$$\dot{q}_{rad} = \sigma\varepsilon(T^4 - T_0^4) \quad (22)$$
$$= \sigma\varepsilon(T^2 + T_0^2)(T + T_0)(T - T_0) \quad (23)$$
$$= h_{rad}(T - T_0) \quad (24)$$

Where (25)
$$h_{rad} = \sigma\varepsilon(T^2 + T_0^2)(T + T_0)$$

Where $\varepsilon$ is the emissivity, $\sigma$ is the Stefan-Boltzmann constant and $h_{rad}$ is the resulting temperature dependent heat transfer coefficient for radiation. Given a body with temperature T, surrounded by a fluid or gas at temperature $T_0$, heat convection assumes that a thermal layer exists with the heat transfer coefficient $h_{com}$, so the resulting temperature difference across the boundary layer causes a flux, $\dot{q}_{conv}$, given by $$\dot{q}\_conv = h_{conv}(T - T_0) \quad (26)$$

where $h_{conv}$ is the heat transfer coefficient for convection (W/m²K), $\sigma$ is the Stefan-Boltzmann constant for radiation (5.67×10⁻⁸ W/m²K⁴), E is the emissivity, T is ambient temperature (K). Initially the sample material is assumed to be at a reference temperature, $T_0$, hence, the initial condition is T=$T_0$ at t=0

Figure 12:
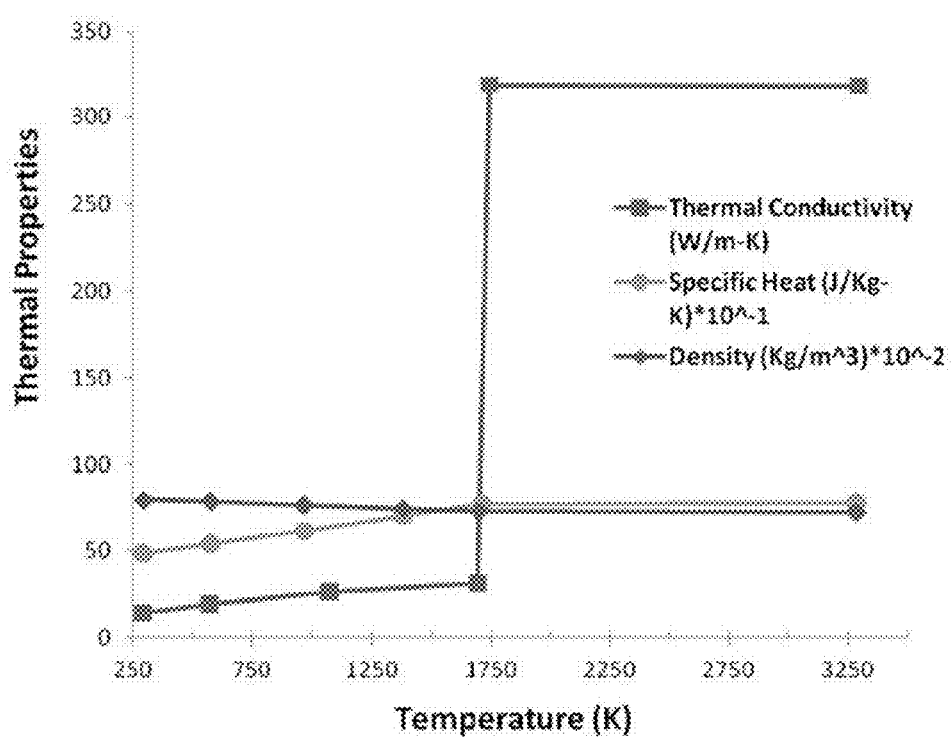
FIG. 12 is a graph of AISI 316L Temperature Dependent Thermal Material Properties.
Figure 13:
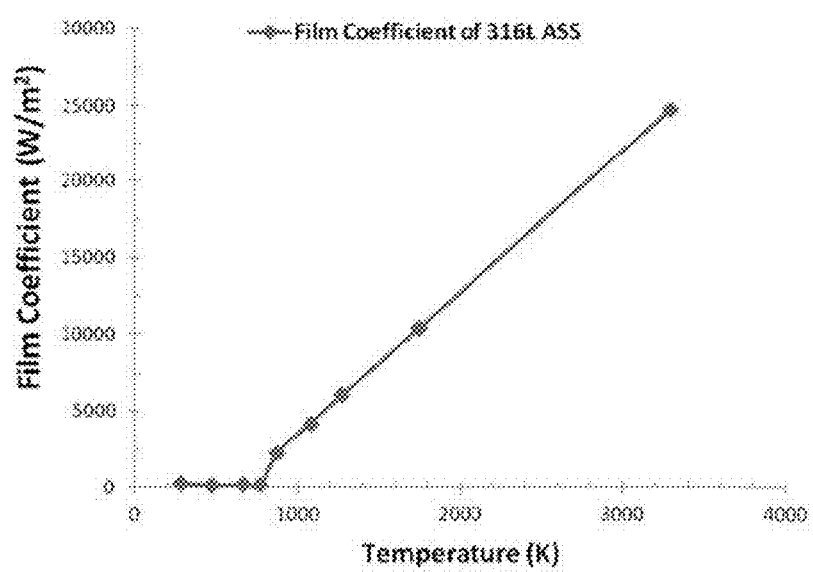
FIG. 13 is a graph of film Coefficient of 316L ASS.
Figure 14A:
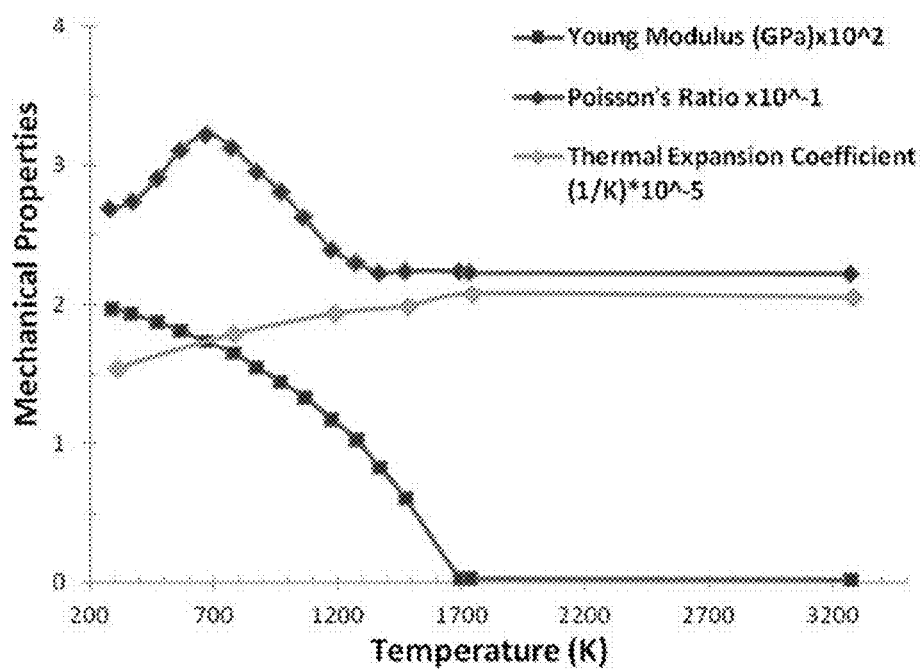
FIG. 14A is a graph of a AISI 316L Temperature Dependent Mechanical Material Properties.
Figure 14B:
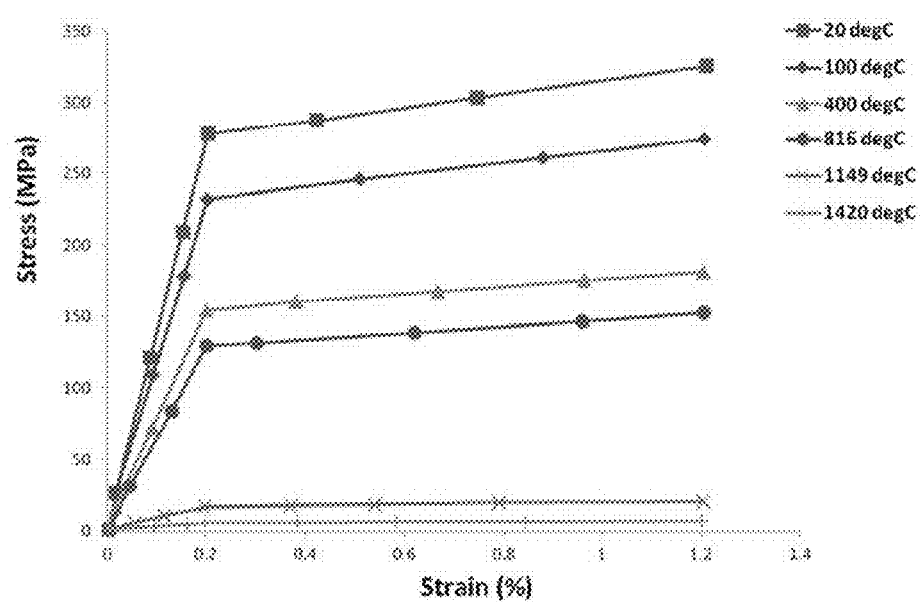
FIG. 14B is a graph of 316L Stress-Strain Curves.

However, the convection heat transfer coefficient incorporating emissivity as proposed by Frewin and Scott is used in this analysis given by Eqn. (27). The temperature dependent thermal and mechanical properties of the 316L steel blanks are given in FIG. 12 and FIG. 14 respectively. The film coefficient of 316L ASS is depicted in FIG. 13.

$$h_{conv} = 2.4 \times 10^{-3} \varepsilon T^{1.61} \quad (27)$$

Figure 11:
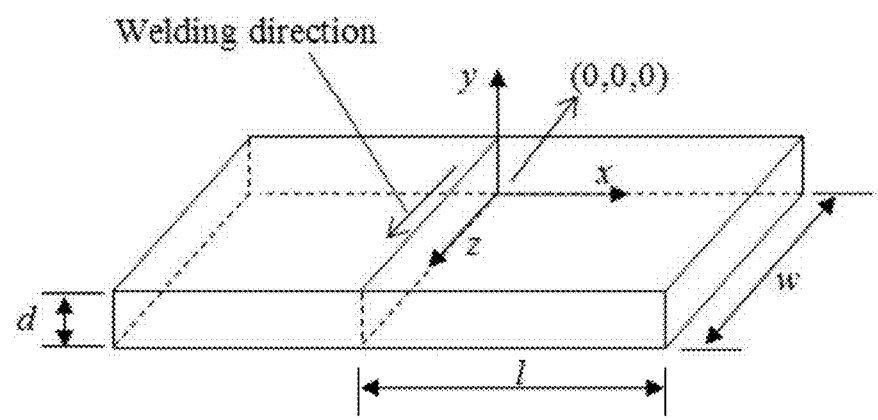
FIG. 11 is a schematic diagram of the Simulation model and coordinates.
Figure 15:
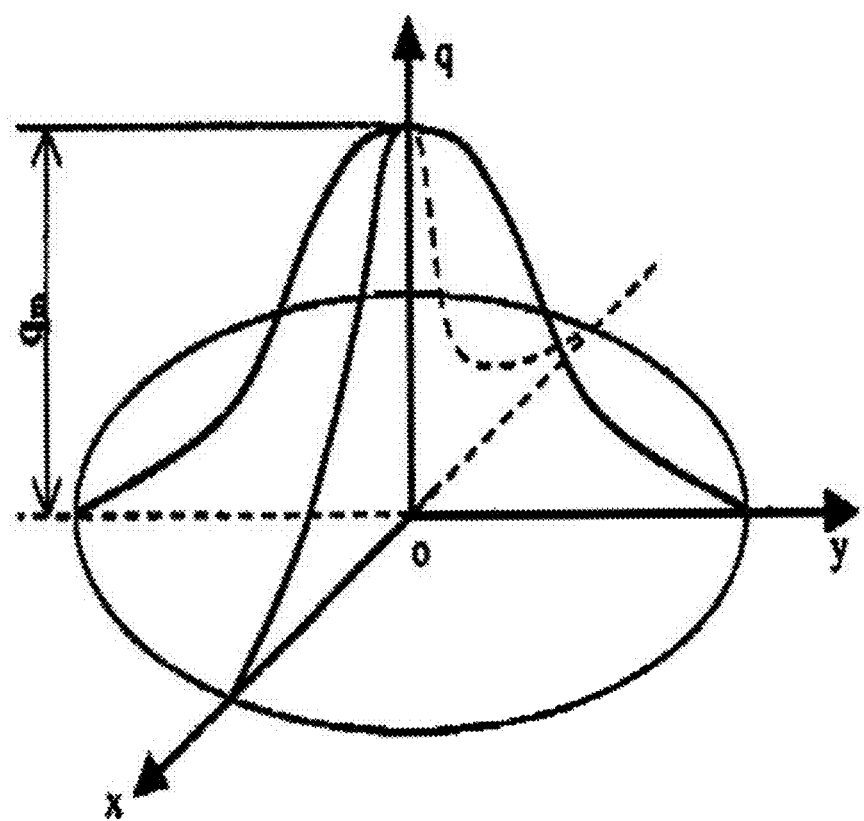
FIG. 15 is a schematic of Gaussian distribution of heat intensity.
Figure 16:
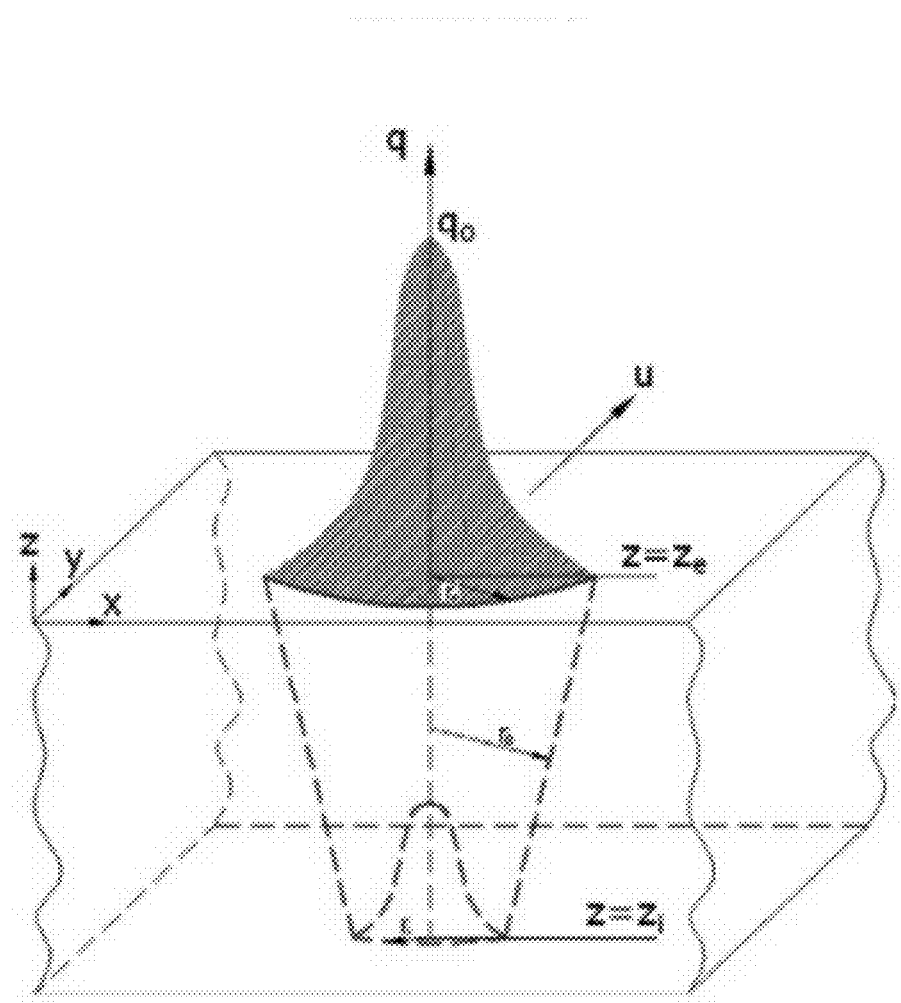
FIG. 16 is a schematic of 3D Conical Gaussian distribution of heat source.

FIG. 11 shows the schematic diagram of the simulation model and coordinates. The following thermal boundary conditions were applied to the surfaces:
At x=±l, y=0, z=w:
$\dot{q}_{conv}$ and $\dot{q}_{rad}$ at the surfaces are considered
At x=±l, y=d and z=0:
$\dot{q}_{conv}$ and $\dot{q}_{rad}$ at the surfaces are considered
At x=±l, y=0 and z=w:
$\dot{q}_{conv}$ and $\dot{q}_{rad}$ at the surfaces are considered
At x=±l, y=d and z=w:
$\dot{q}_{conv}$ and $\dot{q}_{rad}$ at the surfaces are considered
At x=0, y=d and z=w:
$\dot{q}_{conv}$ and $\dot{q}_{rad}$ at the surfaces are considered
Heat Source Model Researchers have employed different heat source models; the Gaussian distribution of heat flux (W/m²) deposited on the surface of the workpiece as shown in FIG. 15, 3D conical Gaussian profile as shown in FIG. 16 and the double-ellipsoidal heat source model (FIG. 17) "See A. Trivedi and P. Chauhan, "Modeling of Welding Heat Source for Laser Spot Welding Process," 2011 (reference); "See A. De, S. K. Maiti, C. A. Walsh, and H. Bhadeshia, "Finite element simulation of laser spot welding," *Science and Technology of Welding & Joining*, vol. 8, pp. 377-384, 2003 (reference); and "See A. Malik, M. Ejaz, and N. Ullah, "Numerical Simulation of Arc Welding Investigation of various Process and Heat Source Parameters," *Failure of Engineering Materials & Structures, Code*, vol. 30, 2007 (reference), each incorporated herein by reference in their entirety." A recent study concentrated on the modification of these heat source model to accurately account for the physical phenomenon "See C. S. Wu, H. G. Wang, and Y. M. Zhang, "A new heat source model for keyhole plasma arc welding in FEM analysis of the temperature profile," *WELDING JOURNAL-NEW YORK-*, vol. 85, p. 284, 2006 (reference), incorporated herein by reference in its entirety." In this study, the double ellipsoidal heat source model was used due to its capability of simulating laser beam welding on a thin plate "See D. Berglund, A. Lundbäck, and L. E. Lindgren, "Three-dimensional finite element simulation of laser welded stainless steel plate. NUMIFORM'01," in *Proc. 17th International Conference on Numerical Methods in Industrial Forming Processes*, 2001, pp. 1119-1123 (reference); and "See A. Lundbäck, "CAD Support for heat input in a FE model," *BOOK-INSTITUTE OF MATERIALS*, vol. 784, pp. 1113-1122, 2002 (reference), each incorporated herein by reference in their entirety."

Definition of the Double Ellipsoid Heat Source Model

The double ellipsoidal heat source model entails two dissimilar power sources of the same geometrical shapes but of different dimensions. These two different components of the model define the front and the rear of the heat source, respectively. The mathematical equation that describes the front of the heat source models its steep shape, resulting from the movement of the heat source while that of the rear heat source is adapted to the smooth gradients of the heat flux "See A. P. Kyriakongonas and V. J. Papazoglou, "3D numerical model of austenitic stainless steel 316L multipass butt welding and comparison with experimental results," *Analysis and design of marine structures*, vol. 1, p. 371, 2009 (reference), incorporated herein by reference in its entirety." In essence, the heat source is a combination of two different semi-ellipsoids described by separate equations:

For a point (x, y, z) in the front semi-ellipsoid of the model, the governing equation of the power density (W/m³) is:

$$Q_f(x, y, z) = \frac{6\sqrt{3} f_f Q}{a_f bc\pi^{3/2}} \exp\left(\frac{-3x^2}{a_f^2}\right) \exp\left(\frac{-3y^2}{b^2}\right) \exp\left(\frac{-3z^2}{c^2}\right) \quad (27a)$$

Figure 17:
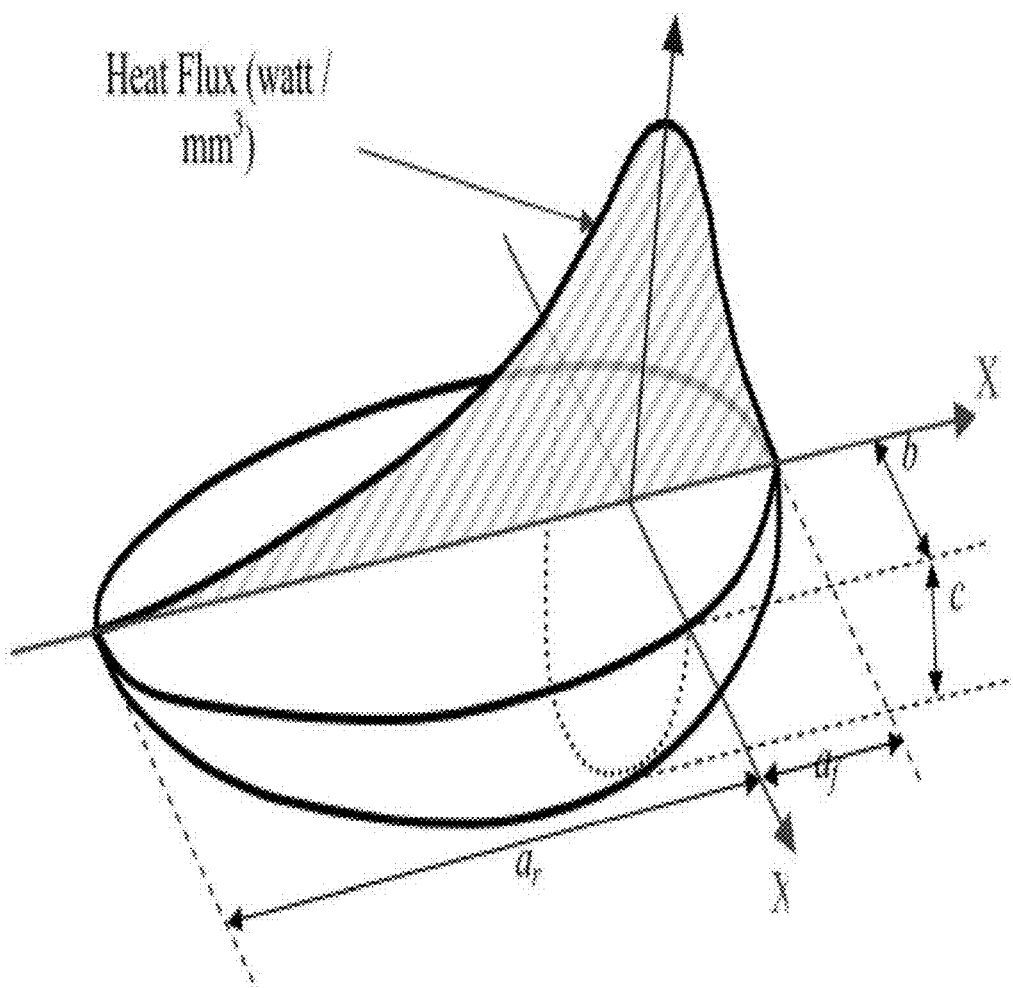
FIG. 17 is a schematic of Double Ellipsoidal representation of the heat source.

While for a point in the rear semi-ellipsoid model, the heat flux is described as:

$$Q_r(x, y, z) = \frac{6\sqrt{3} f_r Q}{a_r bc\pi^{3/2}} \exp\left(\frac{-3x^2}{a_r^2}\right) \exp\left(\frac{-3y^2}{b^2}\right) \exp\left(\frac{-3z^2}{c^2}\right) \quad (27b)$$

Where $a_f$, $a_r$, b and c are the ellipsoid heat source geometric parameters as shown in FIG. 17. Q is the laser beam power (W) which includes the efficiency of the beam power reaching at the surface. The parameters $f_f$ and $f_r$ are proportion coefficients representing heat apportionment in front and back of the heat source respectively. The sum of the fractions ($f_f$ & $f_r$) between the heat deposited in front and rear quadrant must equal two, that is:

$$f_f + f_r = 2 \tag{28a}$$

For the condition of continuity of the overall volumetric het source in equations 27a and 27b when x=0 the following condition for coefficient must be satisfied:

$$f_f = \frac{2a_f}{a_f + a_r} \tag{28b}$$

$$f_r = \frac{2a_r}{a_f + a_r} \tag{28c}$$

or

Geometry of the Finite Element Model

Figure 18:
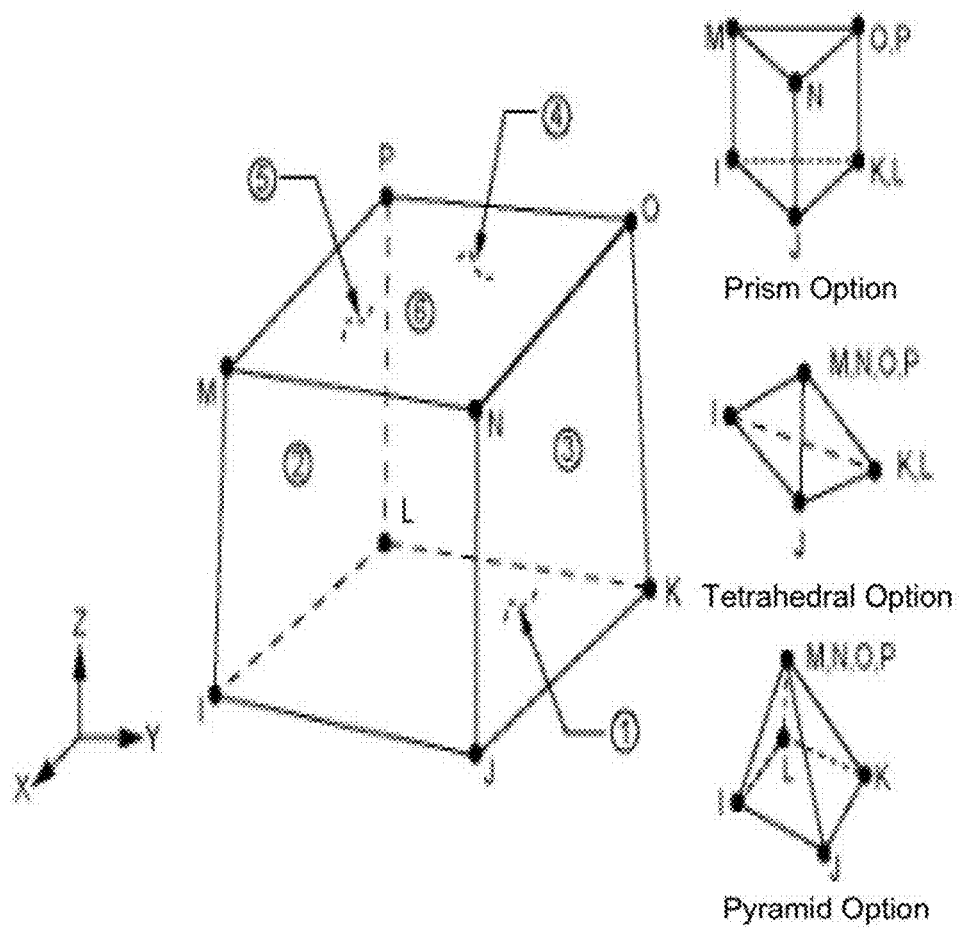
FIG. 18 is a schematic of Geometry of Solid 70.
Figure 19A:
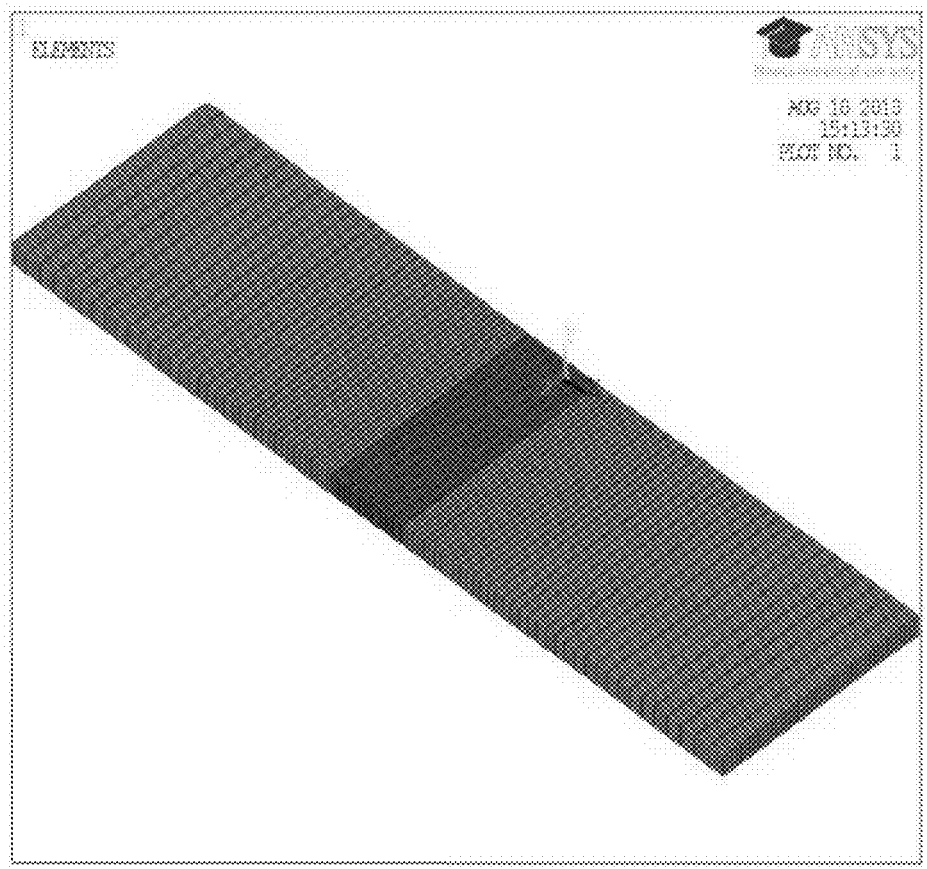
FIG. 19A is a schematic of Finite Element model 1.5.
Figure 19B:
FIG. 19B is a schematic of Finite Element model 2.
Figure 19C:
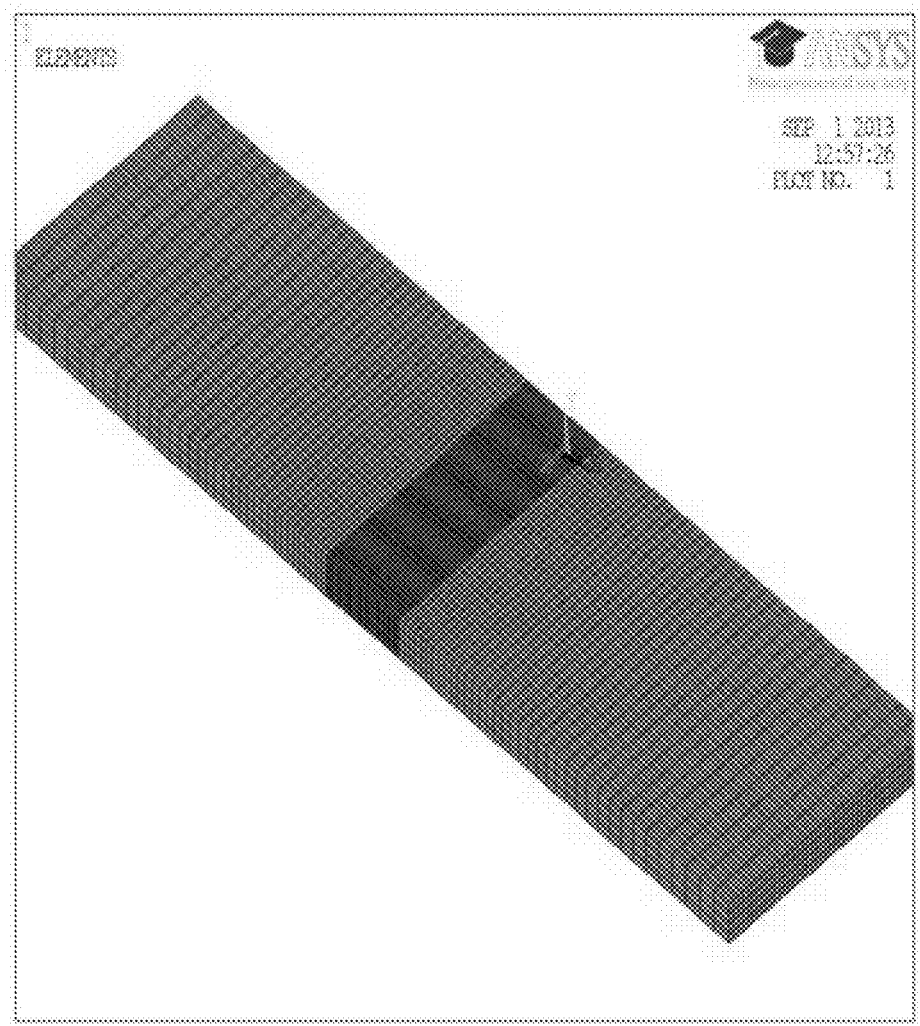
FIG. 19C is a schematic of Finite Element model 2.5.
Figure 19D:
FIG. 19D is a schematic of Finite Element model 3.

The element chosen for the analysis is SOLID 70. It has 3D thermal conduction capability for three dimensional steady-state or transient thermal analysis. The element has eight nodes with a single degree of freedom; temperature, at each node. The element also can compensate for mass transport heat flow from a constant velocity field. The geometry of solid 70 is shown in FIG. 18.

The FE models are shown in FIG. 19A-D. Table 7 shows the number of finite elements and nodes for each FE model considered in this study. This number of elements and nodes were chosen after conducting the mesh independency test (mesh convergence test) in order to reduce the simulation run-time while maintaining its accuracy. The smallest element used in the FEA model is in the welded zone and has the dimension of 0.2 mm×0.5 mm×0.375 mm, 0.2 mm×0.5 mm×0.5 mm, 0.2 mm×0.5 mm×0.625 mm and 0.2 mm×0.5 mm×0.75 mm for model 1.5, 2, 2.5, and 3 respectively and they gradually increase in size away from the weld region. Along the thickness direction four (4) elements were used in all the FE models. The size and type of the element are crucial to obtain accuracy of the result and reduction of solution time required for finite element analysis.

TABLE 7

Number of Elements and Nodes of FE Models

| FE Model | Number of Elements |
| --- | --- |
| 1.5 | 19712 |
| 2 | 21320 |
| 2.5 | 22880 |
| 3 | 22880 |

Structural Analysis

The FEM structural analysis carried out use the sequential thermal-stress solution procedure in which the transient thermal analysis is followed by the thermal stress analysis. Resulted temperatures distributions from the thermal analysis were used as loading for the thermal stress analysis. This means that at the end of the thermal analysis, all nodal thermal results, for every time-step, were written in the result file and inputted as the body load in the structural analysis. In a coupled field analysis, the accuracy of the structural analysis is rested on the correctness thermal analysis results, however the following important procedures must be implemented to achieve reliable structural results:

1. Must ensure geometrical compatibility by adopting the same FEM model and mesh used during thermal analysis for the structural part
2. A corresponding thermal element type must be used for the structural analysis.
3. Mechanical temperature dependent properties must be used and the optional deletion of the thermal properties, in order to free the solver unnecessary information
4. The transient structural analysis must be exactly the same with the transient thermal analysis, meaning that the exact number of time steps and time intervals must be used for both analyses in order to avoid confusion and erroneous results.
5. For each time step, the load is read from the thermal result file and inputted as body load in the structural analysis.

Also, Zhu and Chao "See X. K. Zhu and Y. J. Chao, "Effects of temperature-dependent material properties on welding simulation," *Computers & Structures*, vol. 80, pp. 967-976, 2002 (reference), incorporated herein by reference in its entirety" has indicated that the yield stresses at all temperatures are the most important parameter in welding simulation and that its value has significant effect on the residual stress.

The element type used in the current structural analysis is the ANSYS® SOLID185 element which is the corresponding element type for the thermal element type used. The temperature-dependent mechanical properties of 316L ASS was presented in FIG. 14($a$) and the Stress-Strain curves in FIG. 14($b$) from which the yield stresses where obtained. To effectively stimulate the phase change, temperature-dependent enthalpy reported here were used.

During the welding process, because solid-state phase transformation does not occur in the stainless base metal and the weld metal, the total strain rate can be decomposed into three components as follows "See D. Deng and H. Murakawa, "Numerical simulation of temperature field and residual stress in multi-pass welds in stainless steel pipe and comparison with experimental measurements," *Computational Materials Science*, vol. 37, pp. 269-277, 2006 (reference), incorporated herein by reference in its entirety":

$$\dot{\epsilon} = \dot{\epsilon}^e + \dot{\epsilon}^p + \dot{\epsilon}^{th} \tag{29}$$

Where the components on the right side of Equation (29) are the elastic strain, plastic strain and thermal strain respectively. The elastic strain is modeled using the isotropic Hook's law with temperature-dependent Young's modulus and Poisson's ratio. The thermal strain is computed using the temperature-dependent coefficient of thermal expansion. For the plastic strain, rate-independent plastic model is used with the following characteristics: the Von Mises yield criterion, temperature-dependent mechanical properties, and bilinear Isotropic (BISO) hardening model.

Example 3

Results and Discussion

Modal Analysis

Figure 20:
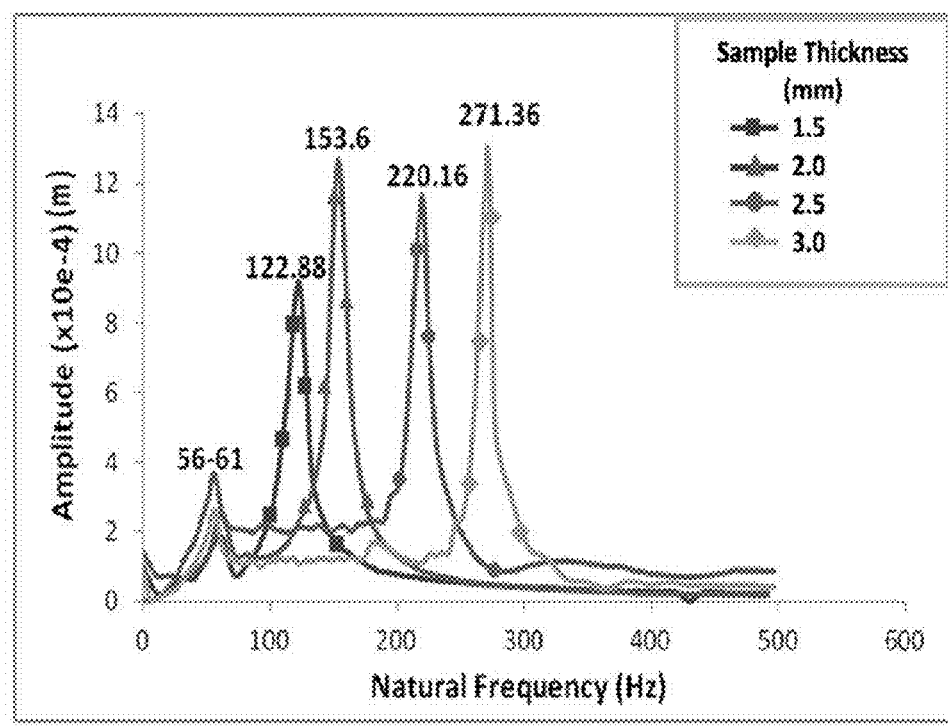
FIG. 20 is a graph of Natural Frequency of non-welded samples of different thickness.

The experimental set-up which consists of an interface between the data acquisition system and software package for signal processing—labVIEW 2011 SP1, was used to acquire the natural frequency of 316L steel blank samples. FIG. 20 shows a set of the results obtained from modal testing using the data acquisition interfaced with the software package for "as received" (non-welded) samples.

Peaks due to electrical noise where within the frequency range of 56-61 Hz for all samples investigated. This is the electrical frequency of AC powered devices used during the experiment. The results indicate that as the sample thickness increases the obtained natural frequency also increases. This follows the fact that a large plate thickness increases the moment of inertia of the plate which in turn increases the resistance of the plate to flexure thereby increasing the natural frequency of the as received plate.

Figure 21:
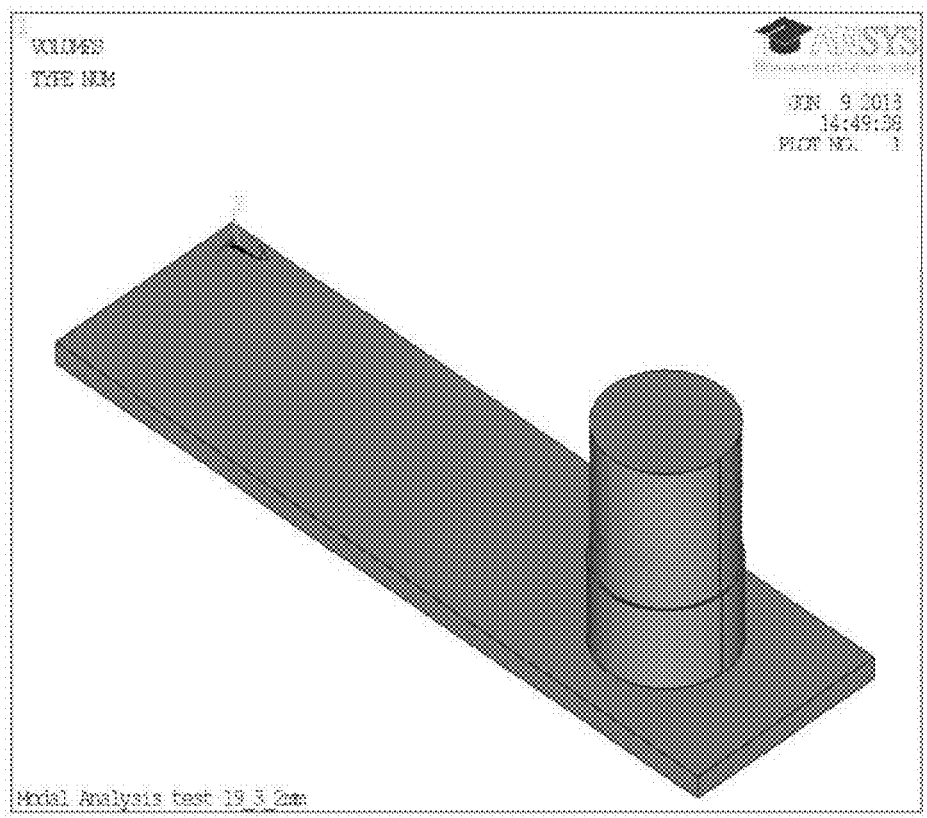
FIG. 21 is a geometrical model of non-welded sample and accelerometer.
Figure 22A:
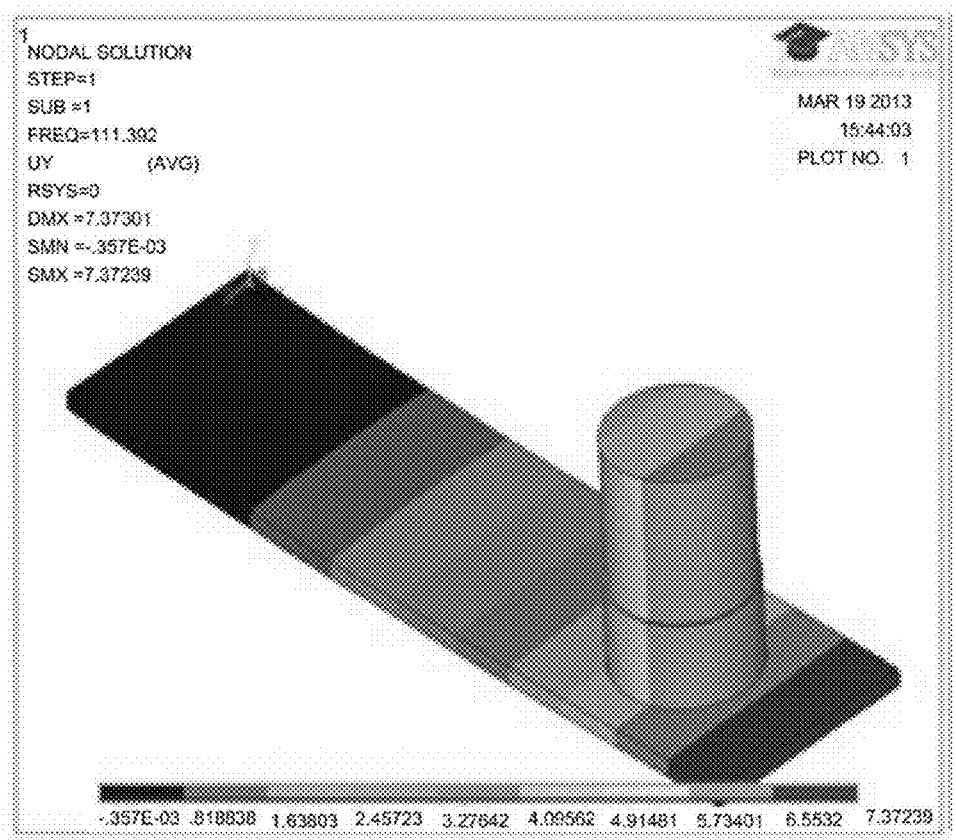
FIG. 22A is a numerical plot of the Natural Frequency of non-welded samples with a sample thickness of 1.5 mm.
Figure 22B:
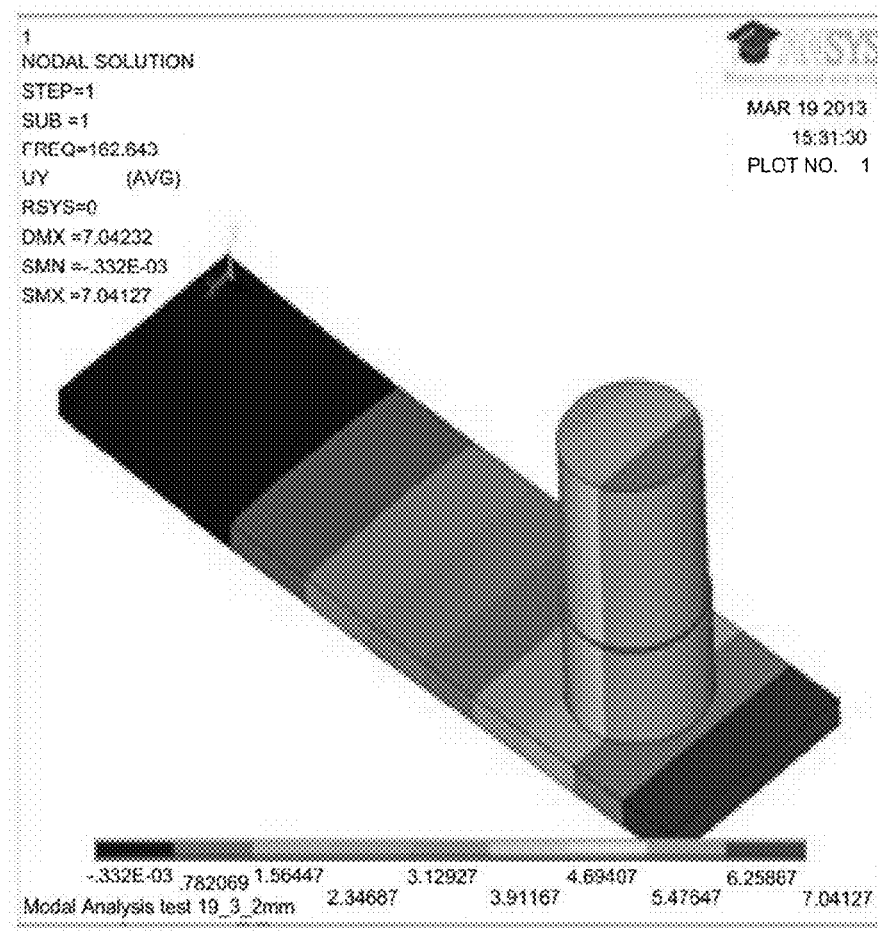
FIG. 22B is a numerical plot of the Natural Frequency of non-welded samples with a sample thickness of 2 mm
Figure 22C:
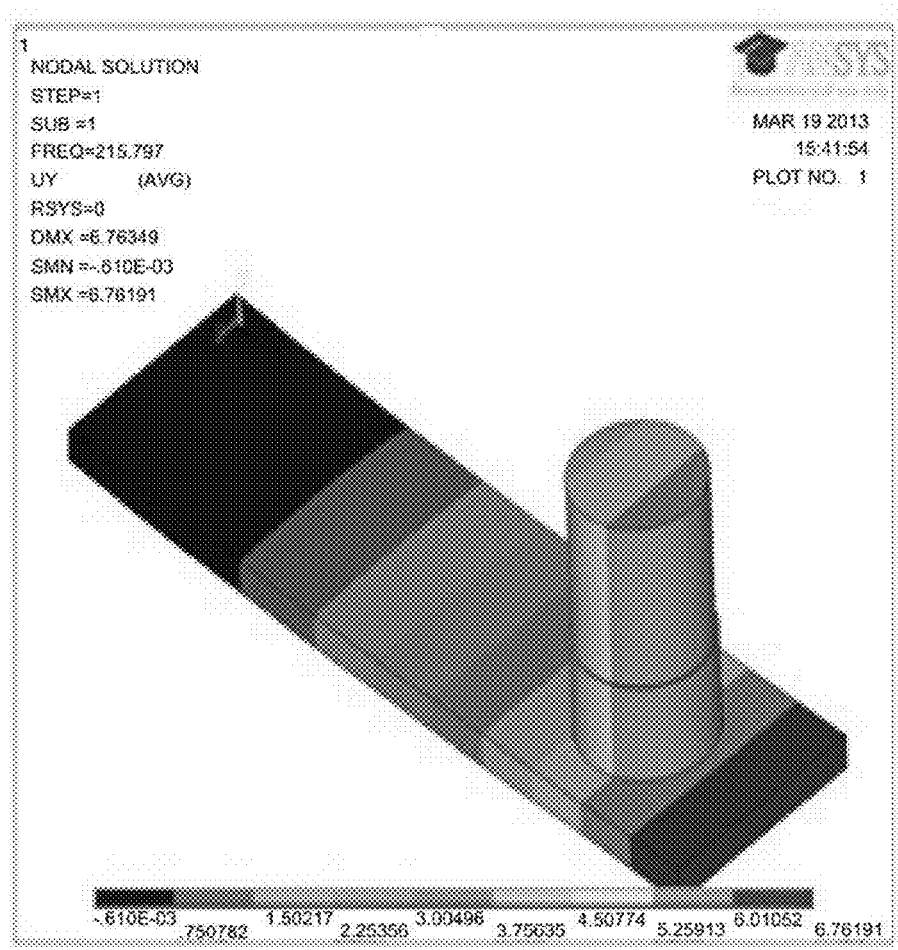
FIG. 22C is a numerical plot of the Natural Frequency of non-welded samples with a sample thickness of 2.5 mm.
Figure 22D:
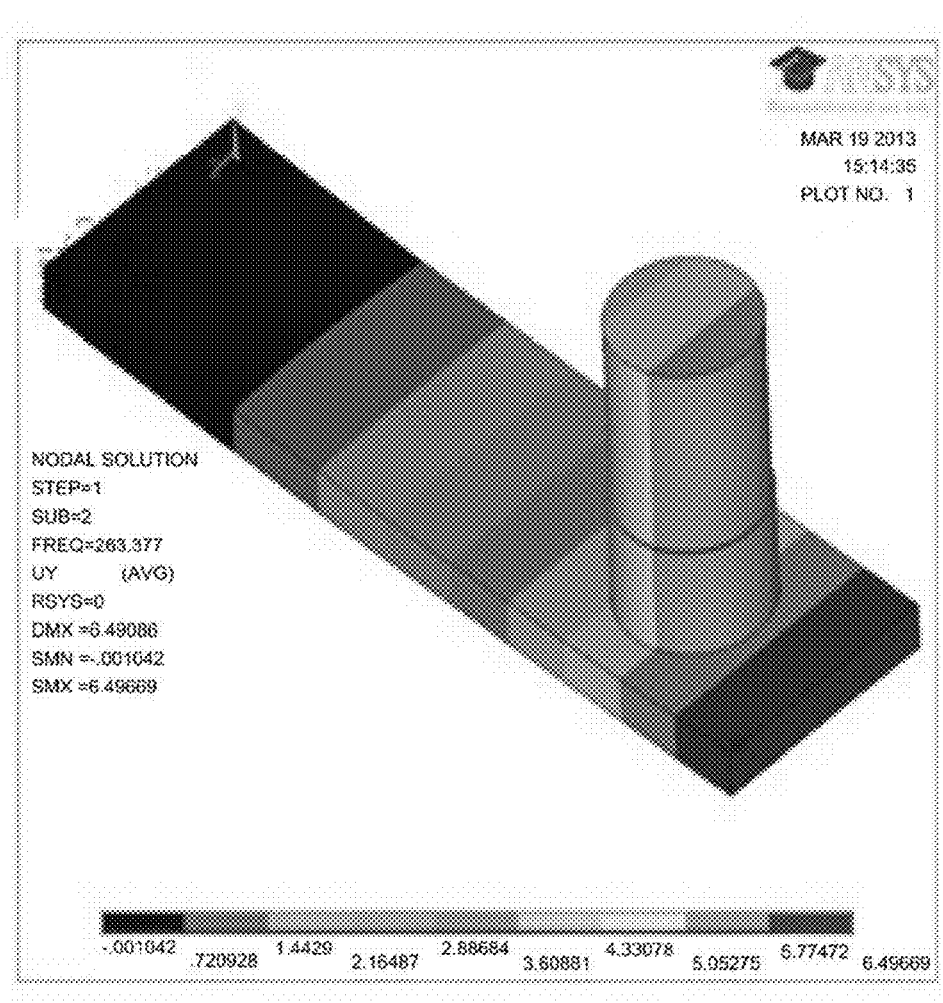
FIG. 22D is a numerical plot of the Natural Frequency of non-welded samples with a sample thickness of 3 mm.

To validate the FFT results obtained from labVIEW 2011 SP1 which the natural frequencies are read from, comparisons is made with numerical results. Numerical modeling of the modal analysis was conducted using the FEM ANSYS software code for the same geometry of the "as received" 316L steel plates. Since the natural frequency of a system is influenced by the geometry and is more or less an extrinsic properties, the effect of the attached accelerometer at the free end of the plates needs to be considered during the simulation. Because of this, the FE model of the accelerometer was incorporated in the model of the tested sample as shown in FIG. 21. Ansys finite element Solid 5 which is a 3-D element with eight nodes and up to six degrees of freedom with thermal and structural capability. A total of 197,107 elements were used, this number of elements satisfy the mesh independency test at reasonably computational time. FIG. 22A-D shows the natural frequency plots from numerical modeling of non-welded plates for different sample thicknesses. It was found that the natural frequency increases as the thickness of the sample increases while the deflection decreases from 7.5 to 6.5 mm as the thickness of the sample increase from 1.5 to 3 mm respectively. This behavior is linked to the direct influence of sample thickness on the moment of inertia of the plate, which causes the flexure resistance of the system to rise and thereby increasing the natural frequency.

Figure 23:
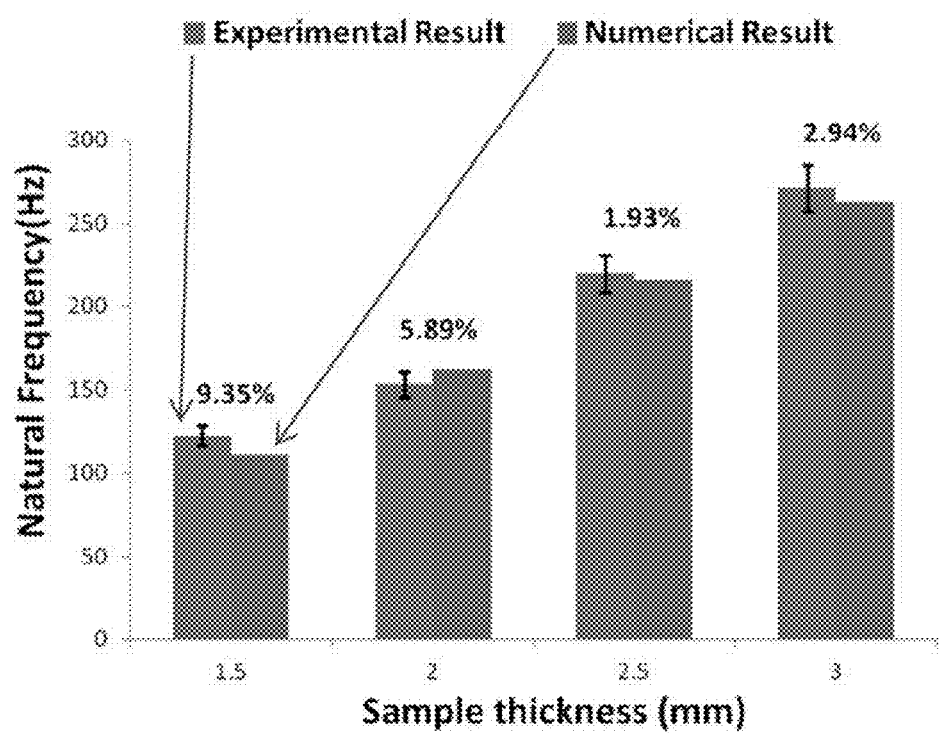
FIG. 23 is a graph of the comparison of the Natural frequency of modal test and numerical results of non-welded Samples.

Therefore, larger sample thickness indicates higher natural frequency due to the subsequent effect of the sample thickness on the inertia of the system. Several readings of the modal testing of these samples were averaged to compare with results obtained numerically. Table 8 shows the comparison with 9.65% maximum percent difference for the 1.5 mm thick blank. The comparison and variation are clearly shown in FIG. 23. These differences are still within acceptable range to conclude that the numerical results are in agreement with the results acquired from the experimental test. Hence welded samples with different parameters as shown in tables 3 through 6 are then investigated.

Figure 24:
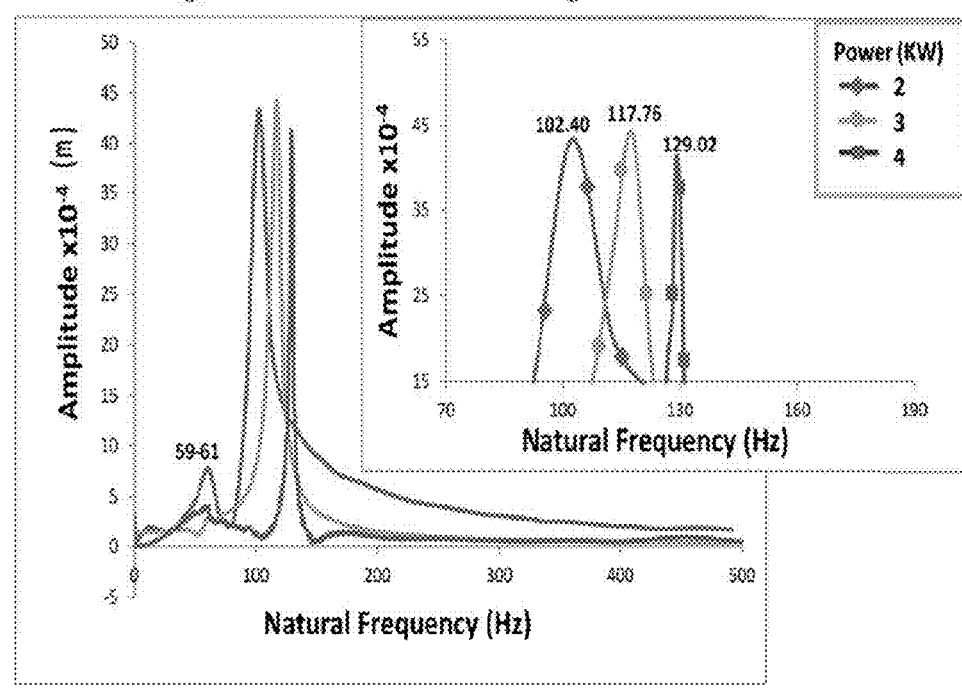
FIG. 24A is a graph of Natural Frequency of 1.5 mm thick samples welded with 400 mm/min using different Beam Power.
FIG. 24B is an expanded view of FIG. 24A.
Figure 25:
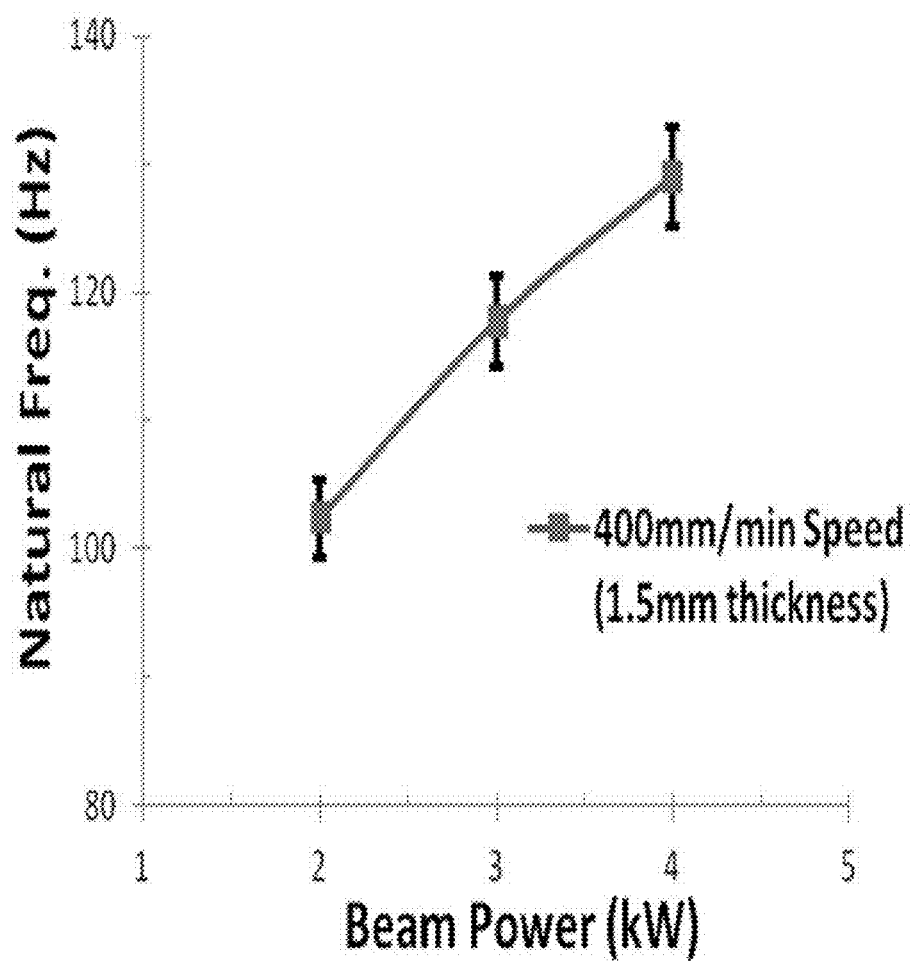
FIG. 25 is a graph of Natural Frequency variation with Beam Power.

FIG. 24 shows the natural frequency peaks of a welded sample using different beam power while other welding parameters are kept constant (see table 5). It was noticed that the natural frequency of the welded samples are similar to that of the non-welded sample of the same thickness. This is an indication of defect-free weld and less distortion of welded region accompanying laser welding process. It was also observed that the natural frequency increases as the laser beam power increases as shown in FIG. 25 in which variation of the natural frequency as a factor of the beam power is shown. This behavior is associated with the fact that as the beam power increases, the coarser the microstructure becomes "See A.-M. El-Batahgy, "Laser Beam Welding of Austenitic Stainless Steels—Similar Butt and Dissimilar Lap Joints," *INTECH Open Science Open Minds*, pp. 93-116, 2012 (reference), incorporated herein by reference in its entirety", and the more coarse the microstructure of a material is, the more easily deforming the material becomes. This results in large grains and less grain boundaries that aid in hindering deformation.

Figure 26:
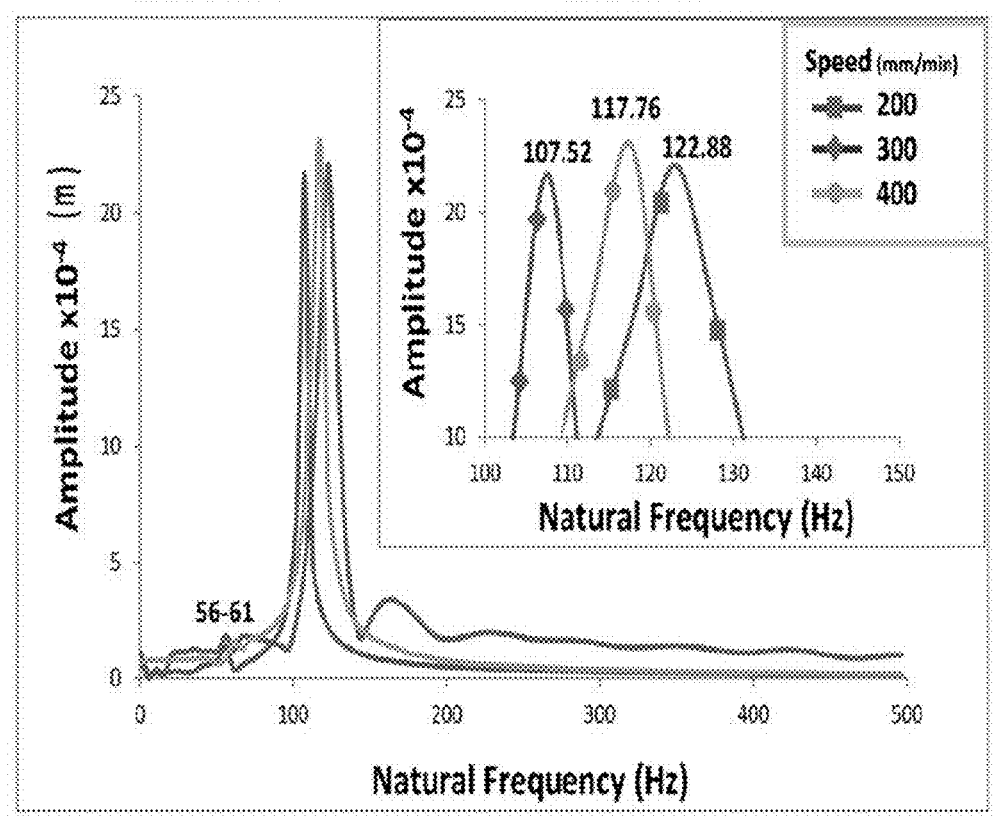
FIG. 26A is a graph of Natural Frequency of 1.5 mm thick samples welded with 3 KW using different feed rates (welding speed).
FIG. 26B is an expanded view of FIG. 26A.
Figure 27:
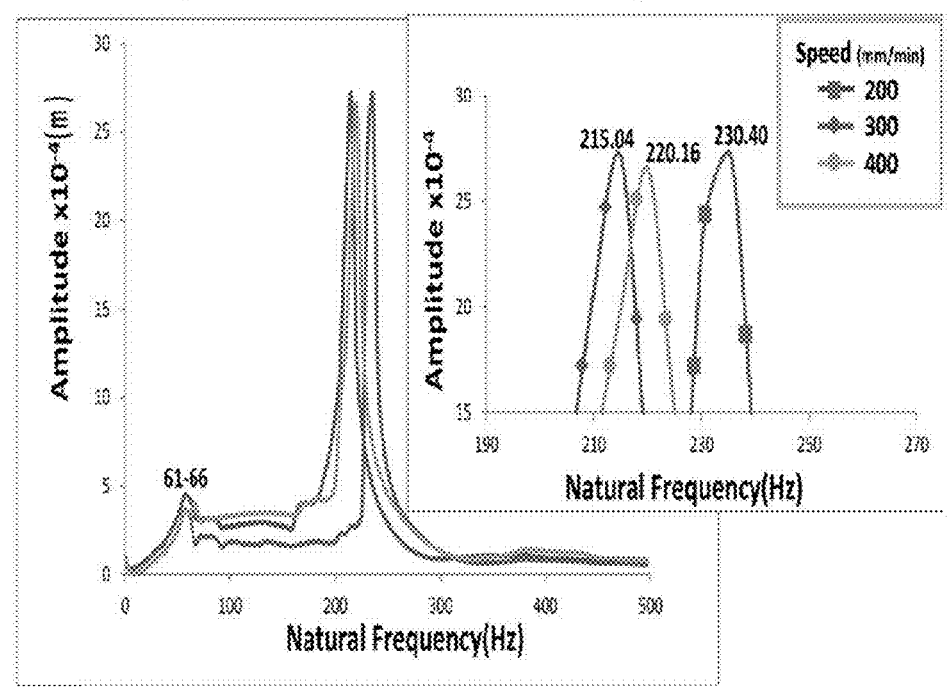
FIG. 27A is a graph of Natural Frequency of 2.5 mm thick samples welded with 4 KW using different feed rate (welding speed).
FIG. 27B is an expanded view of FIG. 27A.
Figure 28:
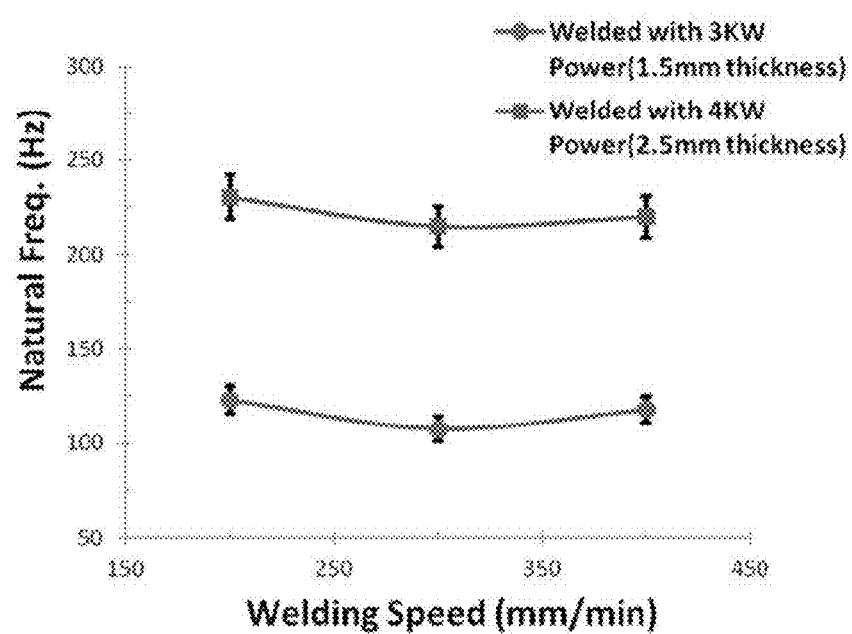
FIG. 28 is a graph of Natural Frequency variation with welding speed.

Effects of welding speed (feed rate) of the beam on the natural frequency peaks are shown in FIG. 26. It was found that at a lower feed rate (200 mm/min) the natural frequency is 122.88 Hz. An increase in the welding speed (feed rate) to 300 mm/min resulted in a decrease of the natural frequency (107.52 Hz). Accordingly, El-Batahgy reports that the higher the welding speed, the finer the microstructure. This is attributed to an increase in both solidification and cooling rates due to the low heat input that results from a higher welding speed. Fine microstructure indicates more resistance to deformation and increased material stiffness, hence the lower natural frequency. A similar trend was also observed as shown in FIG. 27 where a different set of parameters were investigated. This seems to be true for first two results but on further increase in the weeding speed the natural frequency increased rather than decrease as expected. A further increase of the welding speed to 400 mm/min resulted in a natural frequency of 117.76 Hz. This behavior can be attributed to the fact that at a higher welding speed attenuation of beam energy by plasma is less significant. This results in relatively more exposure of the laser beam on the sample which in turn increases the heat dissipation on the workpiece. It is also worth mentioning that natural frequency is again within the range of the non-welded sample of same thickness indicating the absence of distortions and defect-free welds. These variations of frequency with welding speed are illustrated in FIG. 28 for both cases.

Figure 29A:
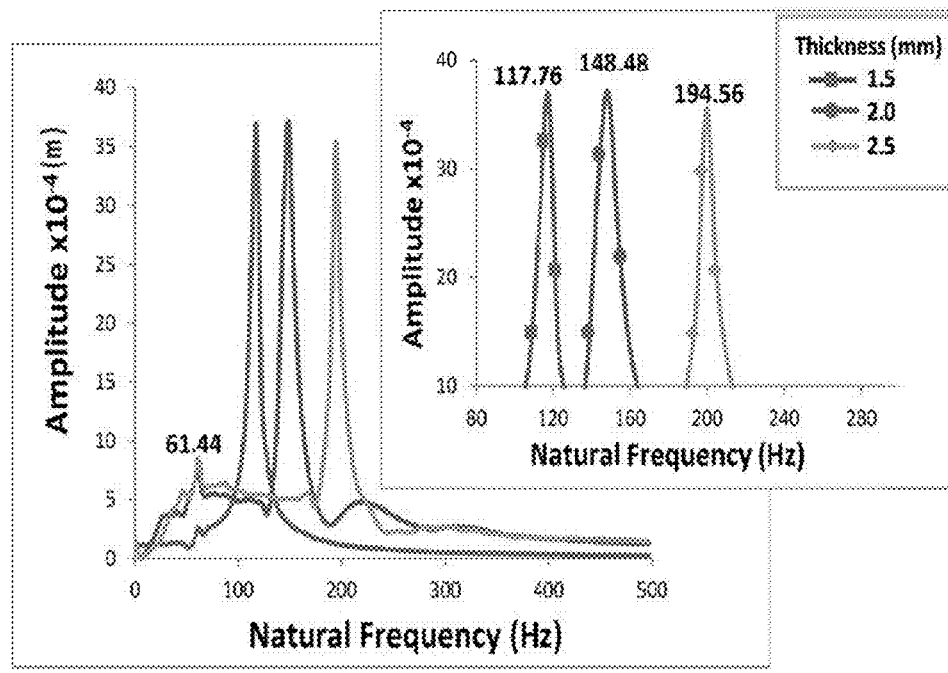
FIG. 29A is a graph of Natural Frequency of samples welded using 3 KW power and 400 mm/min welding speed for different thickness.
Figure 29B:
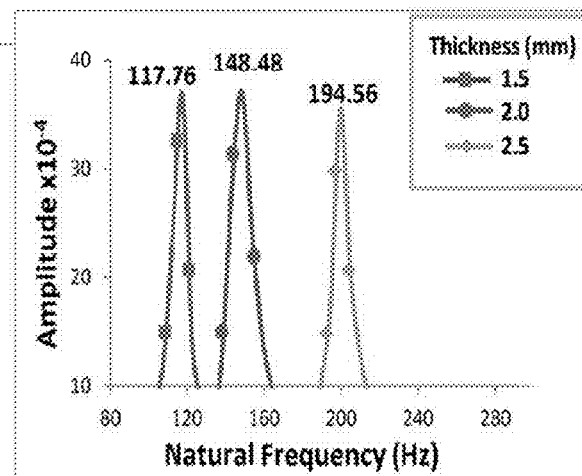
FIG. 29B is an expanded view of FIG. 29A.
Figure 30:
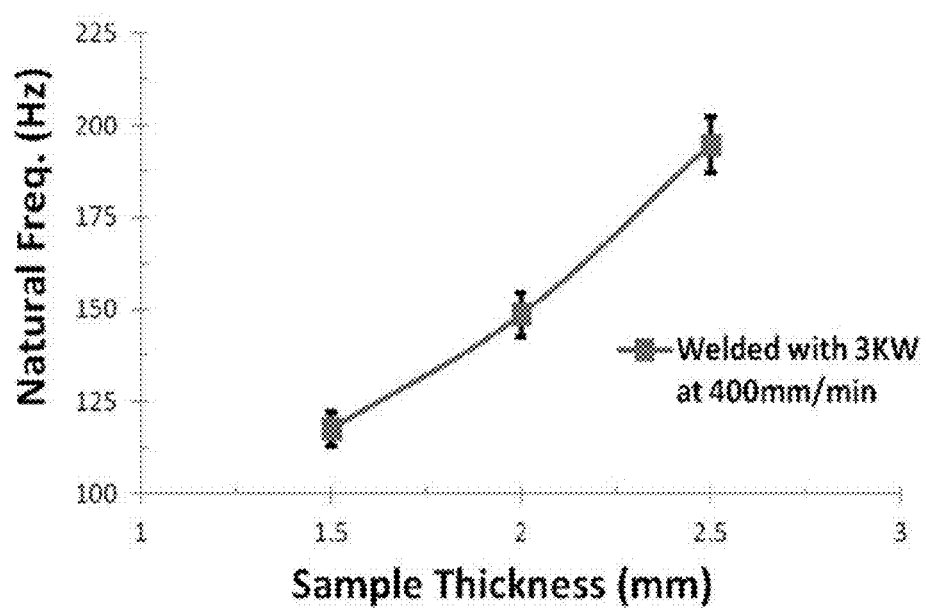
FIG. 30 is a graph of Natural Frequency variation with sample thickness.

Effects of the variation of the thickness of welded samples on the natural frequency were examined and shown in FIGS. 29A and 29B, where other welding and geometry parameters (welding speed, beam power etc. and length, breadth respectively) are held constant. FIG. 30 shows the variation of the natural frequency of investigated samples with sample thickness. An increase in the sample thickness results in an increase in the moment of inertia of the system, which directly relates to the natural frequency.

The natural frequencies obtained from modal analysis testing were then used to calculate the stiffness and elastic modulus of the welded blanks. Table 9 shows the calculated stiffness and elastic modulus of all samples. It is found that the values of the calculated elastic modulus are similar to that of the base material. Considering the welding and geometry parametric influence on the elastic modulus, the noticed difference may be due the modification of the material microscopic properties during the welding process.

TABLE 8

Comparison of the Natural frequency of modal test and numerical results of non-welded Samples

| Sample Thickness | Modal Test $f_n$ (Hz) | Numerical $f_n$ (Hz) | % Difference |
| --- | --- | --- | --- |
| 1.5 | 122.88 ± 6.14 | 111.39 | 9.81 |
| 2 | 153.60 ± 7.68 | 162.643 | 5.72 |
| 2.5 | 220.16 ± 11.00 | 215.91 | 1.95 |
| 3 | 271.36 ± 13.57 | 263.38 | 2.98 |

TABLE 9

Calculated Stiffness and Elastic Modolus of welded sample

| Power (W) | $F_n$ (Hz) | K (N/m) | E (GPa) |
| --- | --- | --- | --- |
| 2000 | 102.40 | 6679.0963 | 184.13 |
| 3000 | 117.76 | 8833.1048 | 243.64 |
| 4000 | 129.02 | 10603.076 | 292.26 |

TABLE 9-continued

Calculated Stiffness and Elastic Modolus of welded sample

|  | $F_n$ (Hz) | K (N/m) | E (GPa) |
|---|---|---|---|
| Speed (mm/min) | | | |
| 200 | 230.40 | 41519.479 | 247.16 |
| 300 | 215.04 | 36168.08 | 215.35 |
| 400 | 220.16 | 37910.872 | 225.31 |
| 200 | 122.88 | 9617.8987 | 265.07 |
| 300 | 107.52 | 7363.7037 | 203.10 |
| 400 | 117.76 | 8833.1048 | 243.64 |
| Thickness (mm) | | | |
| 1.5 | 117.76 | 8833.1048 | 243.64 |
| 2 | 148.48 | 15554.188 | 180.26 |
| 2.5 | 194.56 | 29606.977 | 176.16 |

Analysis of the Acquired Data

To predict the variation of welding speed (WS), laser beam power (LP), and sample thickness (ST) with data obtained from experiments, a step-wise regression analysis was carried out, where the insignificant model terms can be eliminated. Table 5 shows the natural frequency obtained from the experimentation and the corresponding variable matrix. Statistical software Minitab 16 was used to analyze the data. Variation inflammatory factor (VIF) check was conducted to test the collinearity and the interaction terms (WS*ST, WS*LP and ST*LP) of the parameters considered. The variance inflation factor (VIF) test revealed that the interaction and the second order terms do not contribute to the significance of the model. Hence, linear models were fitted to the experimental data so as to derive the regression equation and the fit summary output shows that this linear model is statistically favored for the natural frequency. The best subset regression (table 6) analysis revealed that the three independent parameters are essential for the best prediction of the model. All the adequacy measures are close to 1 which indicate adequate models, except for WS which indicates the less significant effect on the natural frequency. The analysis of the variance, t-test and p-values show that the main effect of the sample thickness (ST) and the laser beam power (LP) are the most significant model terms associated with the natural frequency. However, the sample thickness is the most significant term influencing the model. The resulting mathematically model from the regression in terms of these parameters is;

Nat. Frequency (NF)=−47.4−2842*(WS)+85678*(ST)+0.0168*(LP)  (30)

The accuracy related to the measured R-sq value of Eqn. (30) is in the order of 98.7%, the adjusted R-sq value is 98% and the predicted R-sq value is 96.61%.

Figure 31A:
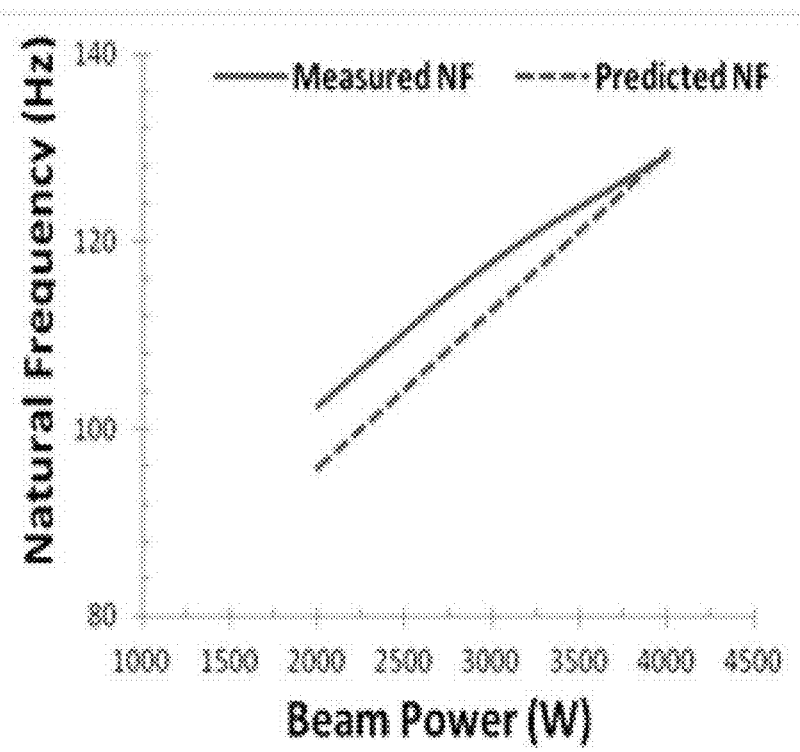
FIG. 31A is a graph of Measured and Predicted Natural Frequency variation with Laser Beam Power.
Figure 31B:
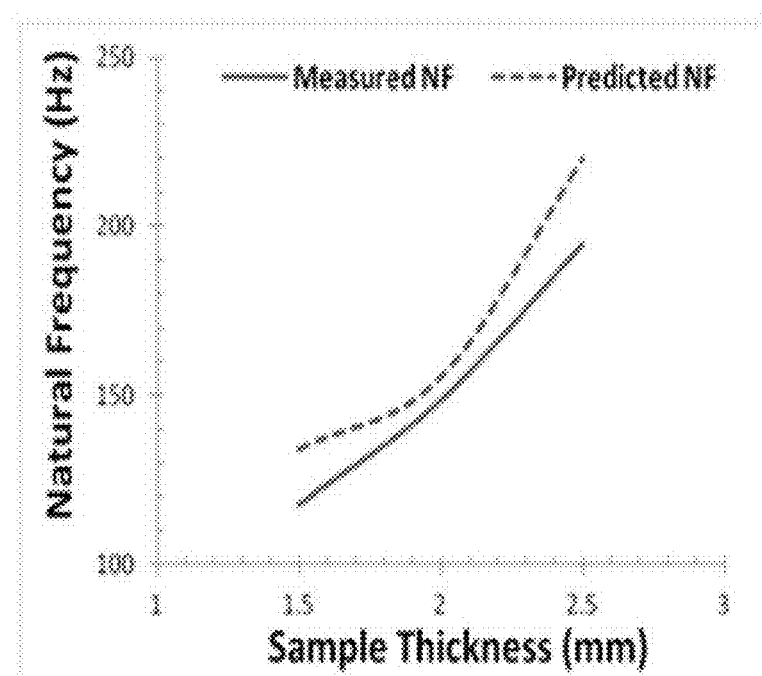
FIG. 31B is a graph of Measured and Predicted Natural Frequency variation with Sample Thickness.
Figure 32:
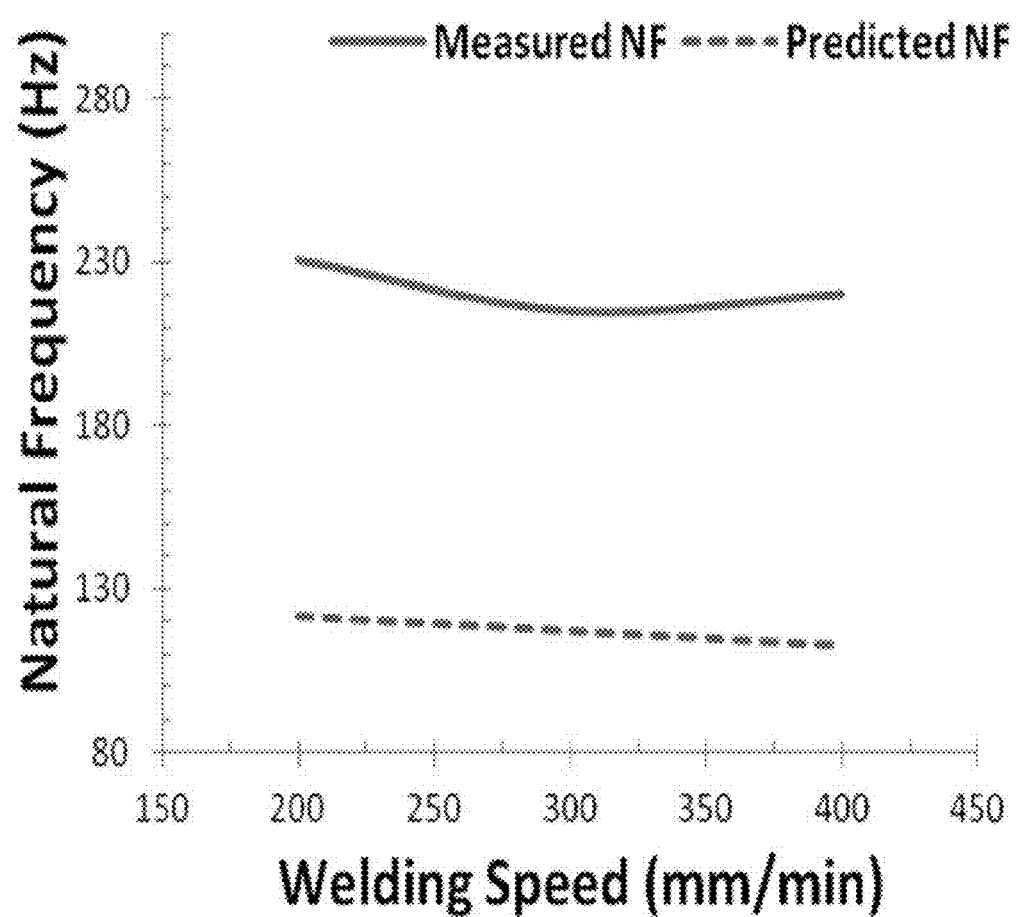
FIG. 32 is a graph of Measured and Predicted Natural Frequency variation with welding speed.

FIGS. 31A and B compares between the measured and predicted variation of the natural frequency with the laser power and the samples thickness respectively. The predicted natural frequency is follows similar trend and is in agreement with the measured natural frequency. The little deviation observed result from the effect of the welding speed, which has less contribution to the accuracy of the model. If ST and LP are held constant, the deviation of the model from the measured natural frequency becomes high as illustrated in FIG. 32. The sample thickness is the major influencing parameter of the natural frequency and was another indication of the defect-free weld joint resulting from the laser welding process.

TABLE 10

Best Subsets Regressions

Best Subsets Regression: NF versus WS, ST, LP

Response is NF

| Vars | R-Sq | R-Sq (adj) | Mallows Cp | S | WS | ST | LP |
|---|---|---|---|---|---|---|---|
| 1 | 93.9 | 93.1 | 21.3 | 13.314 | | X | |
| 1 | 49.1 | 42.8 | 220.1 | 38.338 | | | X |
| 2 | 98.1 | 97.5 | 4.6 | 7.998 | | X | X |
| 2 | 95.3 | 94 | 16.7 | 12.405 | X | X | |
| 3 | 98.7 | 98 | 4 | 7.2106 | X | X | X |

TABLE 11

Regression Equation
The regression equation is
NF = −47.4 − 2842 WS + 85678 ST + 0.0168 LP

| Predictor | Coef | SE Coef | T | P | VIF |
|---|---|---|---|---|---|
| Constant | −47.43 | 17.74 | −2.67 | 0.037 | |
| WS | −2842 | 1759 | −1.62 | 0.157 | 1.06 |
| ST | 85678 | 5782 | 14.82 | 0 | 1.43 |
| LP | 0.016753 | 0.004367 | 3.84 | 0.009 | 1.5 |

S = 7.21063
R-Sq = 98.7%
R-Sq(adj) = 98.0%
PRESS = 784.224
R-Sq(pred) = 96.61%

Example 4

Material Characterization

The macrograph and micrograph of the cross-section of each sample were examined using a metallurgical optical microscope (Meiji MX7100, USA) and scanning electron microscope SEM (LYRA3 XM, TESCAN, Germany) to reveal the shape of the fusion zone and the weld bead width.

Macrostructure of the Welded Samples

The macrograph of the weld was examined to observe the shape of the fusion zone, the weld bead width and the full penetration weld across the sample thickness. Combination of the optical microscope and SEM were utilized in this examination. Due to non-uniformity in the shape of the fusion zone, a mean value of weld bead widths at the top, the center and the bottom is reported as the weld bead width for all the examined samples.

Figure 33A:
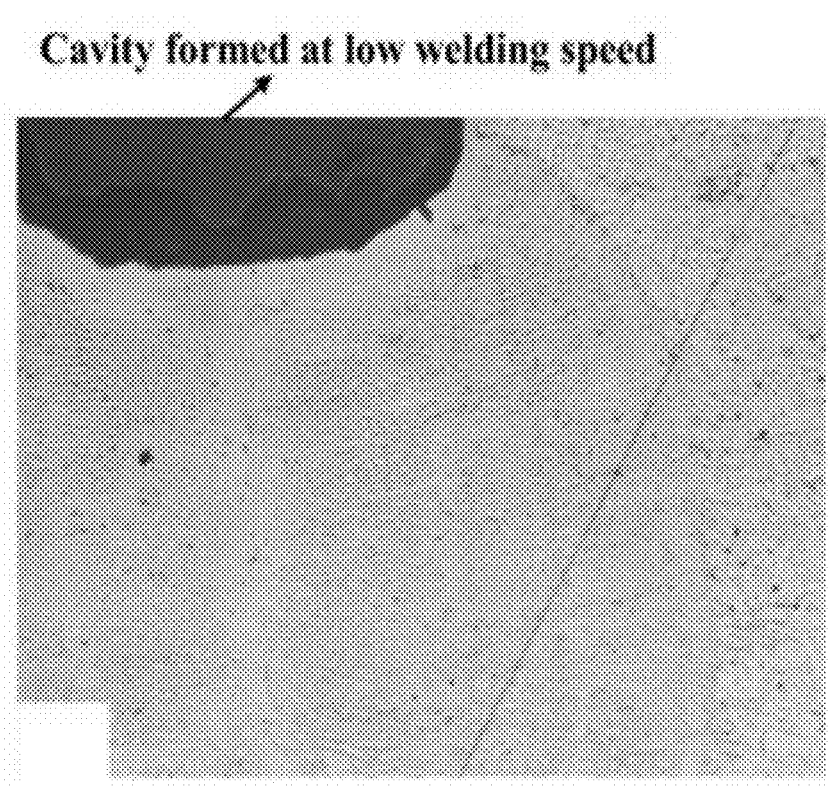
FIG. 33A is an Optical Micrograph of the cross-section welded samples with a feed rate of 200 mm/min.

It is seen from the micrographs showing the weld inlets and outlets that some materials loss occurs from the top and bottom surfaces respectively. This loss is associated to the evaporation of the workpiece's material due to exposure to the laser welding beam so far that this removal of material from the surface is not substantial enough to significantly reduce the sample thickness. However, significant material loss at the top surface which leads to the formation of a cavity (FIGS. 33(a) & 35(c)) was observed at higher beam power which allows for quick evaporation of the material at the present of high intensity laser beam. This behavior was also noticed at lower welding speed as in FIG. 33(a). This is because of the increased dwell time of the laser beam power on the irradiated area which provides the evaporation at the surface and the recoil pressure developed in between the vapor front and the molten surface enhances the cavity formation in the irradiated region as observed in "See N. Abu-Dheir and B. S. Yilbas, "Quality Assessment and Metallurgical Examination of Laser Welded Sheets," *Advanced Materials Research* vol. Vols. 83-86 pp. 611-615, 2010 (reference), incorporated herein by reference in its entirety". Material removal at the bottom surface is however inconspicuous, indicating that there is no excessive heating across the workpiece material during welding.

(a) Effect of Welding Speed

Figure 33B:
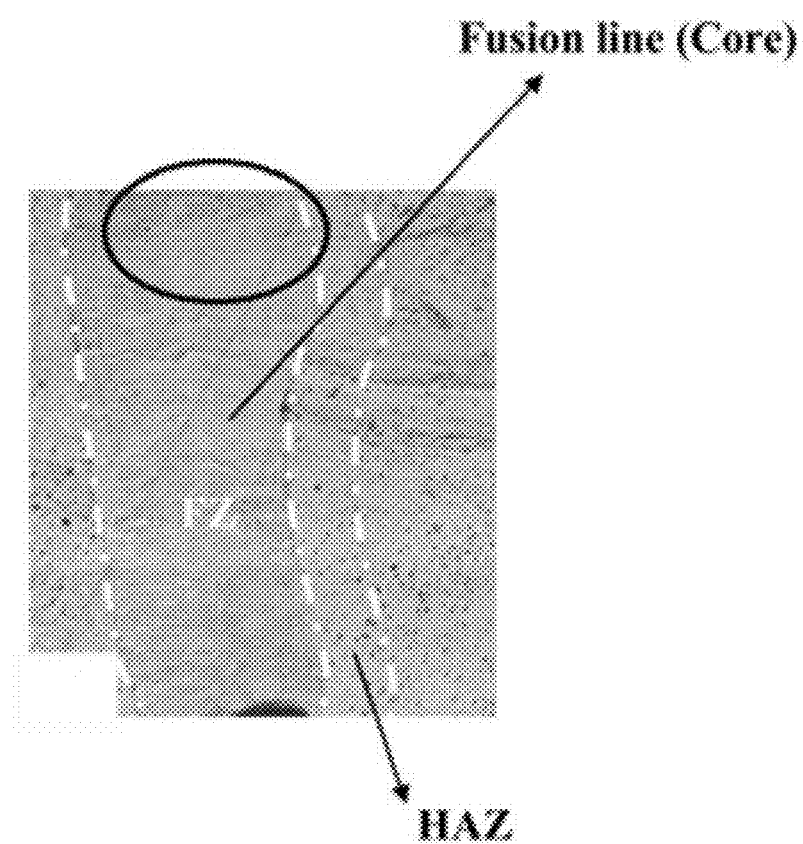
FIG. 33B is an Optical Micrograph of the cross-section welded samples with a feed rate of 200 mm/min.
Figure 33C:
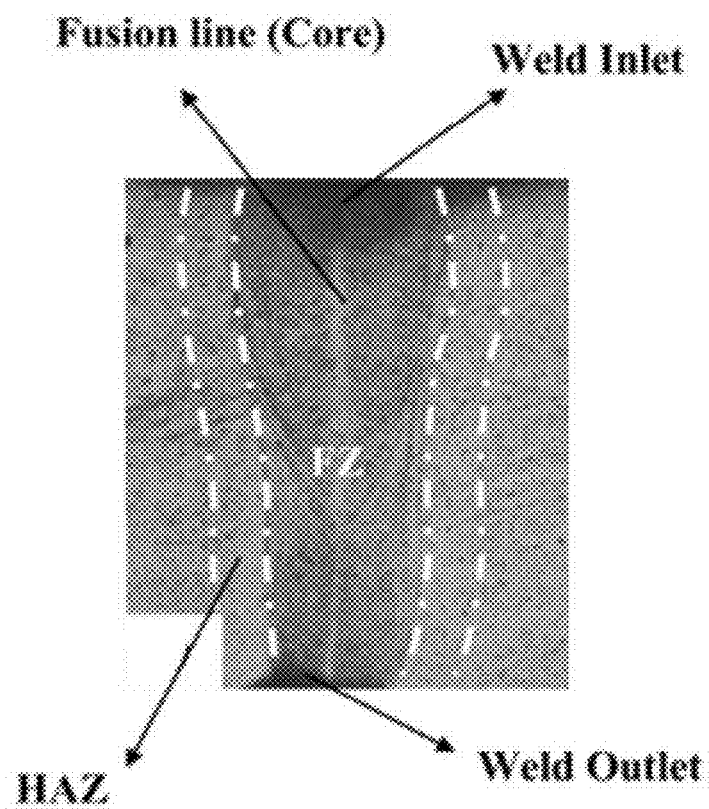
FIG. 33C is an Optical Micrograph of the cross-section welded samples with a feed rate of 300 mm/min.
Figure 33D:
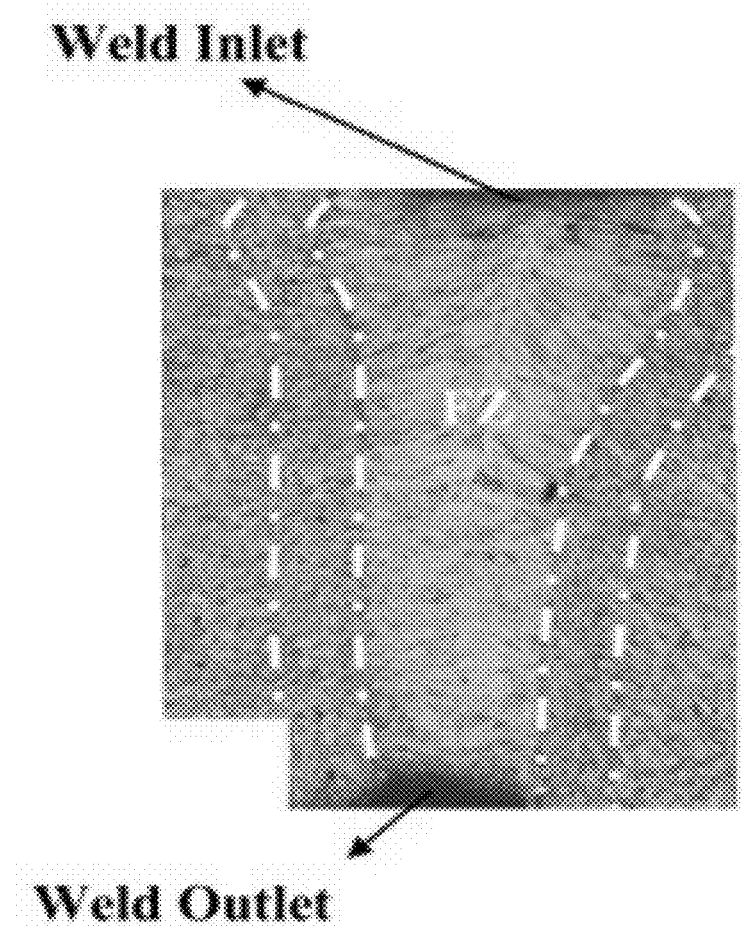
FIG. 33D is an Optical Micrograph of the cross-section welded samples with a feed rate of 400 mm/min (×5). All welds were with a Laser beam Power=4 kW and a Sample thickness=2.5 mm.

The parameters of tables 3 & 4 were used for demonstrating the effects of the welding speed. FIG. 33b-d shows the optical micrograph of the three fusion zones welded with 4 kW laser beam power. The fusion zones were almost symmetrical along the weld line except for some enlargement at the upper part of the weld. This enlargement can be due to any or a combination of the following reasons as stated in: i) temporal fluctuations in the laser output power, ii) arbitrarily varying in the scanning speed, iii) changes in the assisting gas pressure (argon) during the welding process, and iv) inhomogeneity of the material such as elemental concentration variation in the welding section. It was observed that the initial variation of the process parameters e.g. laser power and welding speed, are most influential factors responsible for the irregular weld width variation at the top portion.

Figure 34A:
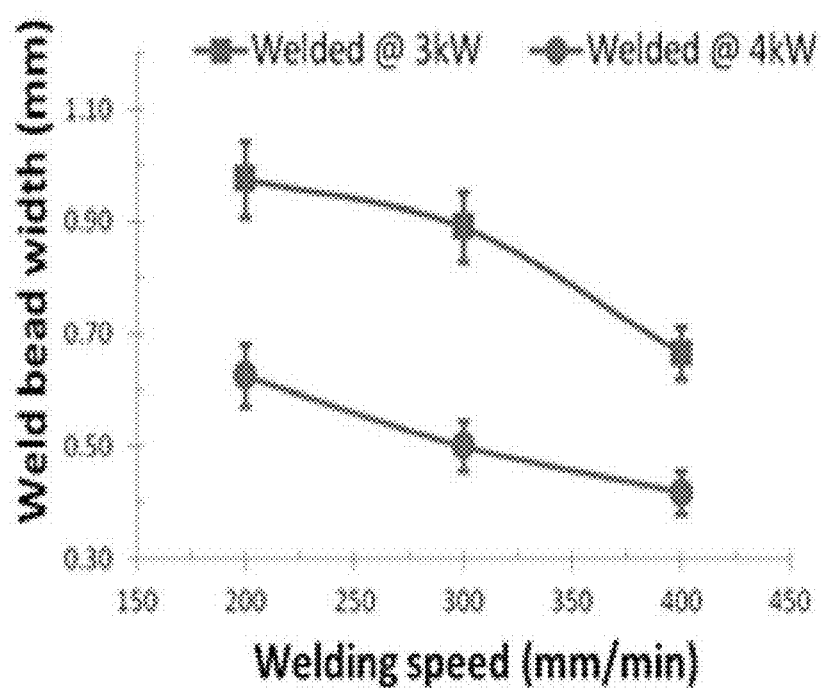
FIG. 34A is a graph of variation of Weld Zone width with welding speed.
Figure 34B:
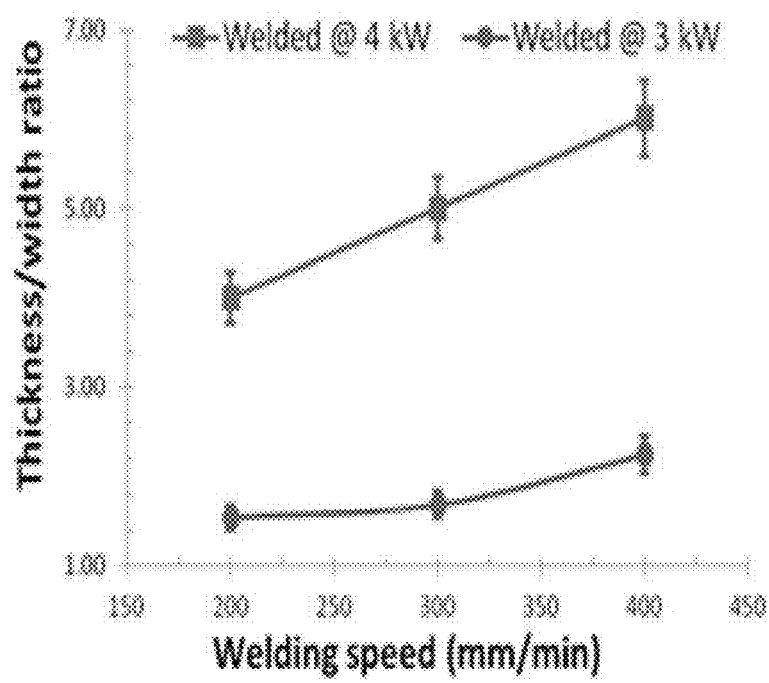
FIG. 34B is a graph of variation of Depth/Width ratio of the weld zone with welding speed.

It is also noted that the weld bead width is indirectly related to the welding speed. Therefore, as the welding speed increased from 200 to 400 mm/min, the weld thickness/width ratio increased from 4 to 6 and from 1.5 to 2.3 for 4 kW and 3 kW powers respectively. These relationships are clearly plotted in FIG. 34 (a-b), where the linear behavior between welding speed and weld bead width, and between the welding speed and the thickness/bead width ratio is depicted. An increase welding speed reduced the laser beam dwell time on the workpiece. Consequently, the sample experiences less heat absorption and coupled with a high temperature gradient associated with laser welding translates to a narrow weld seam at higher welding speed.

(b) Effect of Laser Power

Figure 35A:
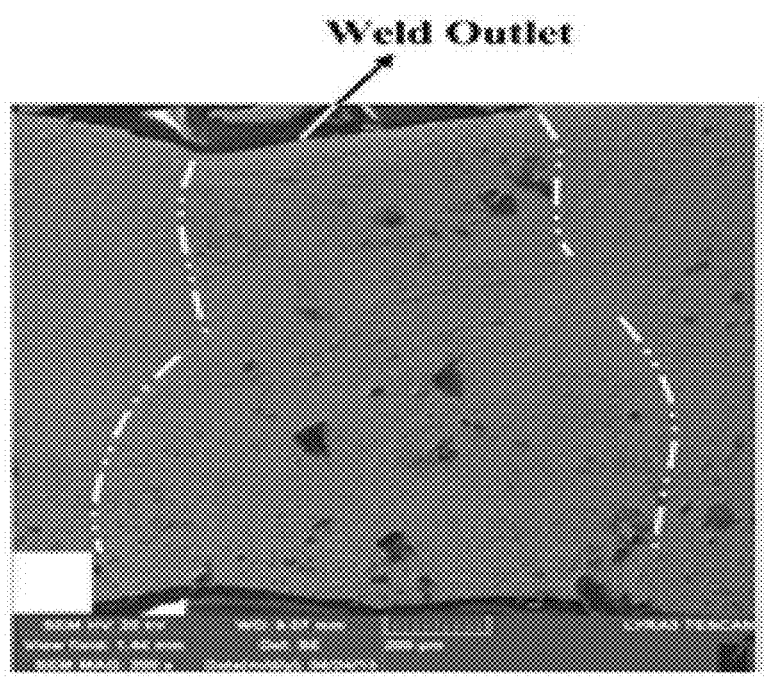
FIG. 35A is an SEM micrograph of a welded sample with a power of 2 kW.
Figure 35B:
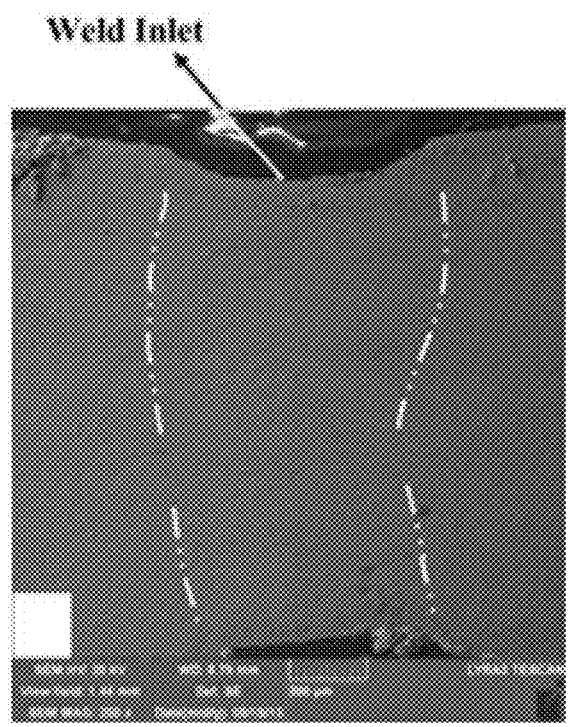
FIG. 35B is an SEM micrograph of a welded sample with a power of 3 kW.
Figure 35C:
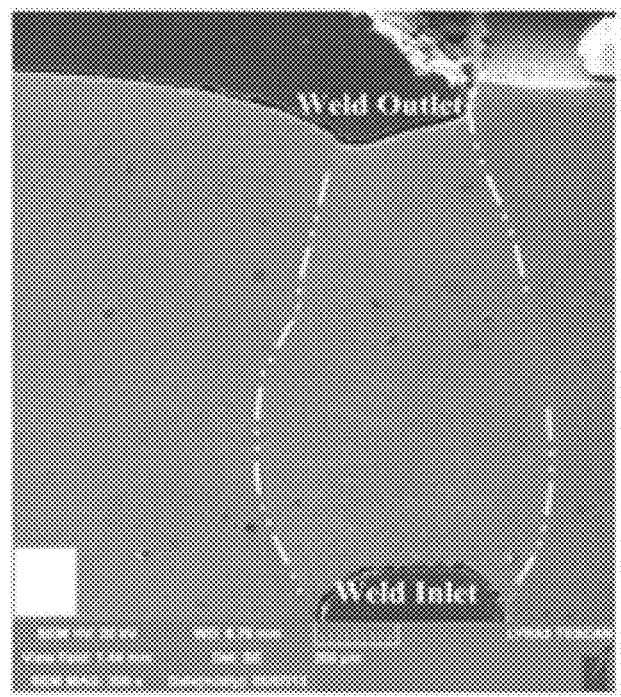
FIG. 35C is an SEM micrograph of a welded sample with a power of 4 kW.
Figure 36A:
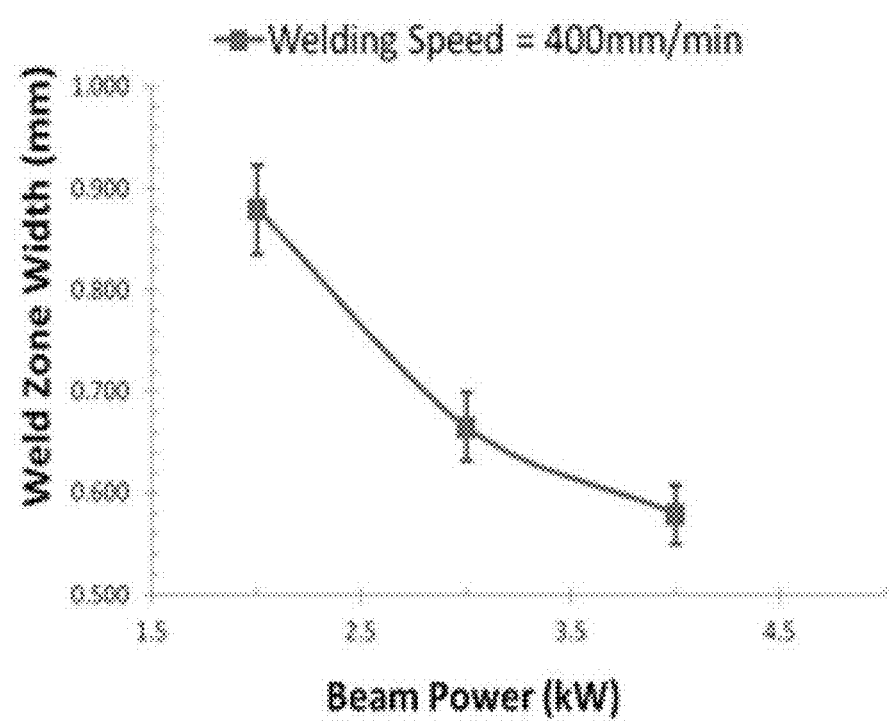
FIG. 36A is a graph of variation of Weld Zone width with laser power.
Figure 36B:
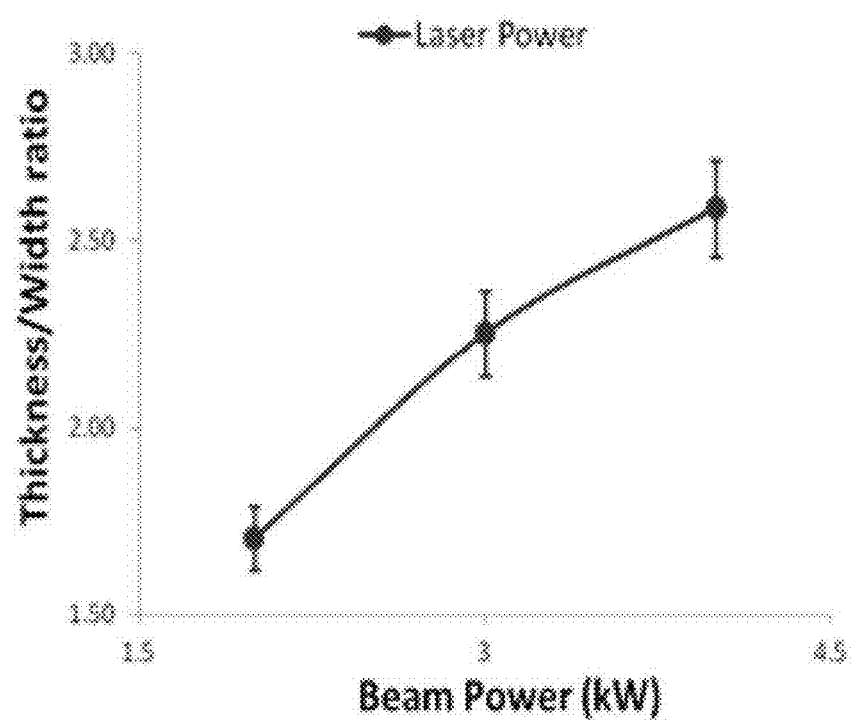
FIG. 36B is a graph of variation of Depth/Width ratio of the weld zone with Laser Power.
Figure 37A:
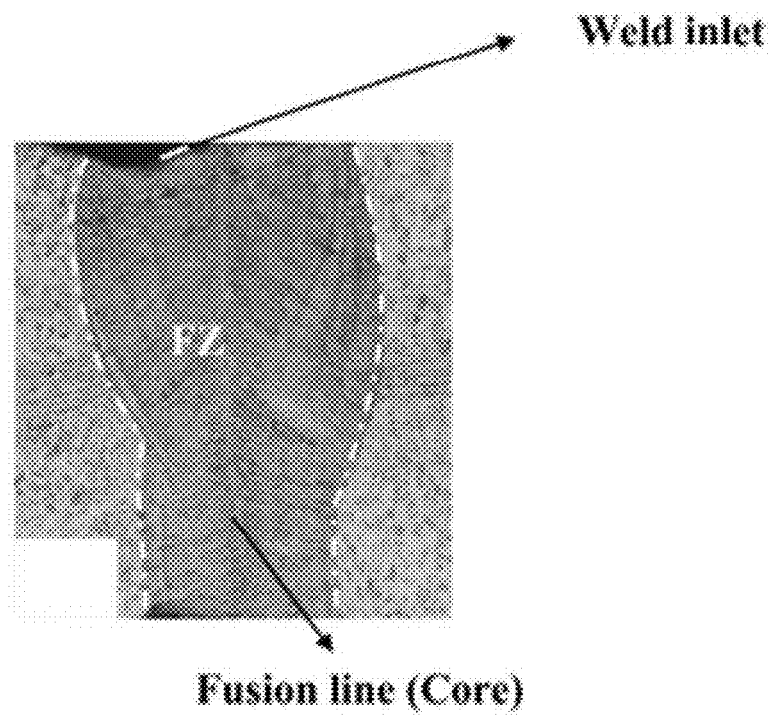
FIG. 37A is an Optical Micrograph of the cross-section of samples welded with a Power of 2 kW.
Figure 37B:
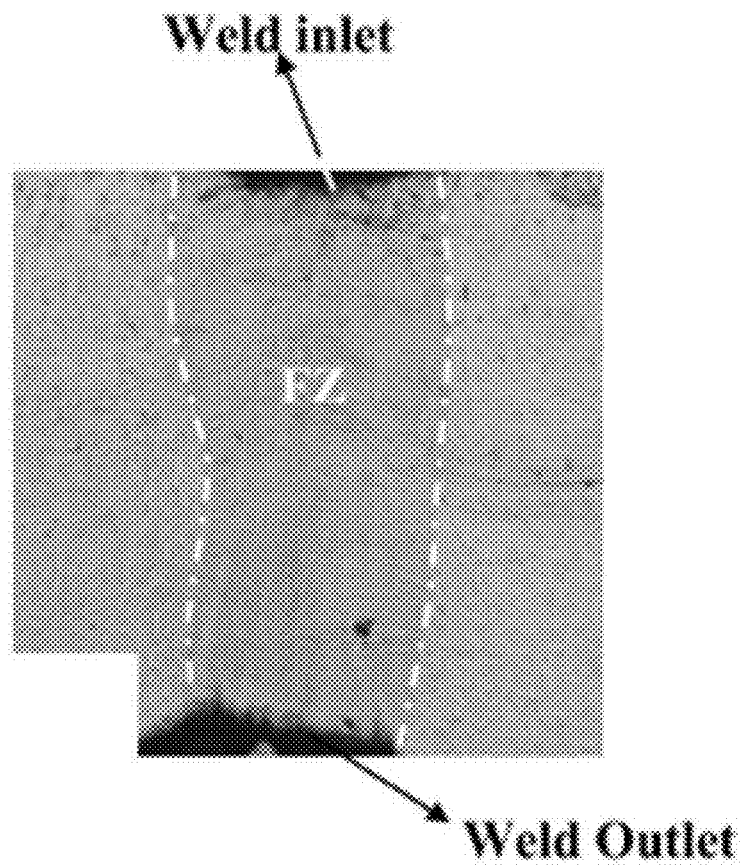
FIG. 37B is an Optical Micrograph of the cross-section of samples welded with a Power of 3 kW.
Figure 37C:
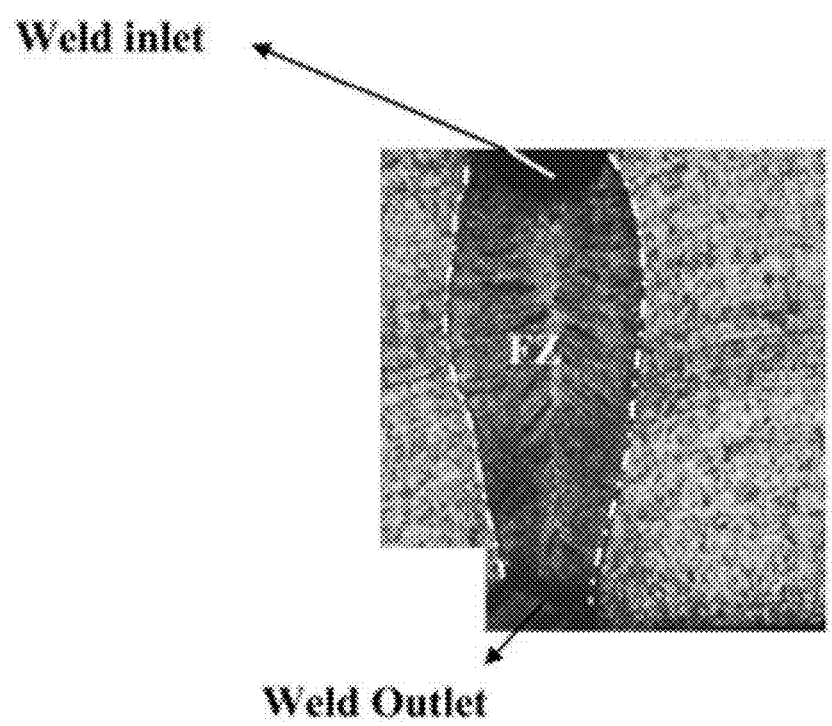
FIG. 37C is an Optical Micrograph of the cross-section of samples welded with a Power of 4 kW (×5). All welds were with a Welding speed=400 mm/min and a Sample thickness=1.5 mm.

FIG. 35A-C shows the SEM micrograph of welded samples with varied laser power while other parameters were held constant (see table 5). It was observed from FIG. 36A-B that the measured width of the welded zone decreased while the thickness/bead width ratio increased as the laser power increases. This behavior is associated to the amount of heat absorbed by the surface, solidification and cooling rates. As the surface is irradiated with a higher power, more heat is absorbed especially at a low welding speed, leading to higher temperature gradient across the welding line. This in turn results into a higher solidification rate with a reduced weld-affected area (weld zone). Although in previous studies, it was observed that the laser power has less significant influence on the fusion zone shape and on the depth/width ratio. But since the welding in this study was done at low scanning rate (400 mm/min), it might be responsible for the significant contribution noticed. The optical images of these welded samples are shown in FIG. 37A-C revealing clearly the decreasing nature of the weld width as the beam power increases.

(c) Effect of Blank Thickness

Figure 38A:
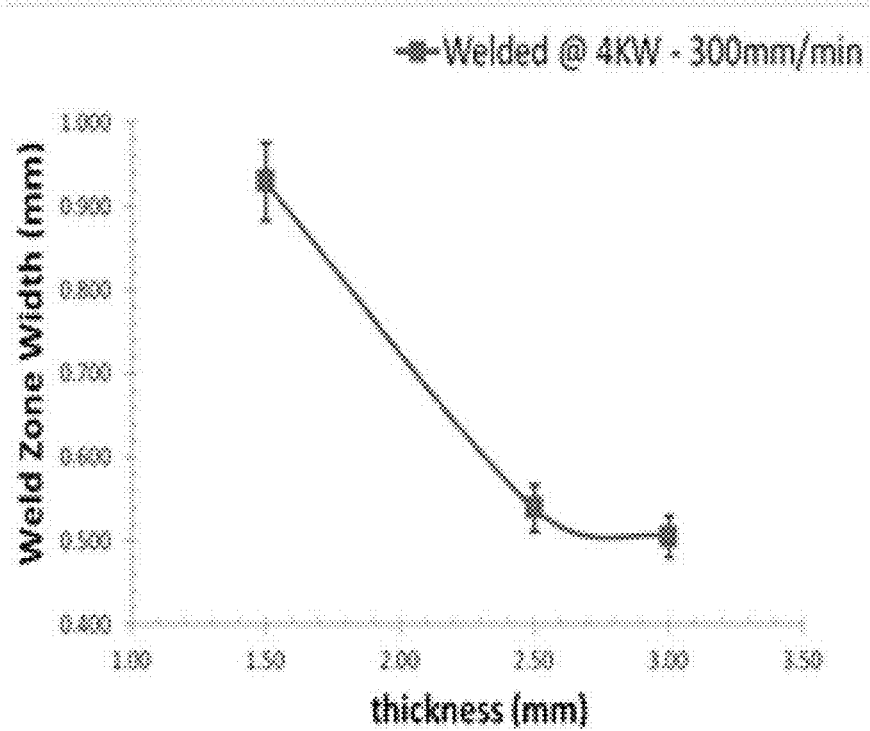
FIG. 38A is a graph of Weld zone width variations with sample thickness.
Figure 38B:
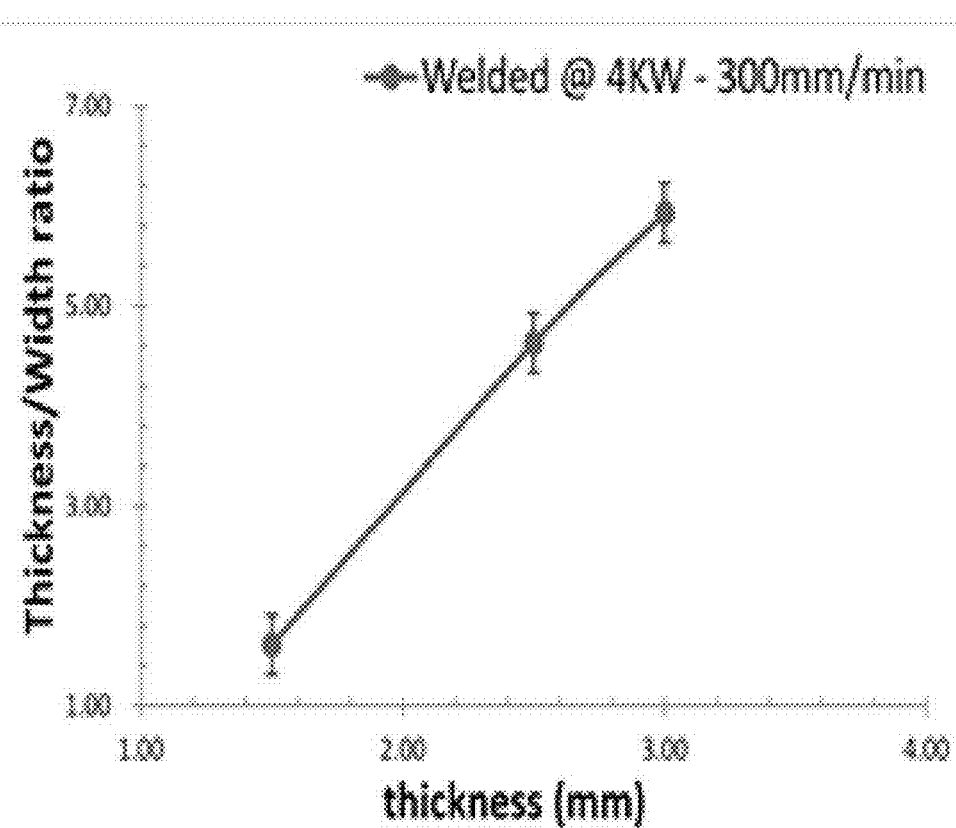
FIG. 38B is a graph of Depth/width ratio variation with sample thickness.
Figure 39A:
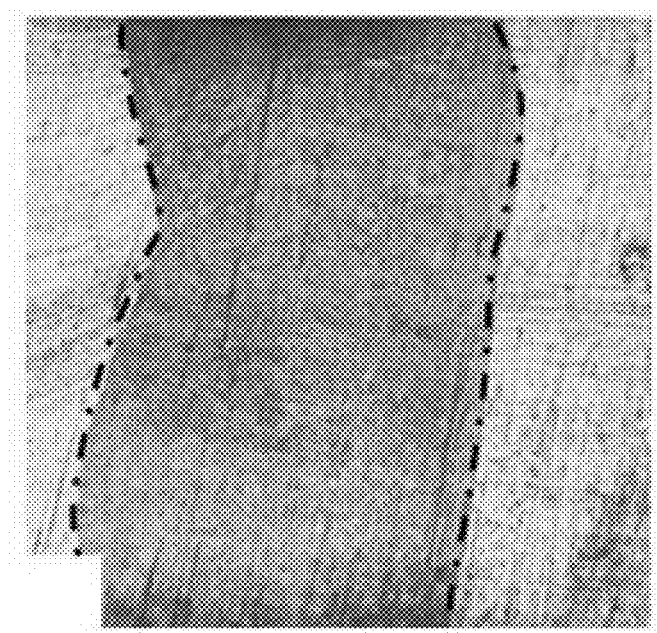
FIG. 39A is an Optical Micrograph of the cross-section of samples with thickness of 1.5 mm welded with 4 kW-300 mm/min.
Figure 39B:
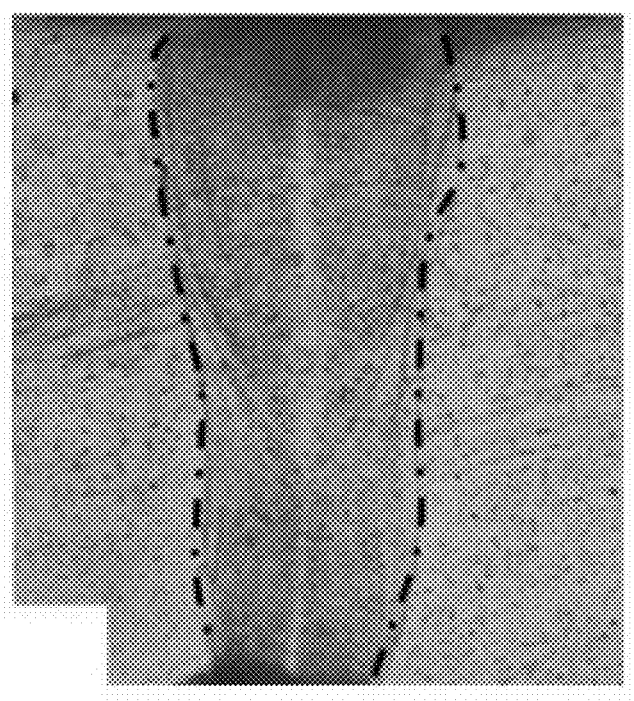
FIG. 39B is an Optical Micrograph of the cross-section of samples with thickness of 2.5 mm welded with 4 kW-300 mm/min.
Figure 39C:
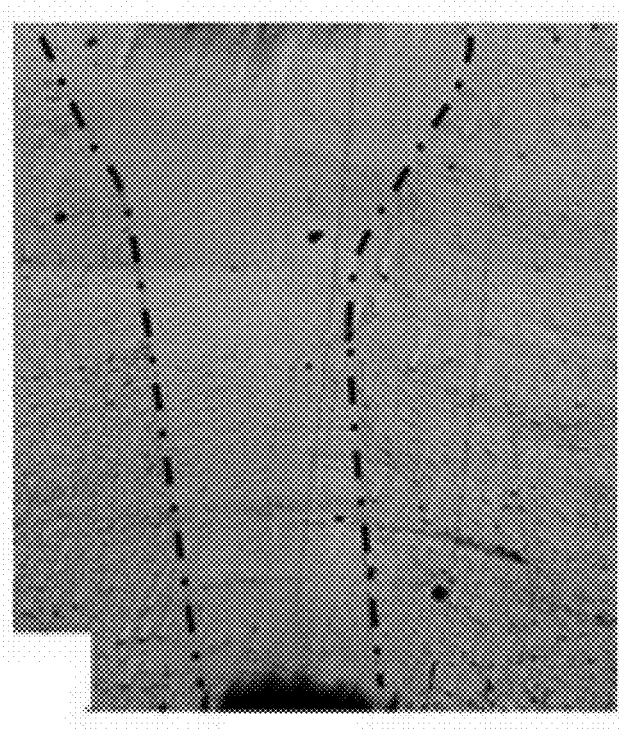
FIG. 39C is an Optical Micrograph of the cross-section of samples with thickness of 3 mm thickness (×5) welded with 4 kW-300 mm/min.

The geometrical thickness of the welded plate also influences the fusion zone size during welding as previously illustrated in Table 6 shows the blank thickness variation examined. FIG. 38A-B shows the bead width and the thickness/bead width ratio variation with thickness, a sharp decrease in the width of the welded zone was noticed as the thickness increased from 1.5 mm to 2.5 mm. This is caused by the decrease in the power per bulk material which consequently decreases the peak temperature while also reducing the temperature gradient. In addition, the solidification and cooling rates thus increased thereby reducing the interaction of the affected area with the beam power which then resulted in the observed reduction in the bead width size. However, investigating all samples reflects that the width decrease was less significant after 2.5 mm (as shown in FIG. 38(a)). This could be as a result of higher thermal efficiency accompanied by increase in the thickness of the workpiece as stated in, which is required for a sound weld. As the thermal efficiency increases, the power per bulk material increases and more materials interact. Hence, the smaller the effect of the beam power on the bead width size at a large sample thickness. The optical micrograph of fusion zone shape of different thickness is shown in FIG. 39A-C for samples welded using 4 kW laser beam power at 300 mm/min welding speed. The symmetry along the welding line is obvious except for some irregular enlargement noticed due to the aforementioned possible reasons.

Microstructure of the Welded Samples

Figure 40A:
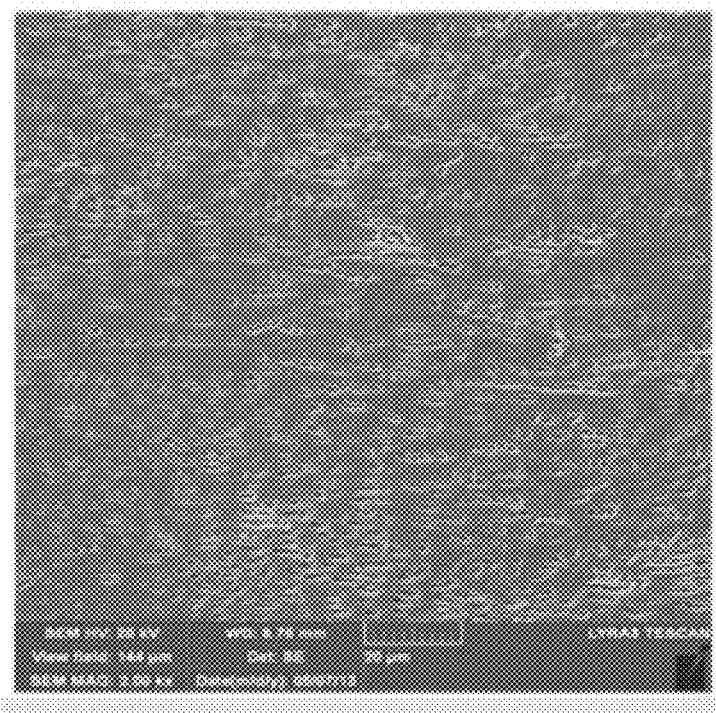
FIG. 40A is an SEM cross-section at the neighborhood of HAZ for BP=3 KW.
Figure 40B:
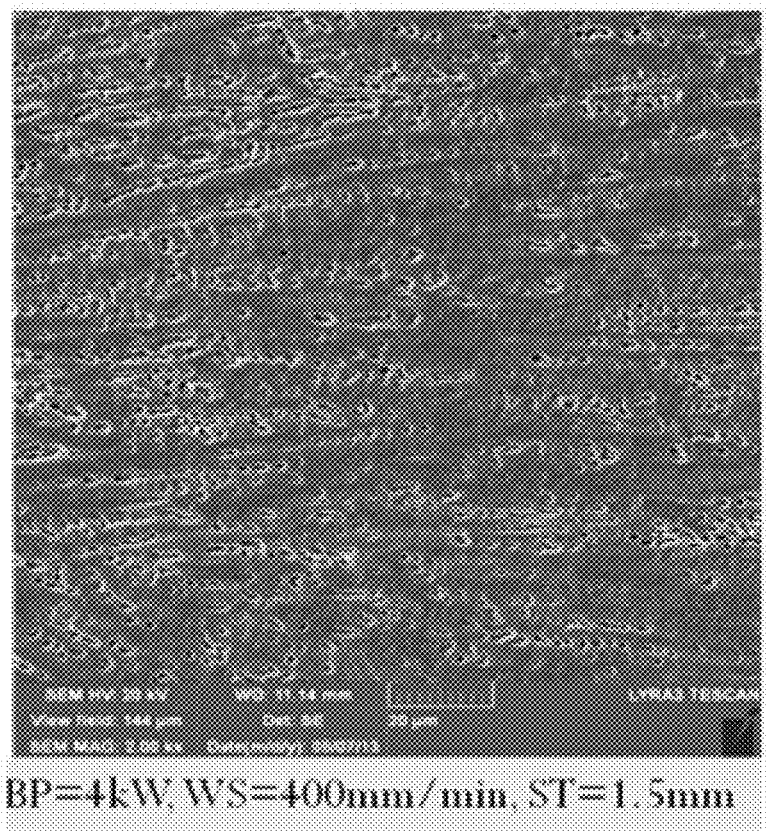
FIG. 40B is an SEM cross-section at the neighborhood of HAZ for BP=4 KW.
Figure 40C:
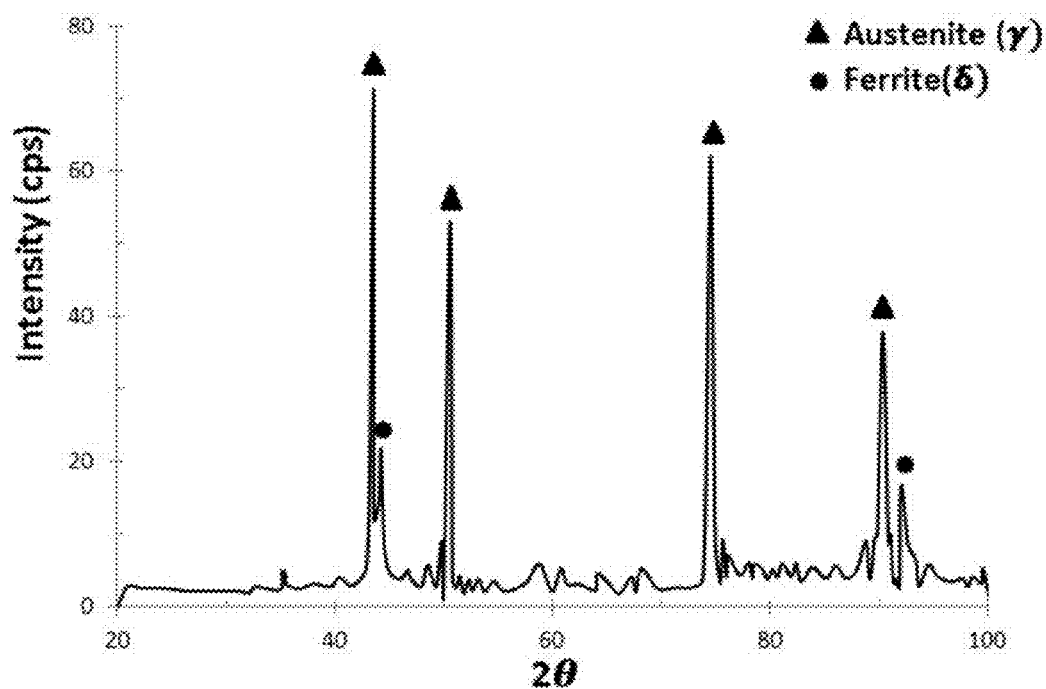
FIG. 40 C is a X-ray diffractogram of the welded surface.
Figure 41A:
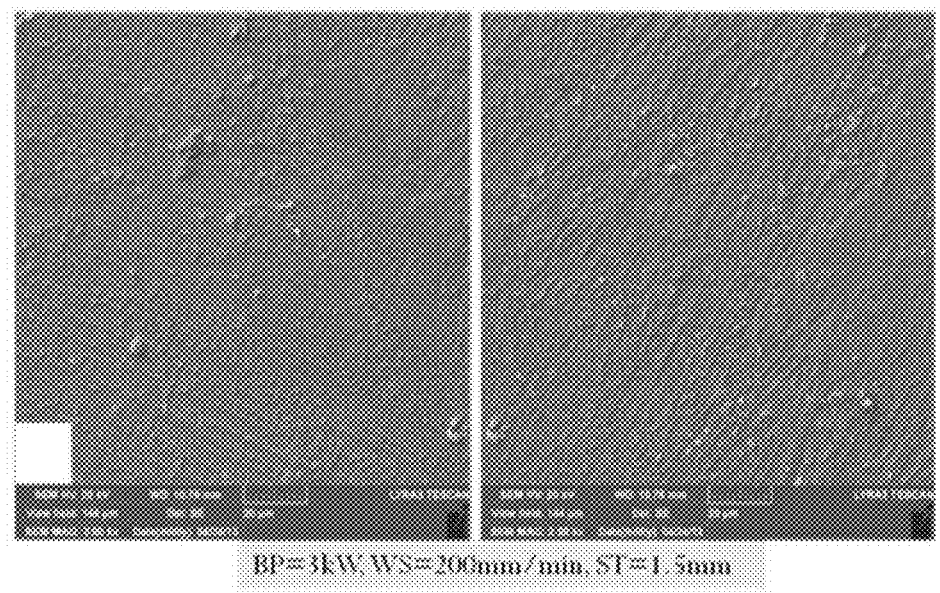
FIG. 41A is a SEM cross-section across the weld zone showing both the columnar and dendritic microstructures.
Figure 41B:
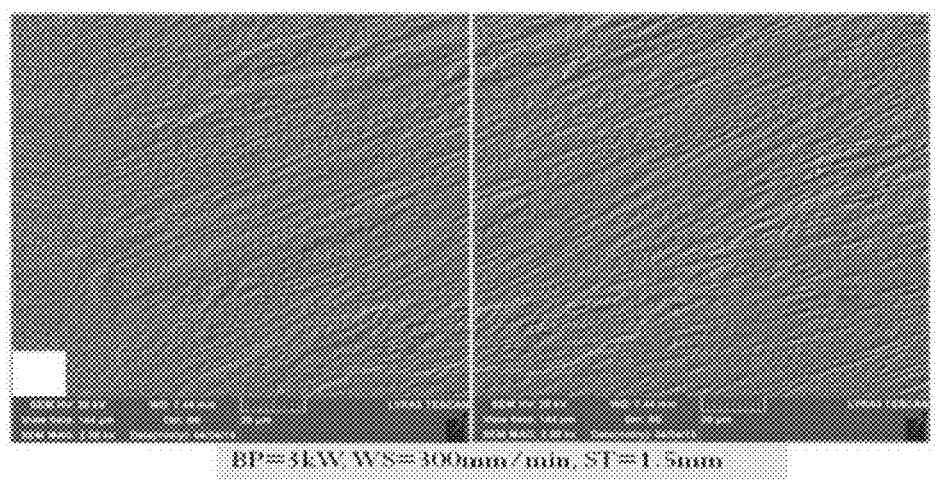
FIG. 41B is a SEM cross-section across the weld zone showing both the columnar and dendritic microstructures.
Figure 41C:
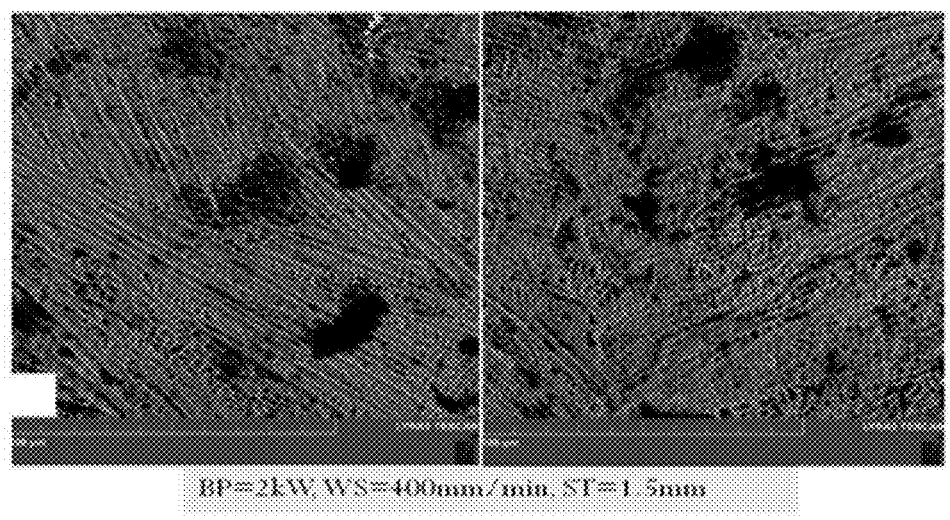
FIG. 41C is a SEM cross-section across the weld zone showing both the columnar and dendritic microstructures.

SEM micrographs showing different regions of weld cross section are obtained to analyze the post-welding microstructures. For all investigated samples, it was observed from the micrograph as shown in FIGS. 40 and 41, that there are microstructural variations within the fusion zone. It was noticed that dendritic microstructures are formed in the near neighborhood of the fusion zone because of the relatively higher cooling rate than in the fusion zone.

Figure 42:
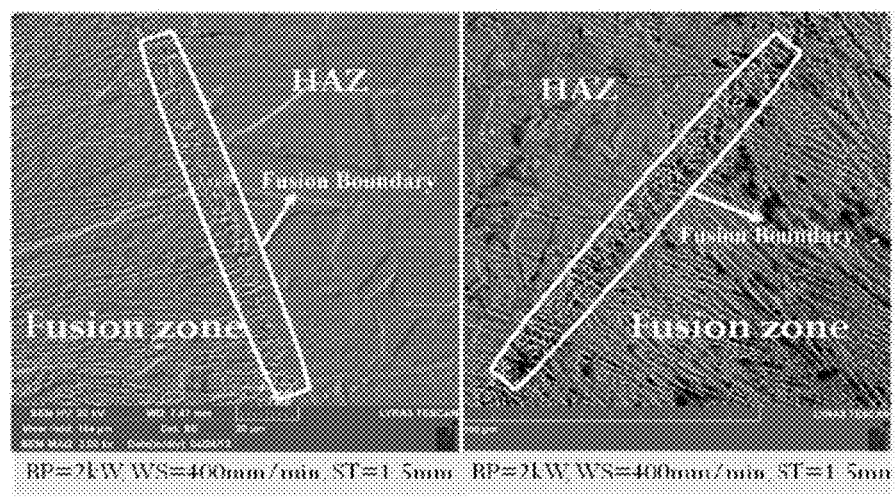
FIG. 42 is a SEM micrograph showing fusion boundary and HAZ of welded samples.
Figure 43:
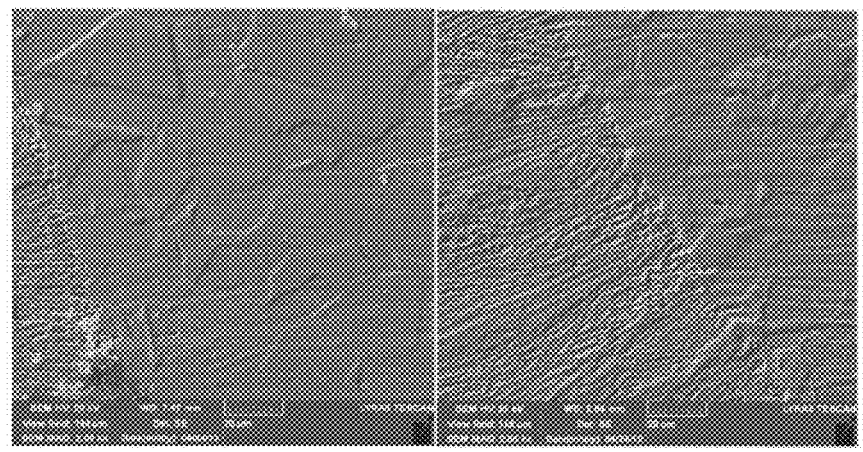
FIG. 43 is a SEM micrograph of showing grain coarsening in HAZ of welded samples.

The SEM micrographs in FIGS. 41 and 42 show clearly the fusion and heat affected zones respectively. The weld section displays both cellular and dendritic microstructures, which contains the austenitic phase. This behavior is primarily due to variation in the solidification rate and temperature gradient across the fusion zone. The solidification rate is lowest (almost zero) along the fusion boundary (boundary between solid-liquid interface during welding) and maximum along the centerline due to its high temperature and very low temperature gradient. As the solidification process moves towards the fusion boundary, the temperature gradient decreases, while the solidification rate increases. This variation in temperature gradient and solidification rates towards the center line result in an increased tendency toward cellular growth, i.e., a transition from planar to cellular growth occurs, resulting in columnar grains that are noticed close and around the center line. Further towards the centerline, there is increased reduction in the temperature gradient and increased solidification rate. This results in subsequent transition of some of the cellular structures to dendritic structures around the centerline in the fusion zone. However, the absence of microcracking during solidification of the fusion zone and fusion boundary indicates that the solidification strains are well below the ductility of the weld material.

The HAZ of the welded samples were also examined using SEM (FIGS. 40-43). The grain coarsening in the HAZ due to self-annealing as a result of high temperature and low cooling rate is clearly depicted in FIG. 43. Moreover, in the neighborhood of the heat affected zone and fusion zones, the partial decomposition of the ferrite takes place through the growth of the austenite phase in line with Widmanstatten-type mechanism inside the ferrite grains. FIG. 40c is the X-ray diffractogram of the welded surface. It was observed from the x-ray peaks that $\delta$-Fe and $\gamma$-Fe were present. This is attributed with the high cooling rates at the surface, due the incomplete transformation of the $\delta$- and $\gamma$-phases and metastable $\delta$-Fe phase.

Figure 44A:
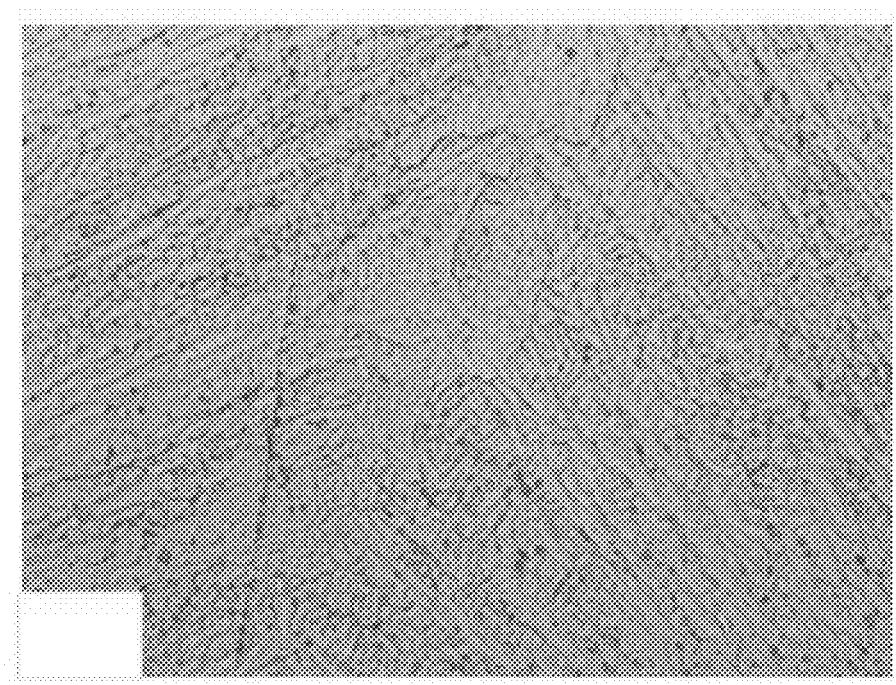
FIG. 44A is a Microstructure of laser welded samples at 3 kW laser power at a welding speed of 200 mm/min.
Figure 44B:
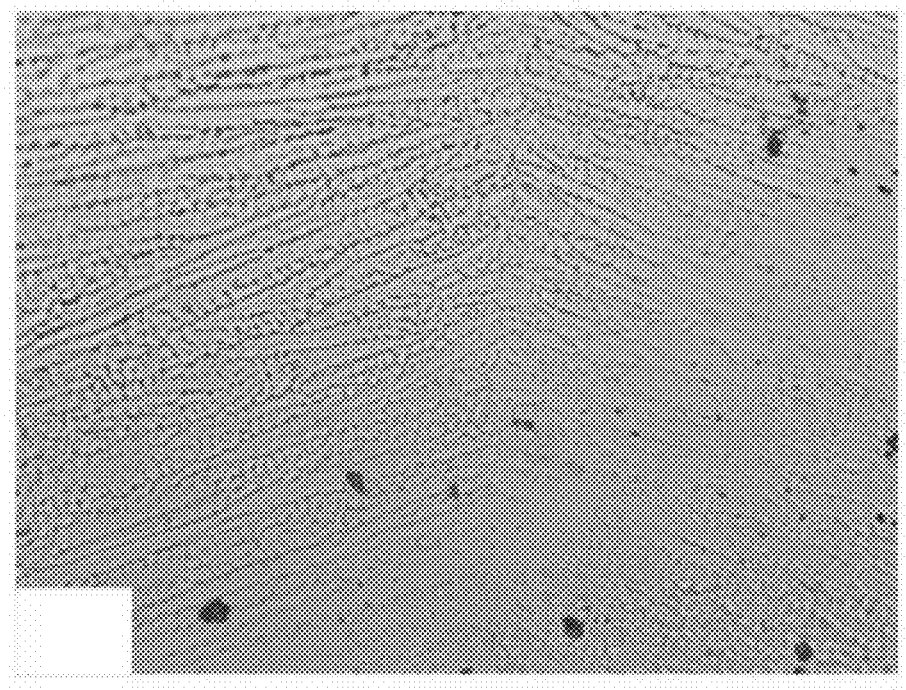
FIG. 44B is a Microstructure of laser welded samples at 3 kW laser power at a welding speed of 200 mm/min 400 mm/min (×50).

Effect of the welding speed on the microstructure was also examined. It was noticed that the microstructure becomes finer as the welding speed increase as evident from FIG. 44A-B. This is due to increase in the solidification and cooling rates due to less heat input which is a consequence of the increase in welding speed.

Figure 45A:
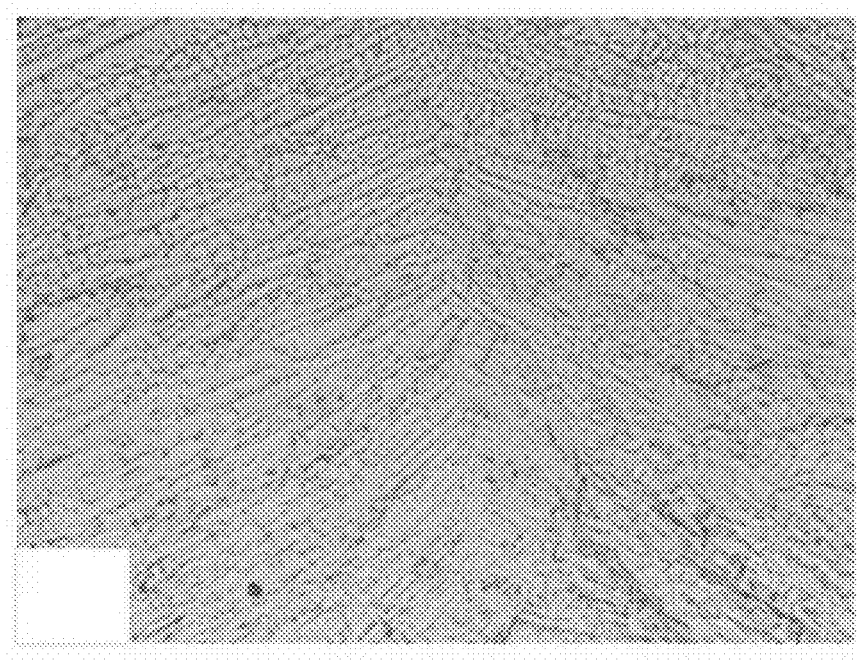
FIG. 45A is Microstructure of laser welded samples at 400 mm/min welding speed with a laser power of 2 kW.
Figure 45B:
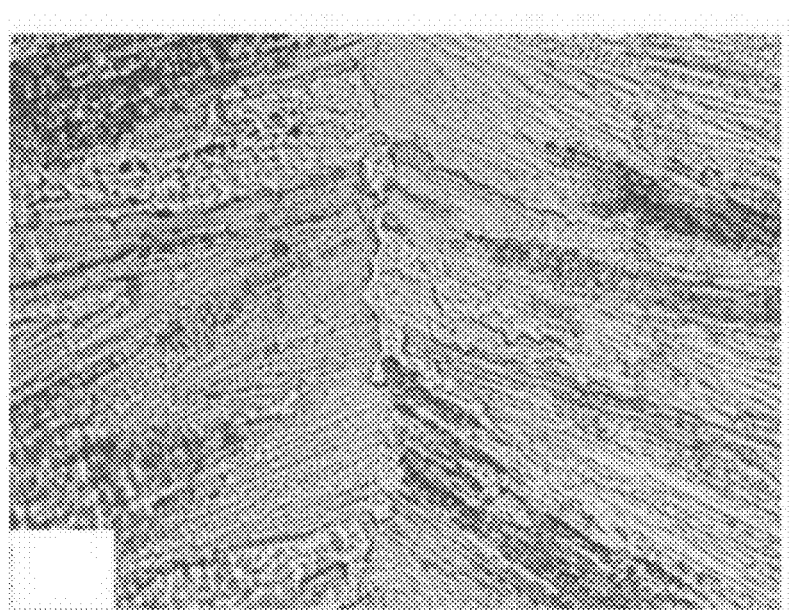
FIG. 45B is Microstructure of laser welded samples at 400 mm/min welding speed with a laser power of 4 kW (×50).

The microstructure of welded samples with different laser beam power indicates grain coarsening with an increase in laser output power (FIG. 45A-B). This is also due to increase in the heat input subsequent to increase in the beam power which decreases the cooling and solidification rates. In addition, more heat input also favors grain growth which is attributed to the coarse nature of the microstructure at an increased beam power.

Figure 46A:
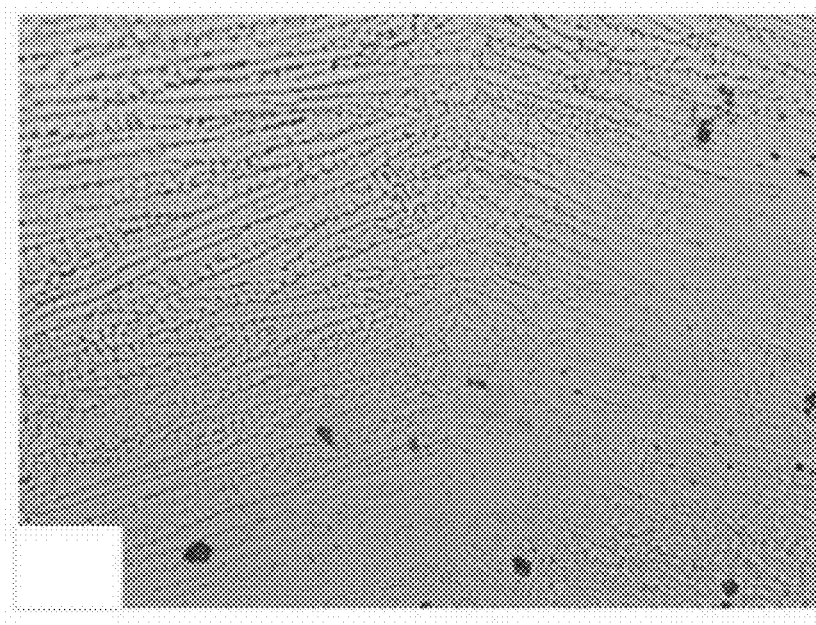
FIG. 46A is a Microstructure of laser welded samples using 4 kW beam power and 400 mm/min welding speed with a blank thickness of 1.5 mm.
Figure 46B:
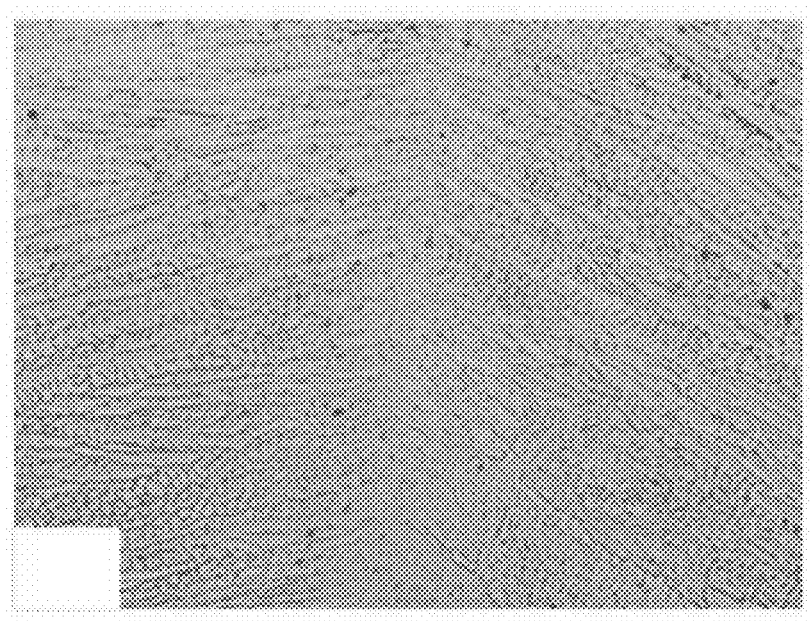
FIG. 46B is a Microstructure of laser welded samples using 4 kW beam power and 400 mm/min welding speed with a blank thickness of 2 mm (×50).

The effect of the thickness on the microstructure is shown in FIG. 46A-B. The microstructure of the samples becomes coarser as the thickness of the blank increases possibly because the thermal efficiency increases as the blank thickness increases due to higher heat absorption rate. This consequently causes a higher temperature gradient and decreases the solidification rates, hence the resulting coarse microstructure at a higher sample thickness.

Example 5

Microhardness of Welded Samples

Figure 47:
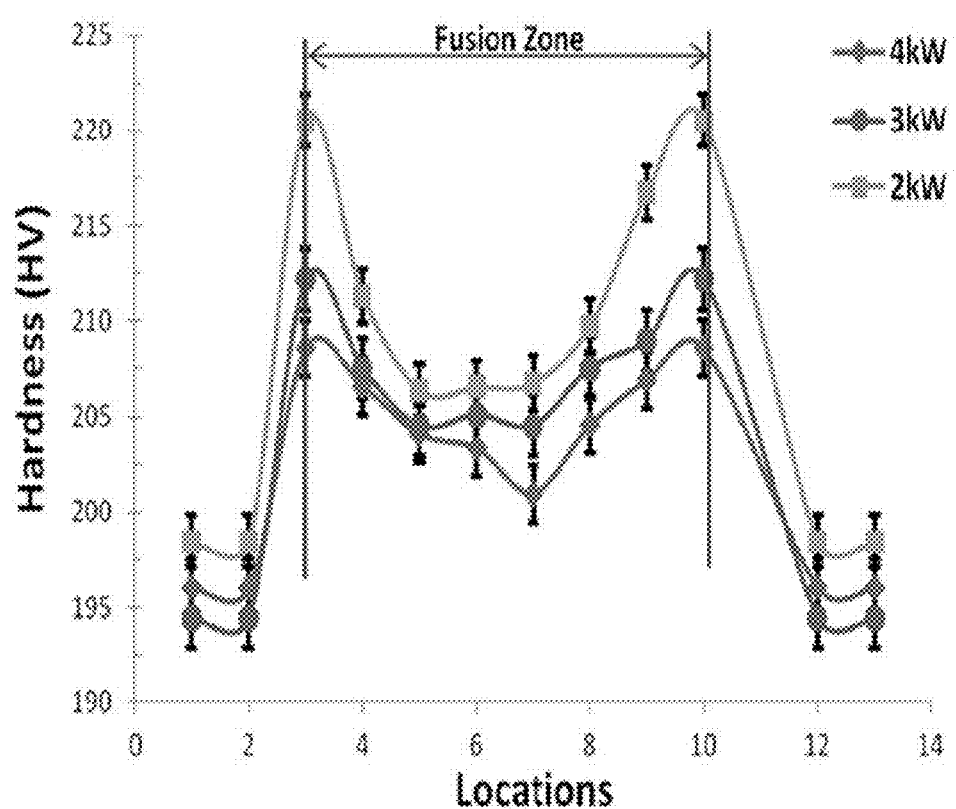
FIG. 47 is a graph of microhardness at different locations across fusion zone (welding speed=400 mm/min, Sample thickness=1.5 mm).

The microhardness distribution of the fusion zone was conducted using the Vickers HV (300 g) microhardness testing machine. To account for possible errors, all measurement were expressed in the form $\bar{a}\pm s$ where $\bar{a}$ is the average value of three hardness measurements recorded for a given location and s is the standard deviation within the readings. FIG. 47 shows the microhardness distribution of three welded samples across the fusion zone (FZ). Locations 5, 6 and 7 are on/around the fusion or center line; locations 3 and 10 were within 5 μm from the fusion boundary into the fusion zone from both sides, locations 4, 8 and 9 were between the centerline and the fusion boundary on both sides, while other locations are on the base material. The hardness drops rapidly from the fusion boundary towards the fusion line for all samples investigated. The peak hardness is about 15% higher than the base metal (BM) hardness. This corresponds to the microstructural formation across the FZ, they consist of majorly fine microstructures.

Figure 48:
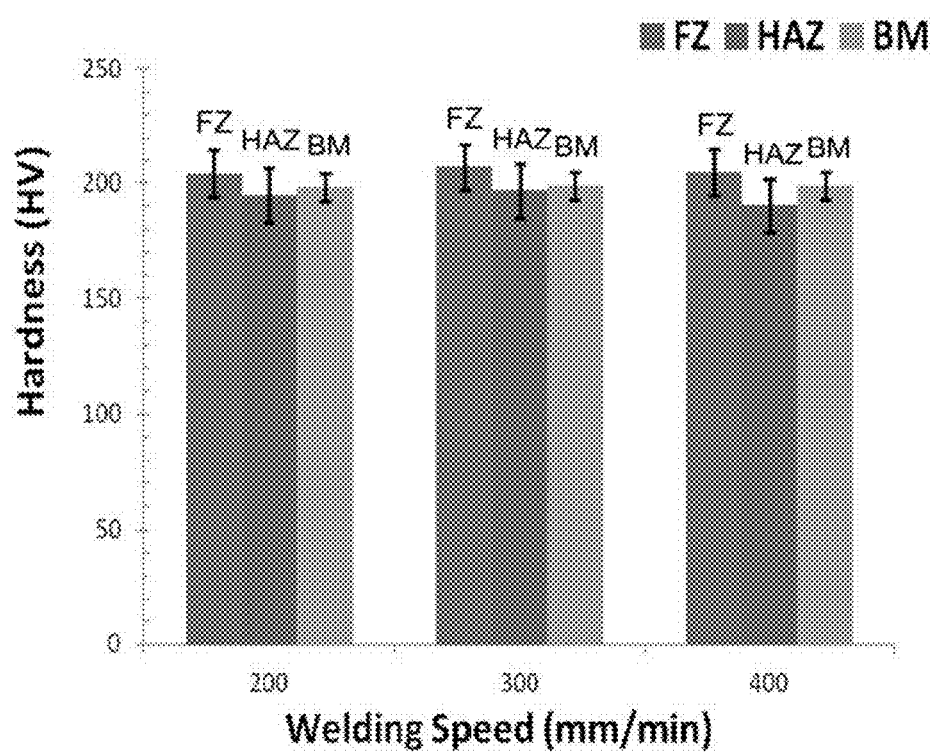
FIG. 48 is a graph of Vickers Micro-Hardness variation with Welding Speed for the FZ, HAZ and BM (BP=3 kW & ST=1.5 mm).
Figure 49:
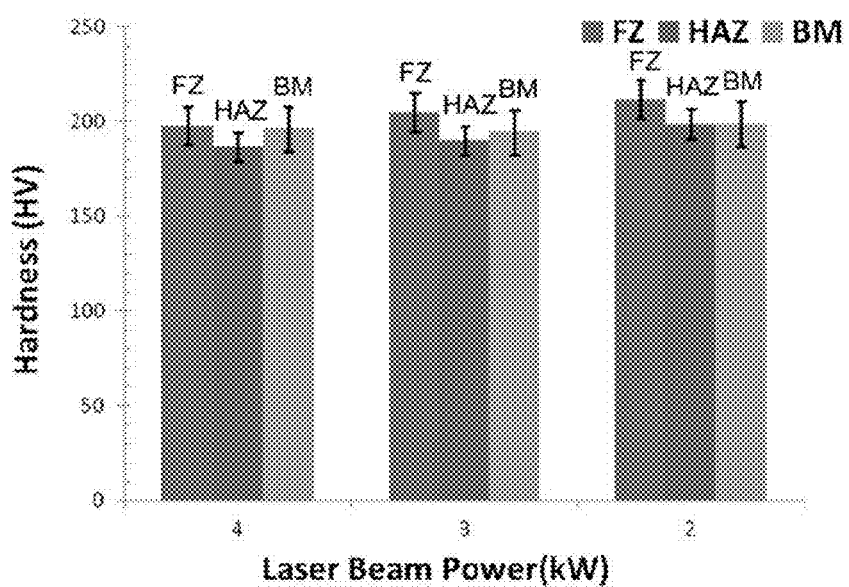
FIG. 49 is a graph of microhardness variation with Beam Power for the FZ, HAZ and BM (WS=400 mm/min & ST=1.5 mm).
Figure 50:
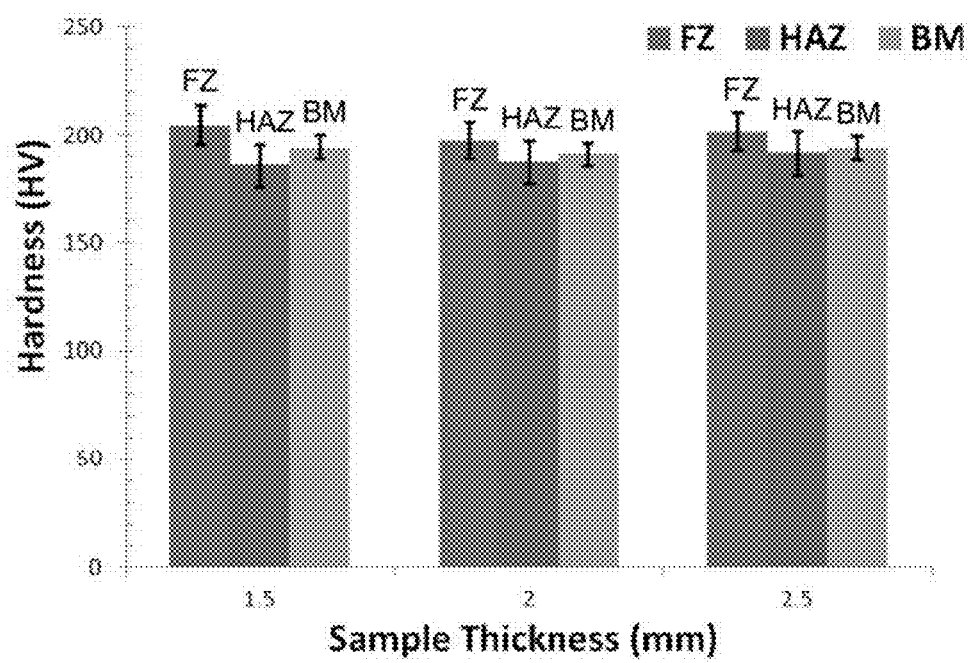
FIG. 50 is a graph of Vickers Micro-Hardness variation with Sample Thickness for the FZ, HAZ and BM (BW=3 kW & WS=400 mm/min).

Parametric effects on the microhardness were also investigated. FIG. 48 and FIG. 49 are histograms showing the variation of the microhardness with welding speed and beam power respectively. No significant difference in the hardness of the FZ for the range of welding speeds investigated was noticed. However, the HAZ hardness is always lower than that of the base metal (BM) while the increasing reduction in cooling rate at higher welding speed results in the slight reduction in the HAZ hardness with welding speed. Beam power has a noticeable impact on the hardness. In addition, the BM hardness is seen to exceed the HAZ hardness in most of the hardness measurements; this is due to the tempering that occurs at the HAZ during the welding process. The hardness variation with sample thickness is shown in FIG. 50. The hardness relatively decreased as the sample thickness increased; this behavior is due to the amount of heat per mass density in the sample which plays an important role in the microstructural development at the fusion zone and the HAZ. Tempering at the HAZ dictates reduced hardness, and decreases with sample thickness, which resulted in the higher hardness noticed for the sample with 2.5 mm thickness.

In general, the microhardness fell between 198 HV and 211 HV for the fusion zone (FZ), between 186 HV and 199 HV for the heat affected zone (HAZ) and between 191 HV and 200 HV for the base metal (BM) for all samples investigated. This illustrates that the welded joint has an improved mechanical property compared to the base material; however, the high hardness in the FZ is attributed to both fine microstructure and the inherent stresses developed during welding process.

Example 6

Simulation Results

Thermal Analysis

Figure 51:
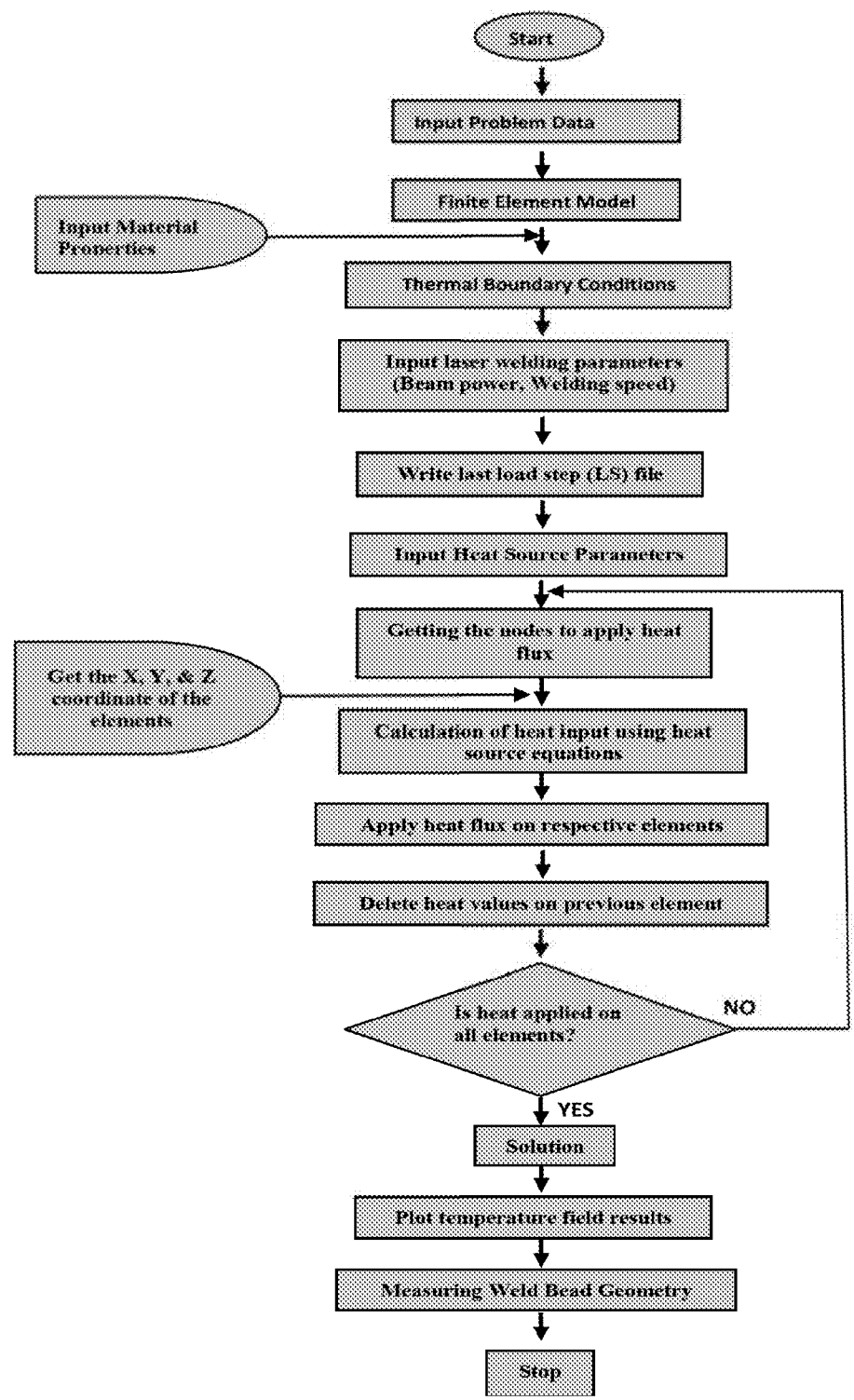
FIG. 51 is a flowchart of the APDL module for the thermal analysis.
Figure 52A:
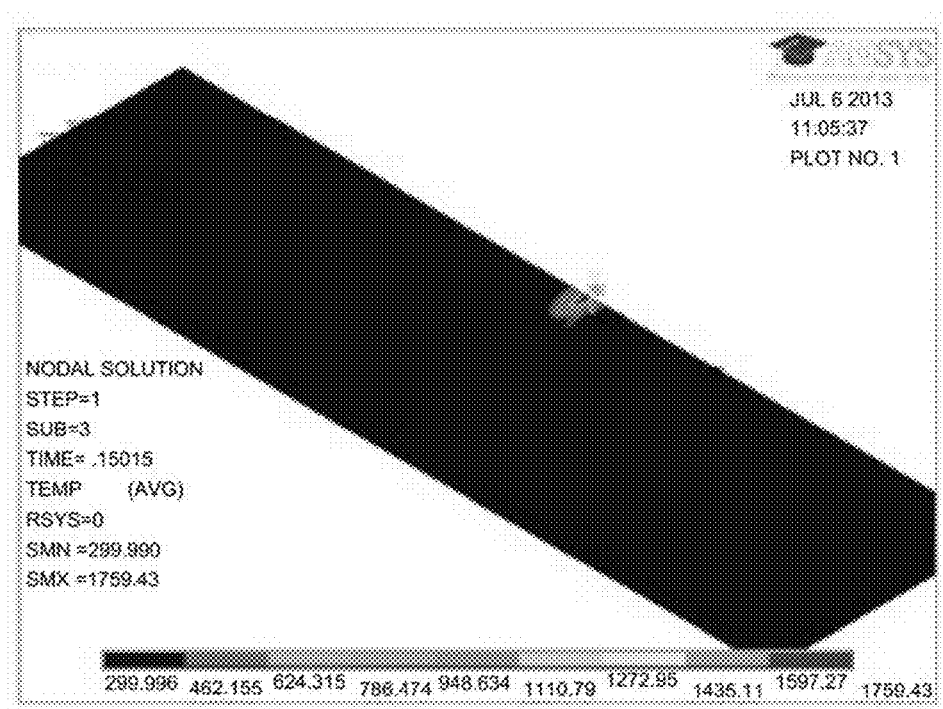
FIG. 52A, FIG. 52B, FIG. 52C, FIG. 52D, and FIG. 52E illustrate temperature fields for workpieces welded with 2000 W at 200 mm/min at different load steps.
Figure 52B:
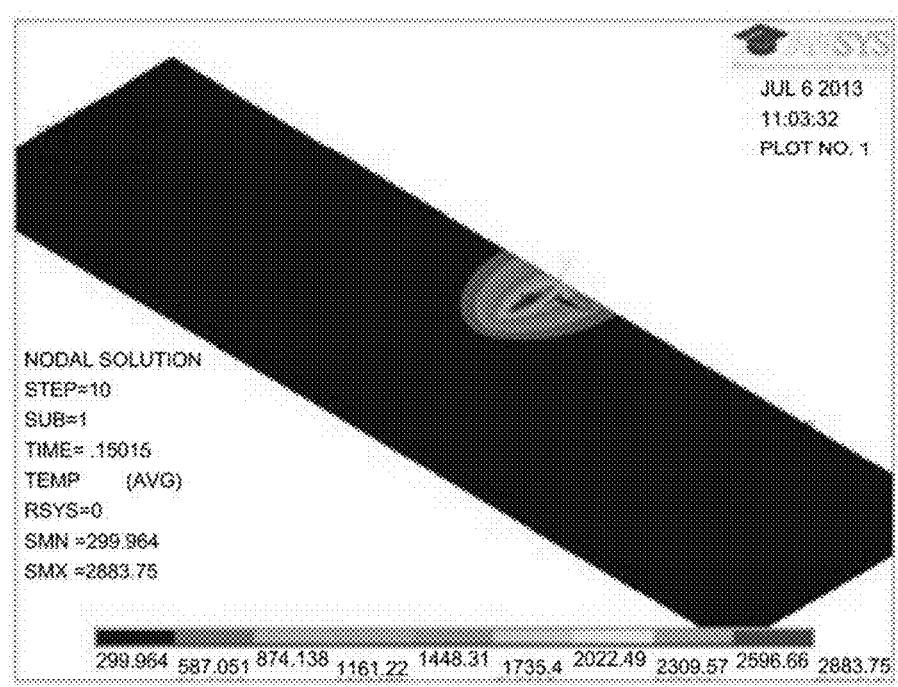
Figure 52C:
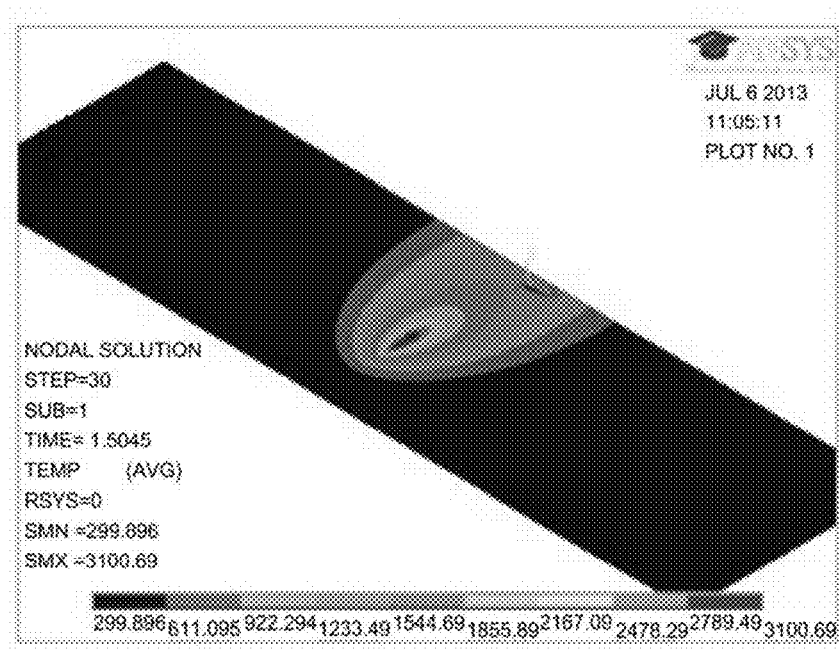
Figure 52D:
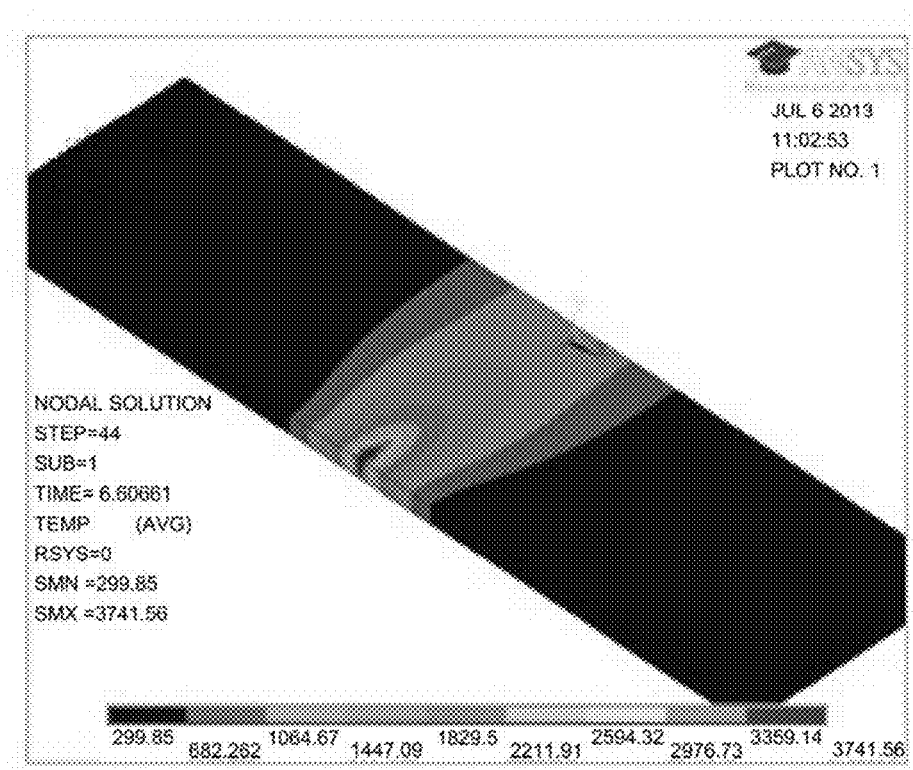
Figure 52E:
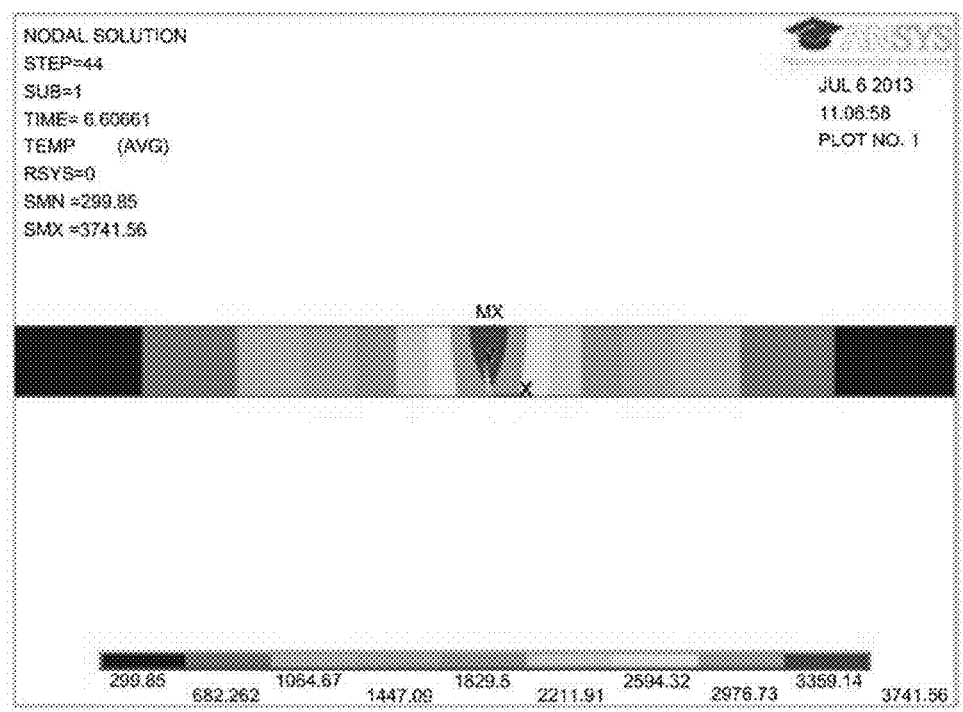

The simulation of the temperature fields during laser welding were conducted using the heat source model described in section 4.1.3. Finite Element Software ANSYS 14.0 was used to perform the simulation. Heat flux was applied on element faces to simulate the moving heat source; this was achieved by using the ANSYS Parametric Design Language (APDL) module available in ANSYS software. When the current load is shifted to the next load step the previous one is deleted. FIG. 51 shows the flowchart of the APDL module. The simulations were conducted with four different workpiece thicknesses while varying the beam power and welding speeds for each model. Three different beam powers and four welding speeds were considered during the simulation process. FIG. 52A-E shows the temperature field on the workpiece at four different load steps during the welding process for one of the welding conditions: 2000 W beam power and 200 mm/min welding speed. It is observed that there is high temperature field along the welding direction and it also shows the cooling of the workpiece away from the heat source.

Figure 53A:
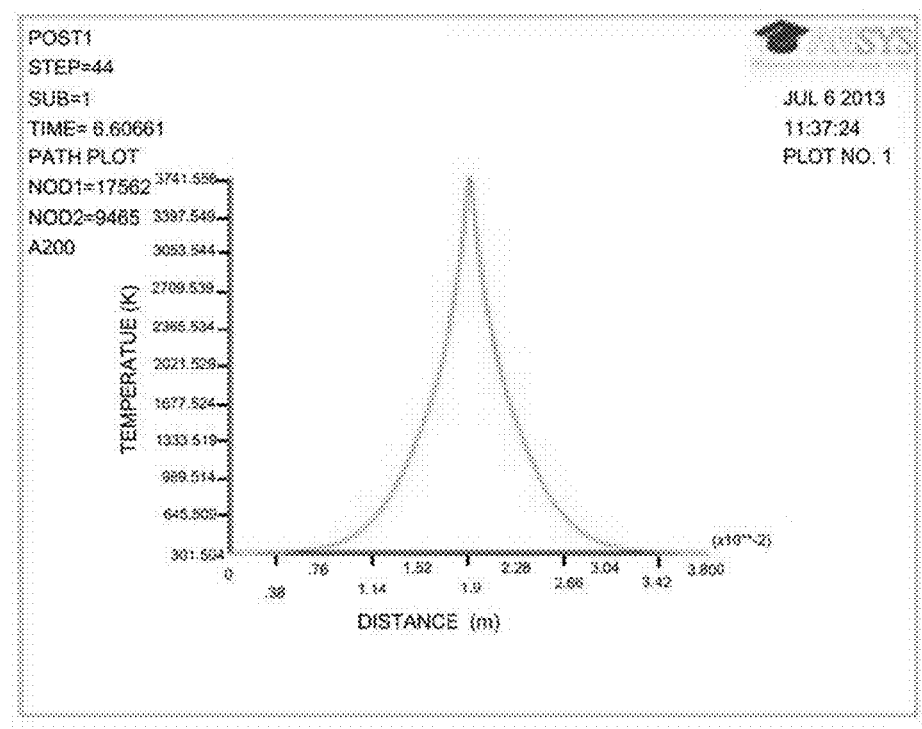
FIG. 53A is a graph of temperature profiles across weld line (radial direction).
Figure 53B:
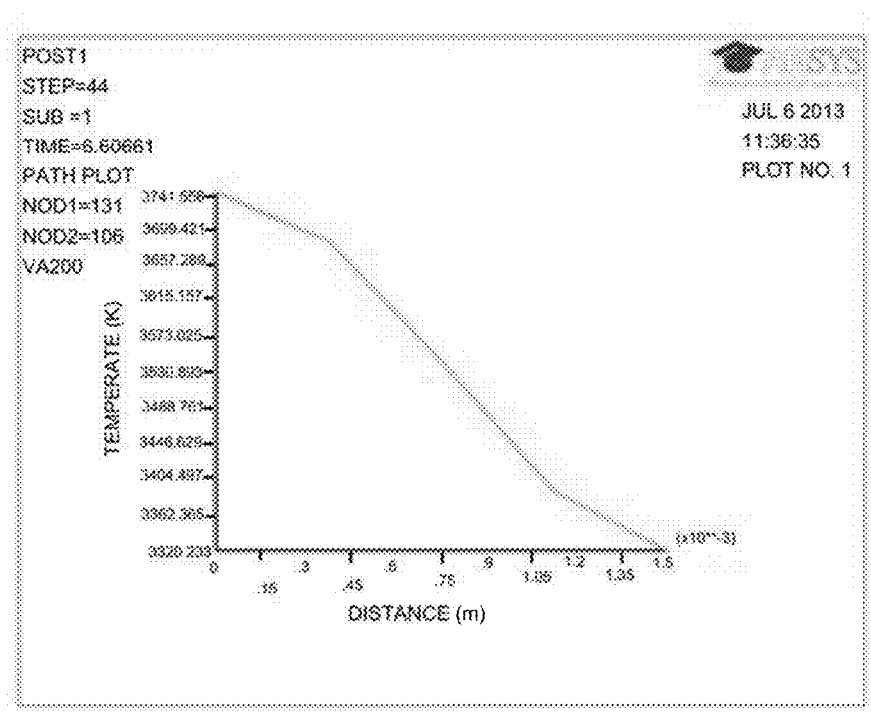
FIG. 53B is a graph of temperature profiles along the thickness (depth), for beam power 2000 W at 200 mm/min welding speed.

Temperature gradients during laser welding are usually very large, this is due to the high beam power density and the localized heating nature of laser beam. FIG. 53A-B shows the high temperature gradients across the weld line during the laser welding using 2000 W beam power at 200 mm/min welding speed, and along the thickness. It can be seen clearly that the temperature is symmetrically distributed across the workpiece and it decays sharply in the surface region, and as the depth below the surface increases temperature decay becomes sharp and further increase in the depth results in gradual decay of temperature. The rapid temperature decrease to ambient temperature on the surface indicates a highly localized heating zone within a range of 1.52 mm.

Figure 54:
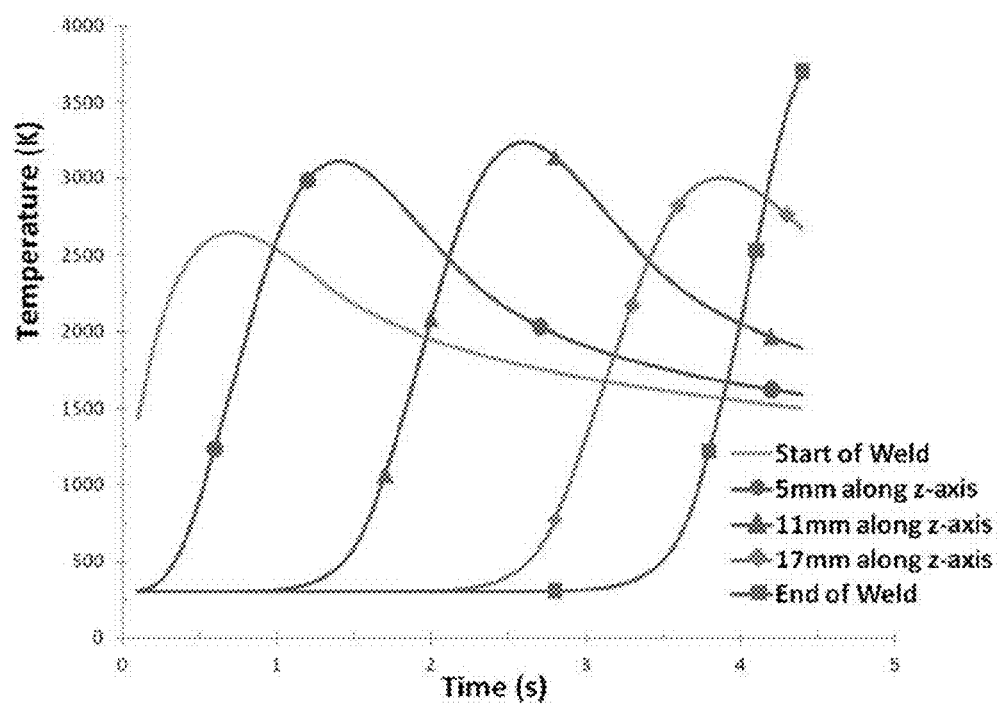
FIG. 54 is a graph of temperature histories at the weld center on the top surface for sample welded with 3000 W at 300 mm/min.
Figure 55A:
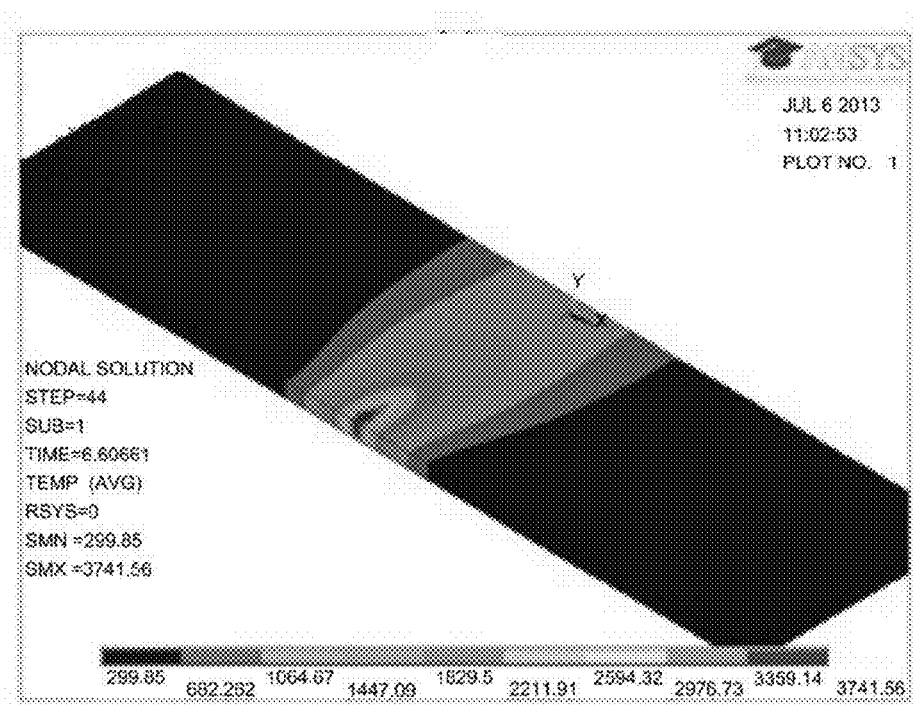
FIG. 55A is a temperature profile plot with 2000 W beam power at a welding speed of 200 mm/min.
Figure 55B:
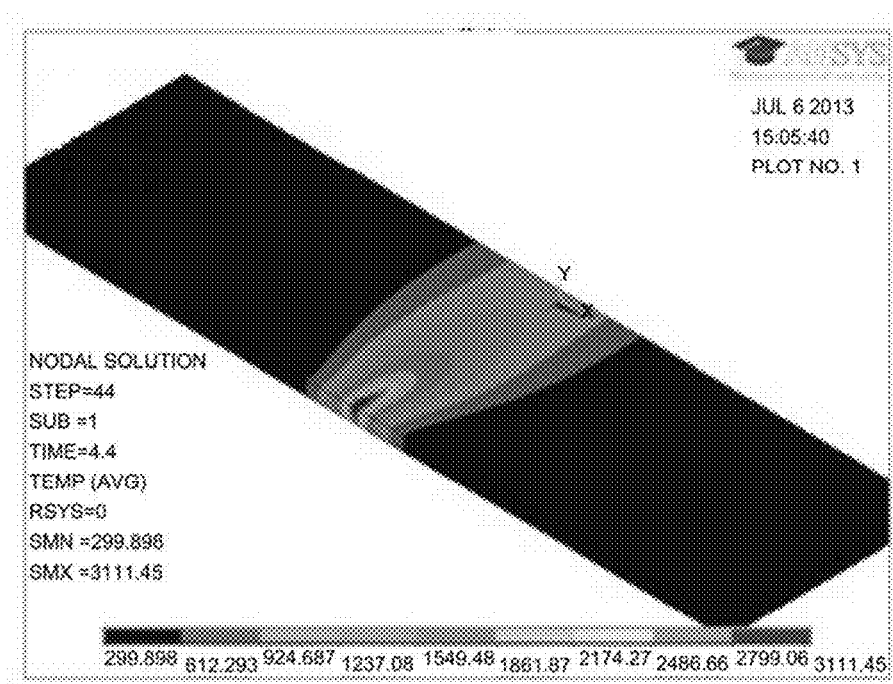
FIG. 55B is a temperature profile plot with 2000 W beam power at a welding speed of 300 mm/min.
Figure 55C:
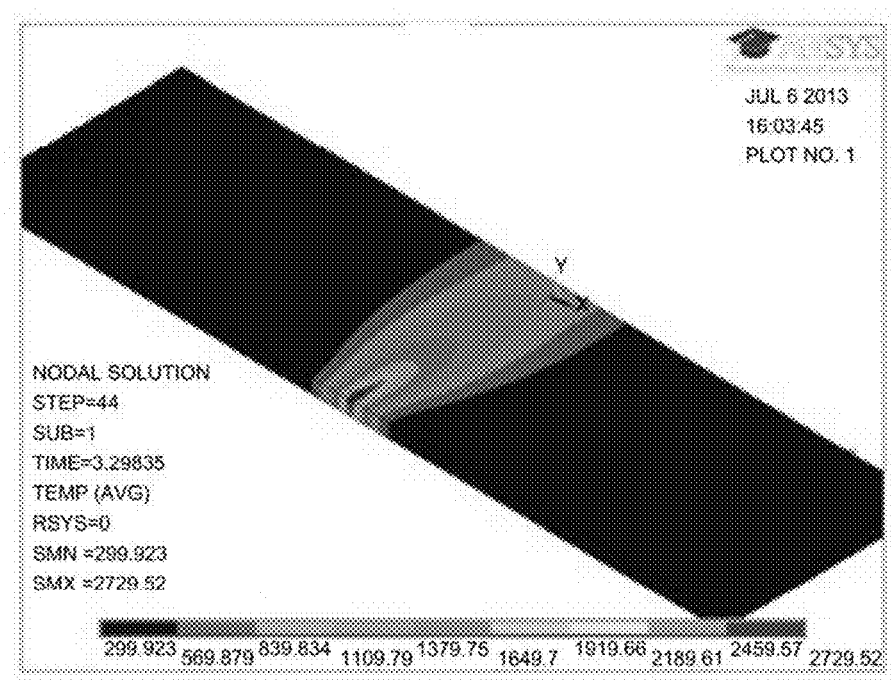
FIG. 55C is a temperature profile plot with 2000 W beam power at a welding speed of 400 mm/min.
Figure 55D:
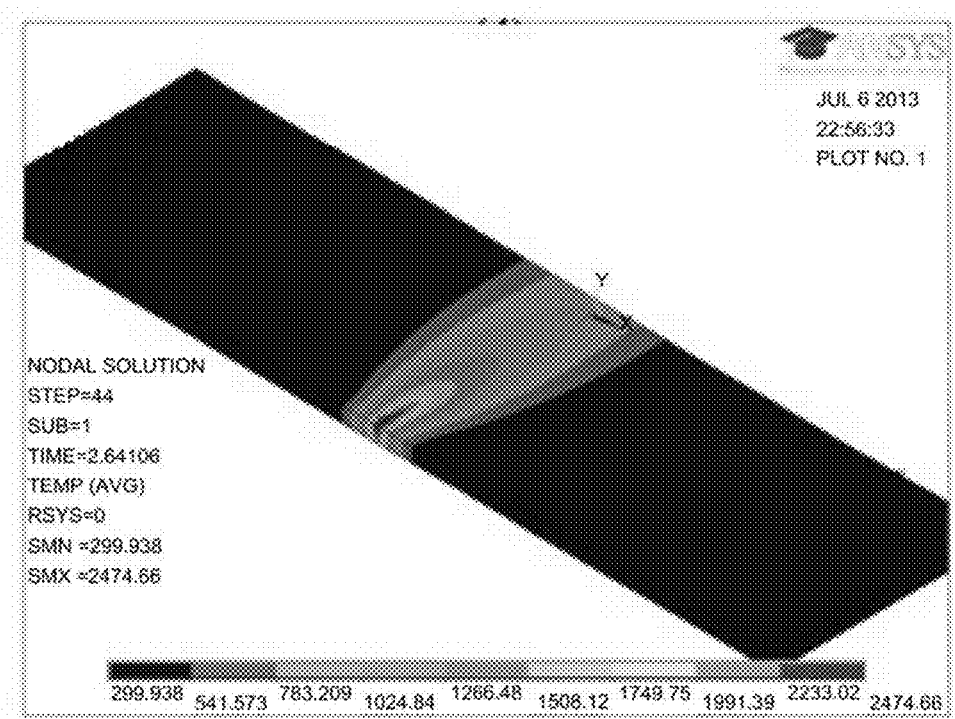
FIG. 55D is a temperature profile plot with 2000 W beam power at a welding speed of 500 mm/min.

The heat source temperature of the top element reaches a temperature much above the melting temperature of 316L ASS; which is between 1371-1400° C. "See W. Jiang, Y. Zhang, and W. Woo, "Using heat sink technology to decrease residual stress in 316L stainless steel welding joint: Finite element simulation," *International journal of pressure vessels and piping*, vol. 92, pp. 56-62, 2012 (reference); and "See Database, "MatWeb Material Property Database," http://www.matweb.com/search/DataSheet.aspx?MatGUID=9e9ab696974044cab4a7fd83687934eb&ckck=1 (reference), incorporated herein by reference in its entirety." Elements that reach a temperature above the melting temperature of the material is melted leading to the formation of molten pool which results in the formation and shape of the fusion zone. It is noticed that the shape of the molten pool is elliptical. The weld bead width was thus measured at the intercept of 1399° C. isotherm from the temperature field across the weld line plots. FIG. 54 shows the temporal variation of temperature at different position along the weld line (z-axis) during the welding process, in which it can be seen that except for the temperature histories at start/end of weld location, the other three temperature histories at 5 mm, 11 mm, and 17 mm locations along z-axis has similar profile. The temperature increased as the laser source progressed along the z-axis is attributed to the pre-heating effect experience by the material ahead of the rear molten pool. The maximum temperature on the top surface is about 3700K during the welding with 3000 W laser power at 300 mm/min welding speed.

(a) Effect of Welding Speed on the Weld Bead Width and Temperature Field

Figure 56:
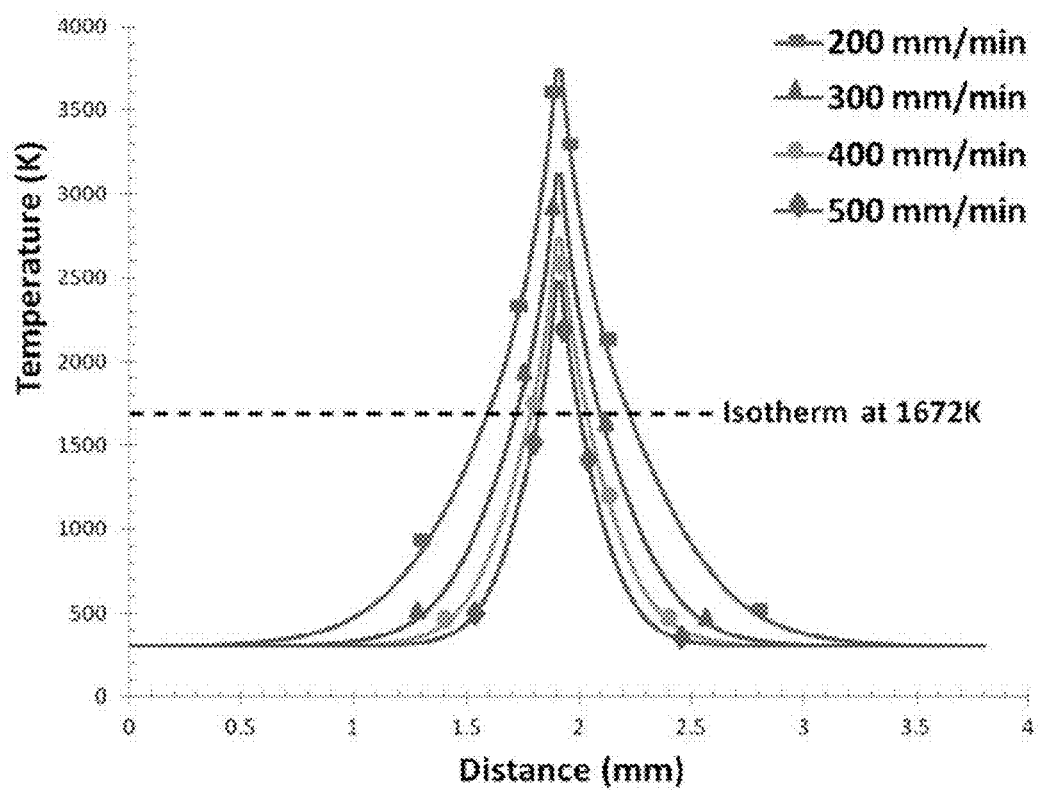
FIG. 56 is a graph of temperature profile across weld line (radial direction) with 2000 W beam power at different welding speeds.

FIG. 55A-D shows temperature profiles in the substrate material; it shows the effect of laser welding speed on temperature distribution. As the welding speed increases the narrower the temperature profile becomes. This is also illustrated in the temperature-distance plots across weld line in FIG. 56. It was found that the weld bead width is 0.82±0.01, 0.52±0.02, 0.36±0.02 and 0.27±0.01 for 200 mm/min, 300 mm/min, 400 mm/min and 500 mm/min respectively. This behavior is a result of the welding speed increase for the same amount of beam power, and the lesser exposure time of the sample to the laser beam, which consequently results in lower heat input. Therefore, the participating materials in forming the fusion zone is reduced since a small region is melted by the heat input.

(b) Effect of Laser Power on the Weld Bead Width and Temperature Field

Figure 57A:
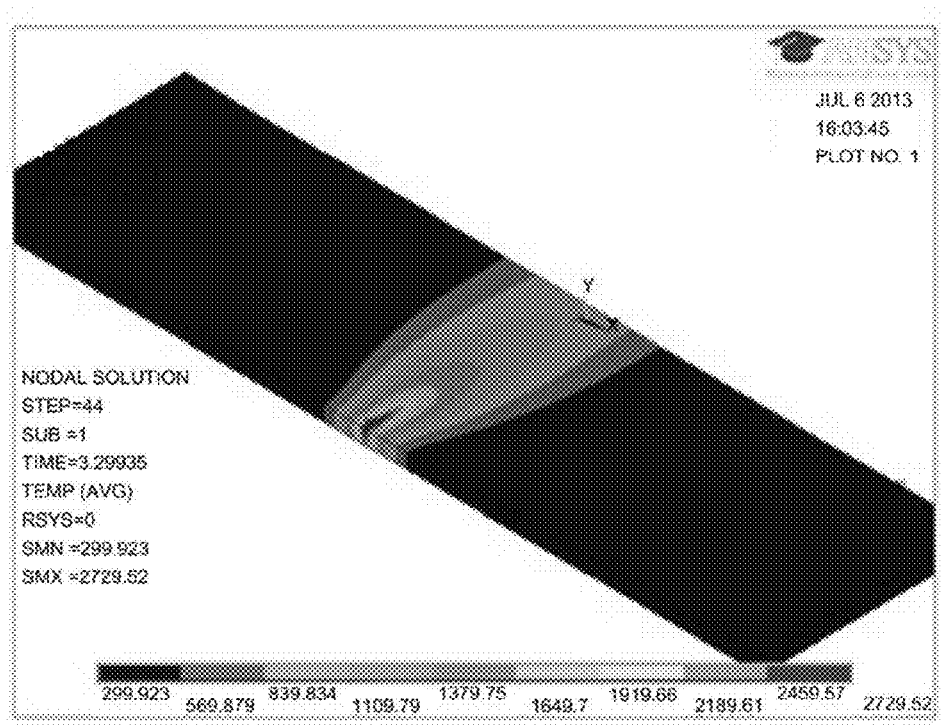
FIG. 57A is a temperature profile plot for a workpiece welded at 400 mm/min welding speed with a beam power of 2000 W.
Figure 57B:
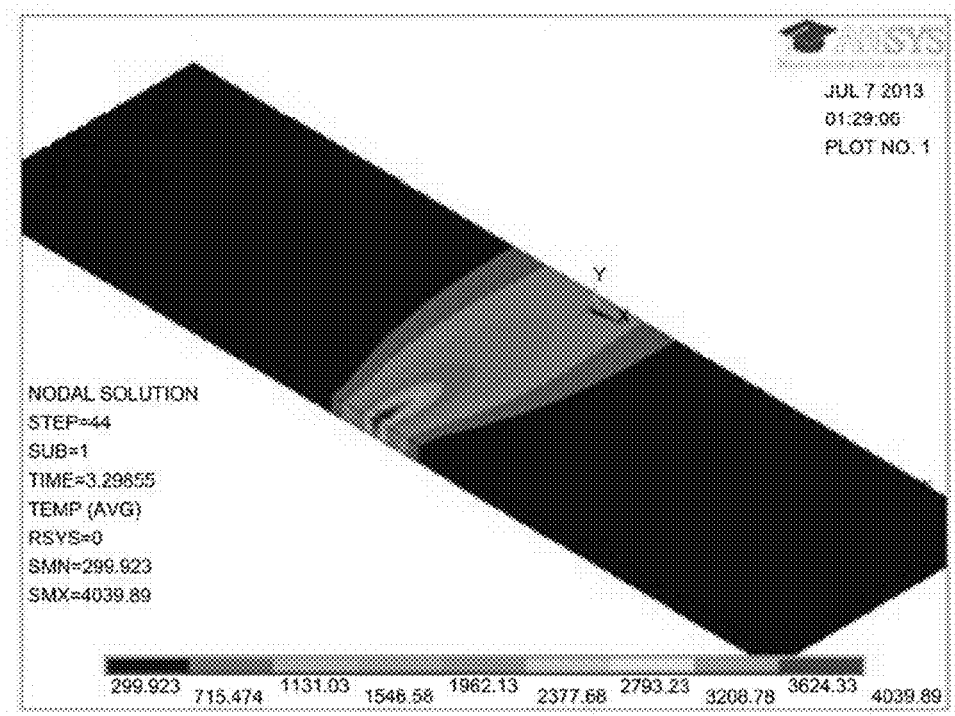
FIG. 57B is a temperature profile plot for a workpiece welded at 400 mm/min welding speed with a beam power of 3000 W.
Figure 57C:
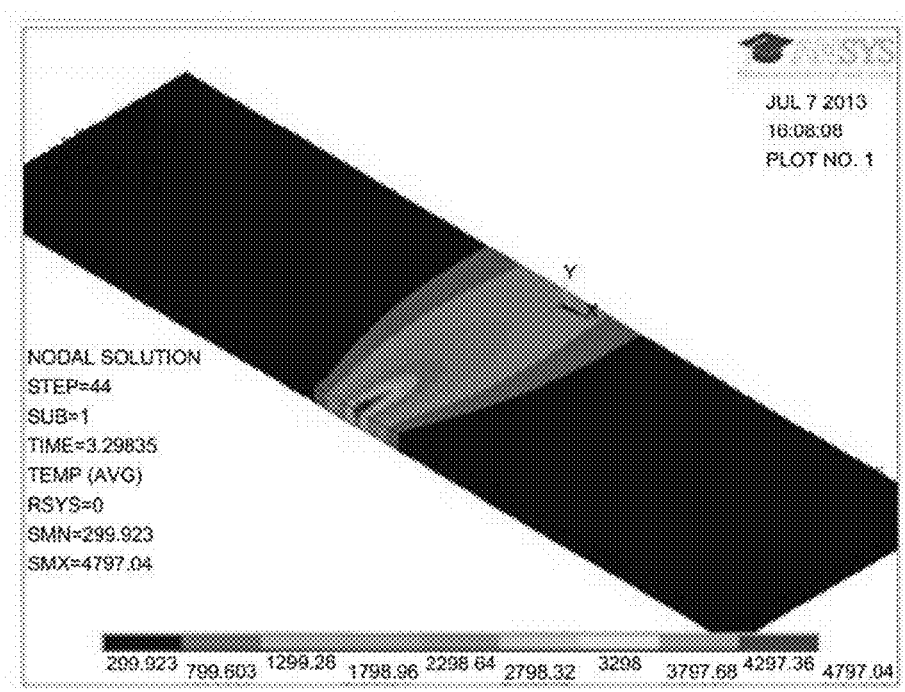
FIG. 57C is a temperature profile plot for a workpiece welded at 400 mm/min welding speed with a beam power of 4000 W.
Figure 57D:
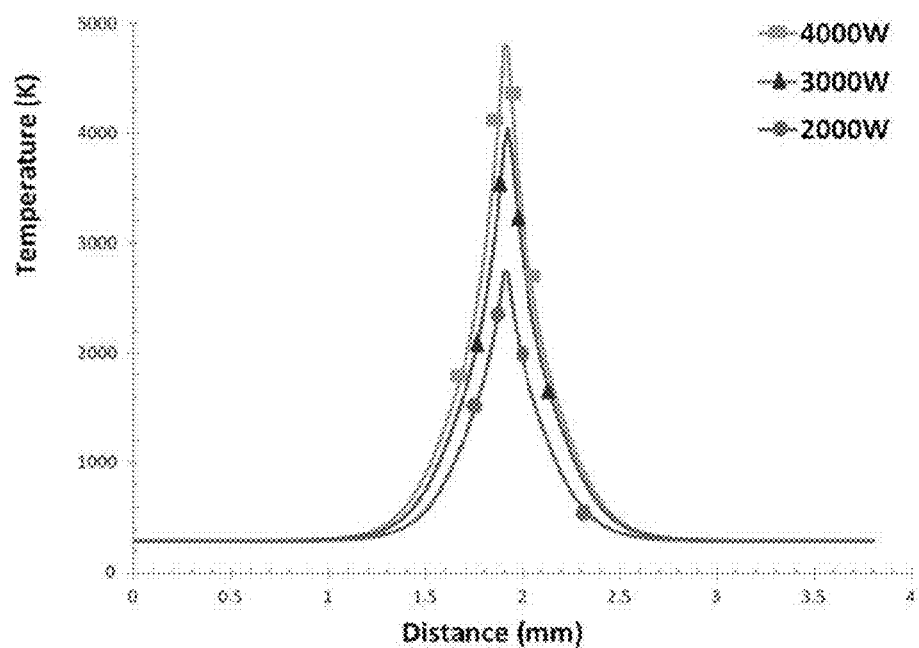
FIG. 57D is a graph of the temperature profile across weld line (radial direction) of Figures A-C.

FIG. 57A-C shows the temperature distribution for different beam power welded at 400 mm/min welding speed. The profile shows a wider temperature field as the laser beam power increases. This is so because as the beam power increased at the same welding speed, the workpiece absorbed more heat. Hence an increase in the conduction and interaction rate between the workpiece and the absorbed heat is observed. FIG. 57($d$) shows the temperature-distance plots across the weld line for the different power; the bead width from the 1399° C. isotherm were 0.77 mm±0.03, 0.54 mm±0.03 and 0.42 mm±0.03 for 4 kW, 3 kW and 2 kW beam power respectively.

(c) Effect of Sample Thickness on the Weld Bead Width and Temperature Field

Figure 58:
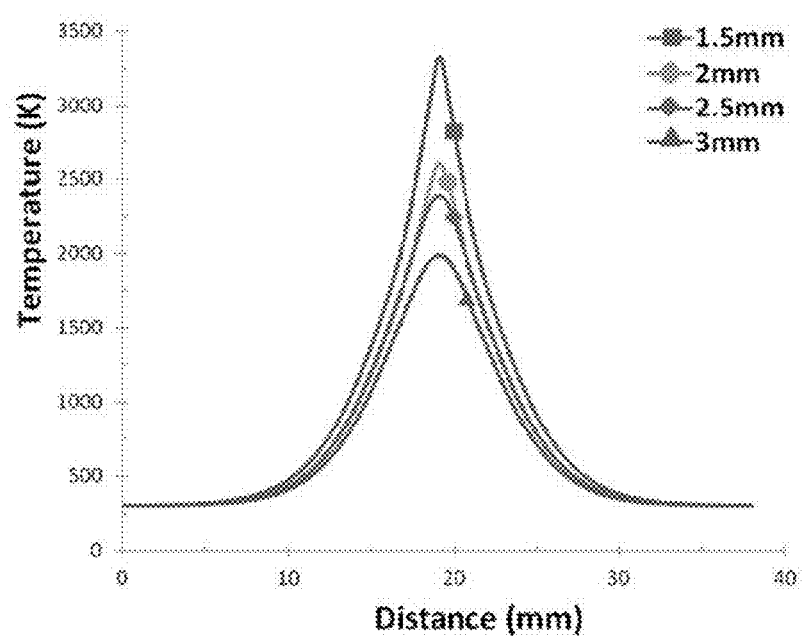
FIG. 58 is a graph of temperature Profile variation with sample thickness welded using; Laser Power=2000 W, Welding Speed=200 mm/min.

The effect of sample thickness on the temperature distribution is shown in FIG. 58. The important variation is in the lateral distribution of the heat and the maximum temperature attained for the different thickness despite being welded with same welding parameters (Laser Power=2000 W, Welding Speed=200 mm/min). This variation results due the difference in energy absorbed per volume by each sample. As sample thickness increases the energy absorbed along depth direction (y-axis) increases, this consequently reduces the lateral distribution of the heat and hence the noticed reduction in the weld bead width with sample thickness.

Comparison of Experimental and Simulation Results

Figure 59:
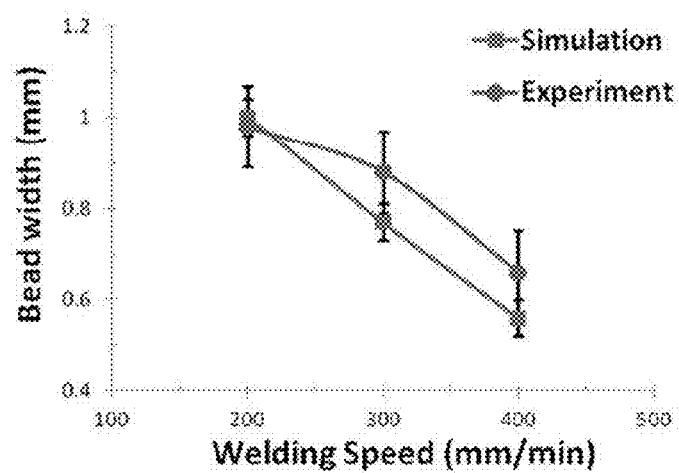
FIG. 59 is a graph of comparison of the bead widths from simulation and experimental results for different welding speed.
Figure 60:
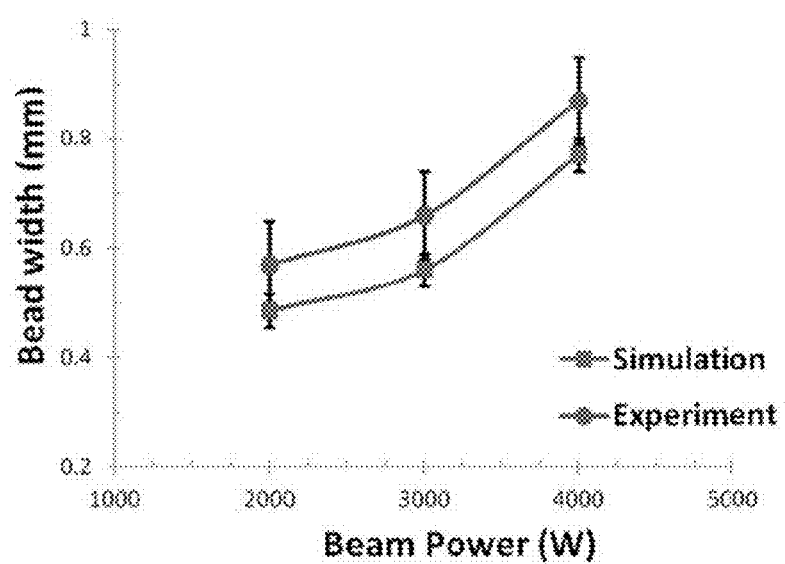
FIG. 60 is a graph of comparison of the bead widths from simulation and experimental results for different beam power.

The validation of simulation results were done by comparing the bead widths calculated from simulation and bead widths measured from the SEM micrographs. FIG. 59 and FIG. 60 show the compared results for different welding speeds and laser beam powers respectively. As clearly shown in these figures (FIGS. 59 & 60), the trends of the simulation results are in good agreement with that of the experiment with about 16% maximum percentage difference. This small discrepancy occurs because of the assumptions made in the simulations such as uniform structure, material properties considered and the irregularity of the actual weld bead width as observed from micrographs. However, the validated values are still within acceptable range.

Structural Analysis

Figure 61:
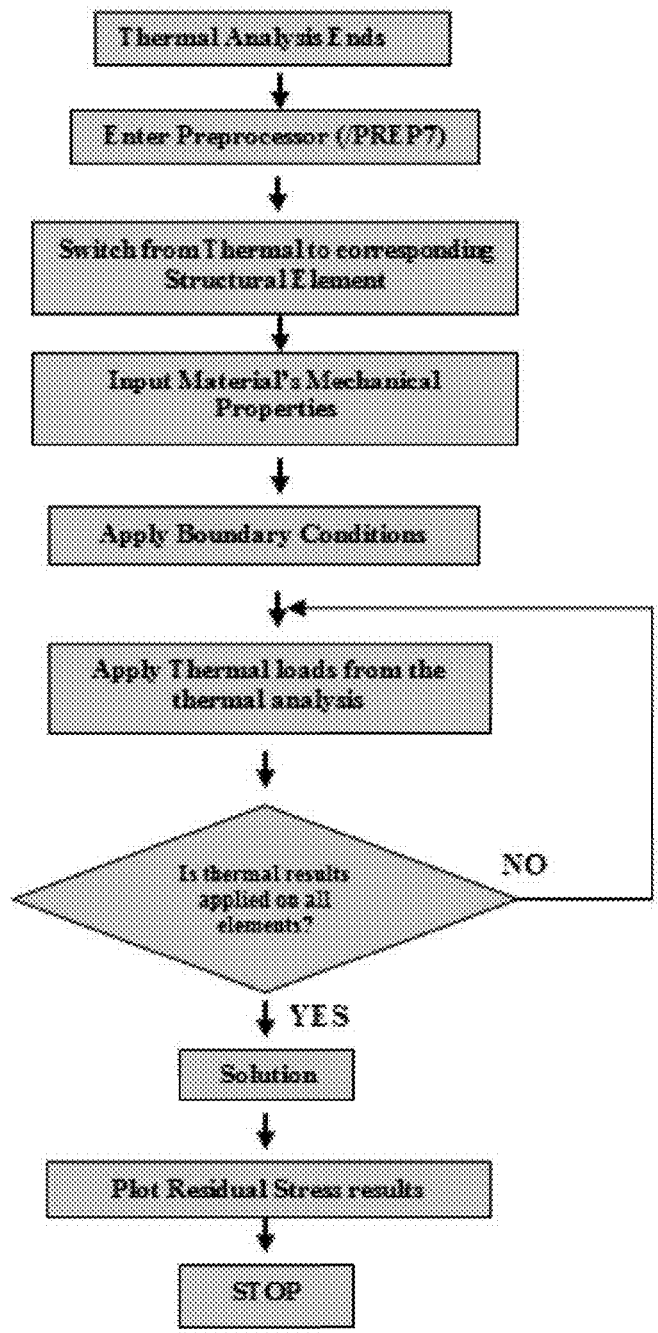
FIG. 61 is a flowchart of the Structural analysis.
Figure 62A:
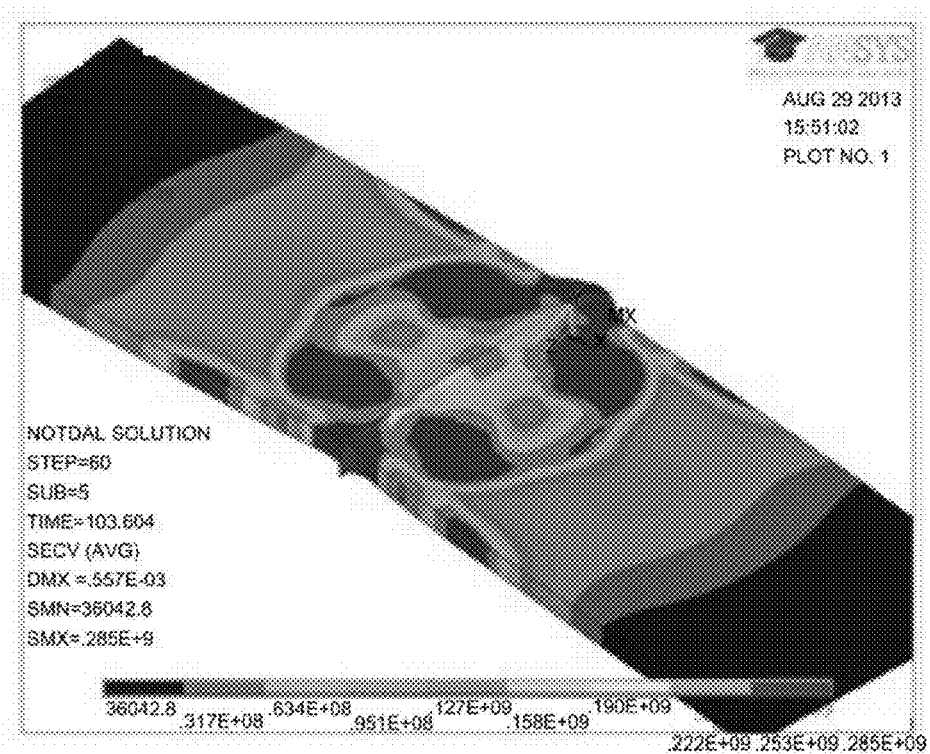
FIG. 62A is a Von Mises Stress plot for samples welded using 3000 W power at a welding speed of 200 mm/min.
Figure 62B:
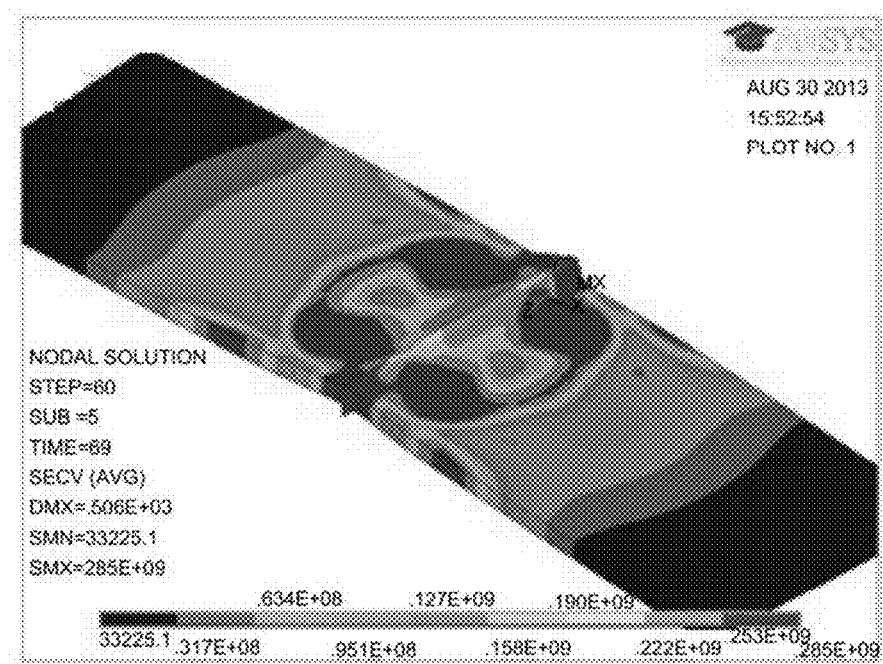
FIG. 62B is a Von Mises Stress plot for samples welded using 3000 W power at a welding speed of 300 mm/min.
Figure 62C:
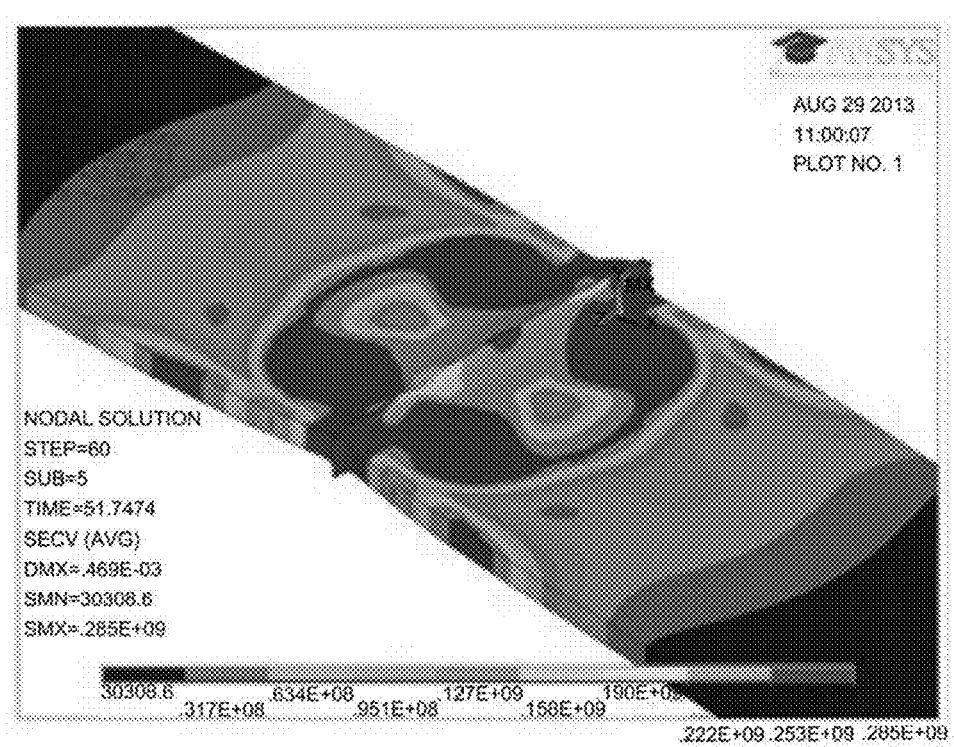
FIG. 62C is a Von Mises Stress plot for samples welded using 3000 W power at a welding speed of 400 mm/min.
Figure 62D:
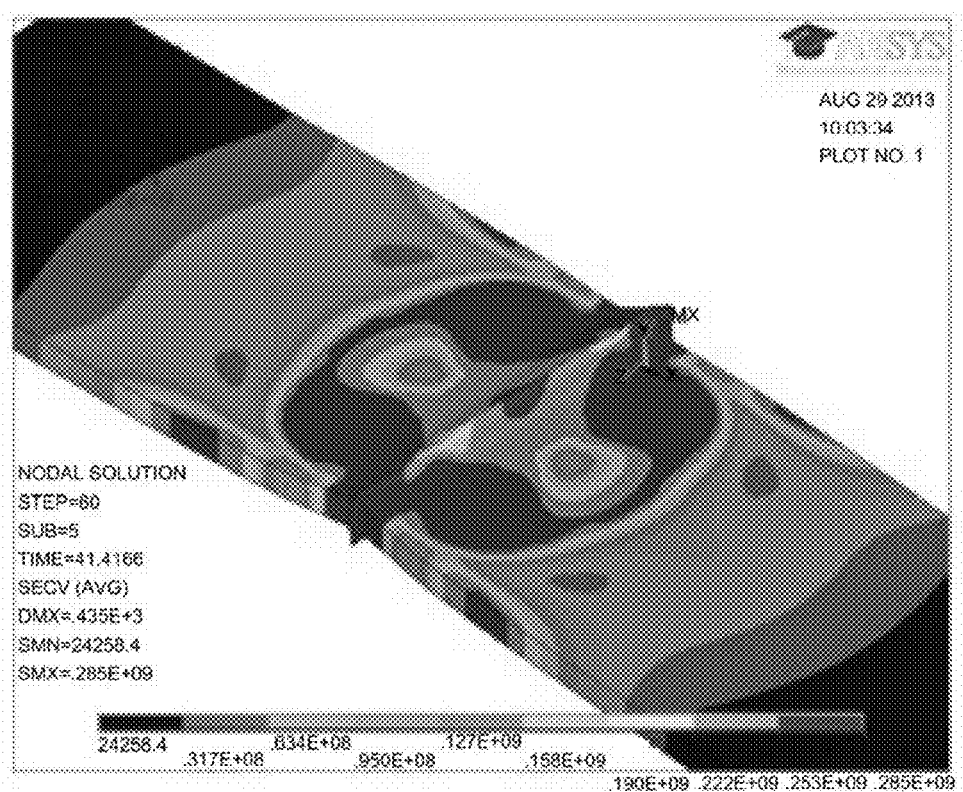
FIG. 62D is a Von Mises Stress plot for samples welded using 3000 W power at a welding speed of 500 mm/min.

A sequential-coupled analysis was adopted for the transient structural analysis during which the thermal results were inputted as body loads into the structural part. FIG. 61 is a flow chart showing the sequence of modeling of the structural part of the simulation.

Non-Linear Transient Structural Results

Figure 63:
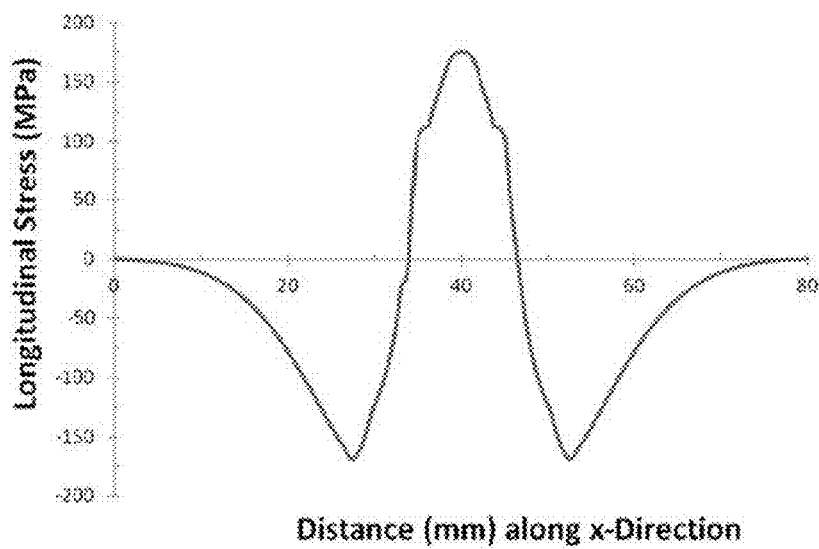
FIG. 63 is a graph of Longitudinal Stress distributions along the x-direction for sample welded with 2000 W power at 300 mm/min welding speed.
Figure 64:
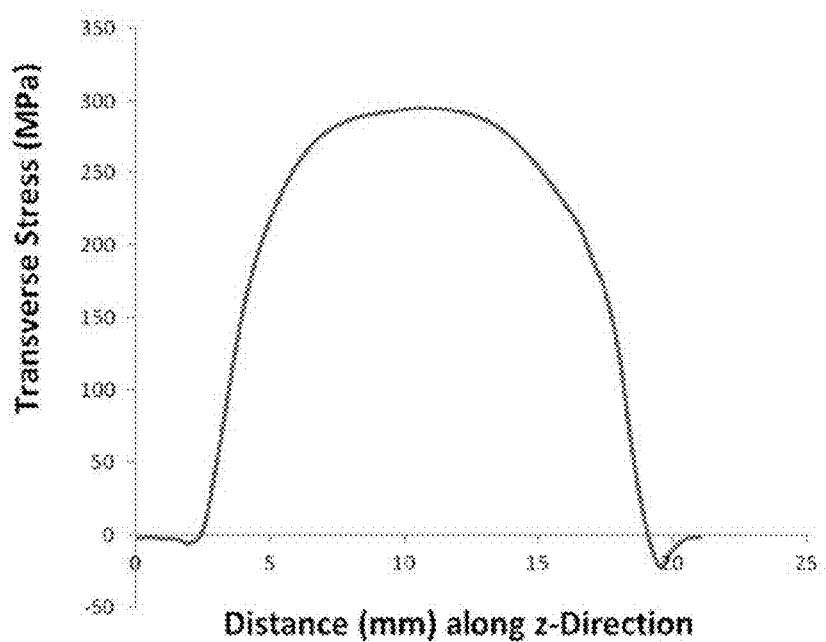
FIG. 64 is a graph of Transverse Stress distributions along the z-direction for sample welded with 2000 W power at 300 mm/min welding speed.

The Von Mises Stress plots for samples welded using 3000 W power at different welding speed is shown in FIG. 62A-D. A noticeable difference in the distribution of the stresses was observed; the area with high stresses gradually increases with the welding speed. Also observed is the longitudinal and transverse shrinkage culminating in the bulging along the centerline. FIG. 63 depicts the longitudinal stress distributions along the x-direction for sample welded with 2000 W power at 300 mm/min welding speed. High tensile stresses occur in regions near the weld due to a resistance contraction of the material as cooling commences, while compressive stresses dominate regions away from the weld line. In this case, the maximum stress value is about 180 MPa, not up to 80% of the material's yield stress. FIG. 64 shows the transverse stress field along the z-direction for sample welded with 2000 W laser power at 300 mm/min welding speed. The distributions of this stress are symmetrical along the weld line of the plate. In general, the tensile stresses occur within the fusion zone and the compressive stresses are in the bulk material. However, the magnitude of tensile stresses exceeded the compressive stresses for all samples investigated.

The Effects of Welding Parameters on Stresses

Due to the importance of stress evaluation to structures and manufacturers, the effects of welding parameters on the Von Mises stresses developed were examined.

(a) Effect of Welding Speed on the Von Mises Stress

Figure 65:
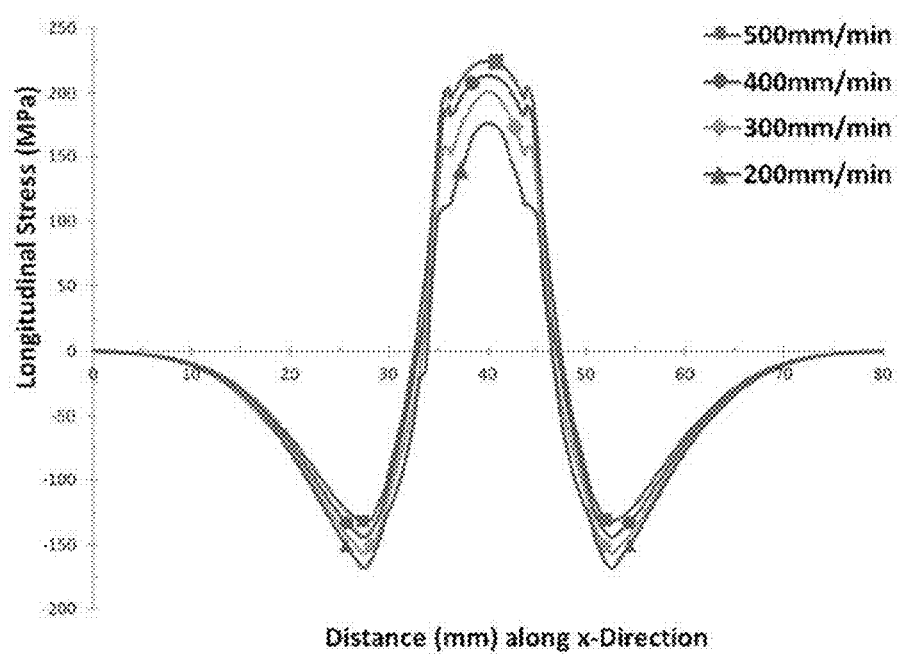
FIG. 65 is a graph of variation of Longitudinal Stresses along the x-direction with welding speed (welded with 3000 W Power).
Figure 66:
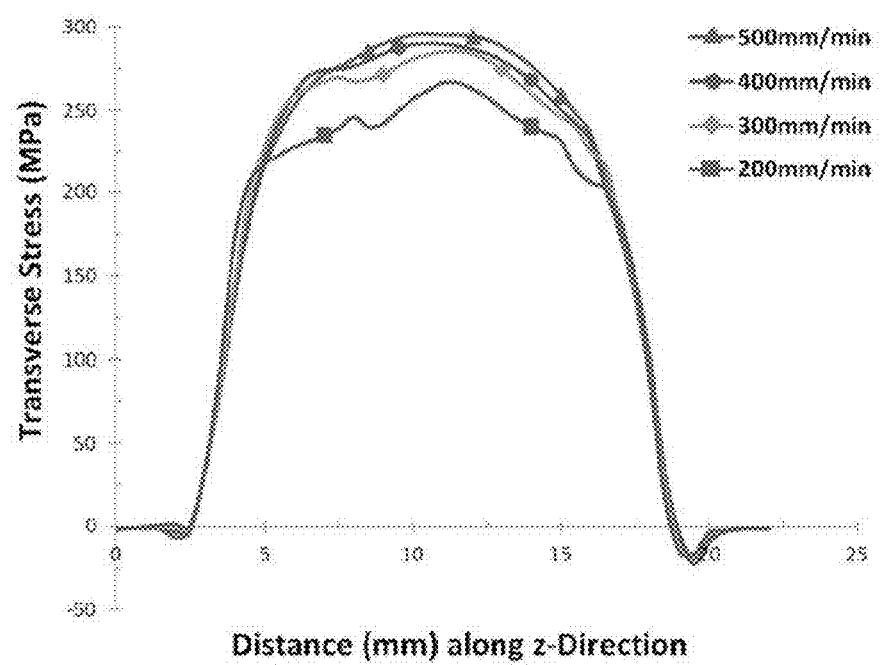
FIG. 66 is a graph of variation of Transverse Stresses along the z-direction with welding speed (welded with 3000 W Power).

FIG. 65 and FIG. 66 show the variation of longitudinal stresses along the x-direction and transverse stresses along the z-direction with welding speed respectively. It is observed that as the welding speed increased, the stresses (tensile) near the weld also increased while the stresses (compressive) in the bulk material from the area near the fusion zone gradually decreased towards both sides of the sample. This is because as the welding speed increases from 200 mm/min to 500 mm/min during welding, the heat absorption rate by the surface decreases. This consequently tends to limit the flow of material around the weld line due to the lesser dwell time of heat source; this account for the increase in the tensile stresses. In addition, the peak compressive stresses tend to rise with the welding speed. This can also be explained that since the portion that experiences material flow with increased welding speed is relatively small compare to that of lower welding speed, the stresses at the remaining portion of the workpiece could relatively be widely distributed, hence the reduction in the overall compressive stresses.

(b) Effect of Laser Power on the Von Mises Stress

Figure 67:
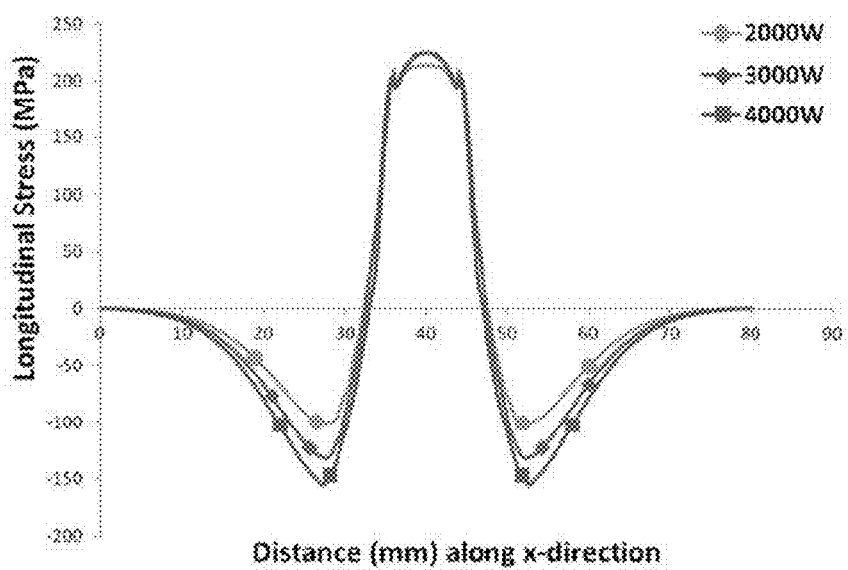
FIG. 67 is a graph of variation of Longitudinal Stresses along the x-direction with Laser Power (welding speed=500 mm/min).
Figure 68:
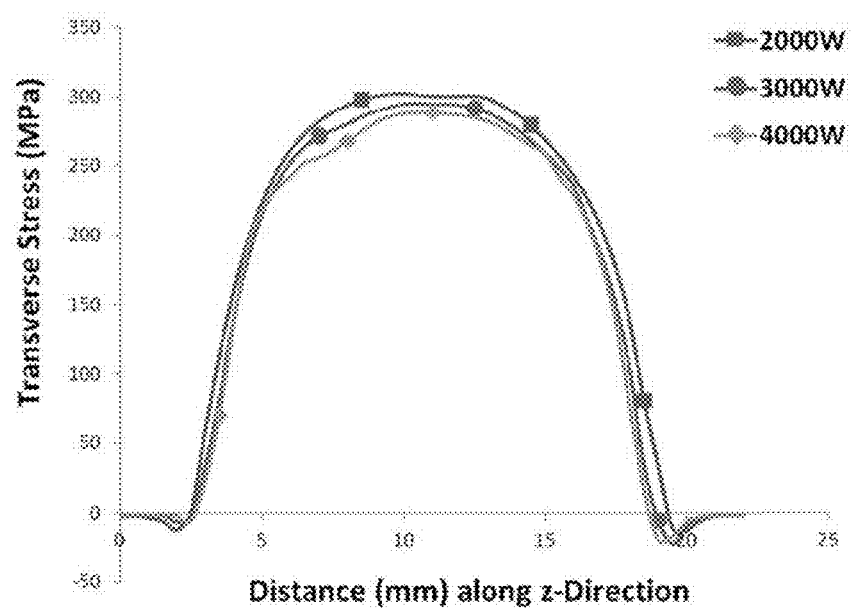
FIG. 68 is a graph of variation of Transverse Stresses along the z-direction with Laser Power (welding speed=500 mm/min).

The influence of laser power on the stresses is shown in FIG. 67 and FIG. 68 for the longitudinal and transverse stresses respectively. The stresses were plotted for 2000 W to 4000 W beam powers for similar welding speed (500 mm/min). The significant variation with the beam power is in the compressive stress which gradually increases with laser power. This behavior is due to the increase in energy dissipation at higher laser power, which results in more material flow within the welded region. Therefore, the bulk material compressive stress tends to rise relatively due to tensile effect at the molten region and peak compressive stresses are found close to the fusion boundary being the most heat affected area of the bulk material. Tensile stresses were nearly identical and symmetrical around the weld for the tested samples with same welding speed. Nevertheless, the tensile stresses exceeded the compressive stresses in all samples investigated. The transverse stress of samples welded with a welding speed of 500 mm/min approach the yield stress of the material for all laser beam power studied and the maximum Von Mises stress was about 285 MPa for all samples investigated, which is still below the material's yield strength.

Example 7

Conclusions

Modal testing and material characterization of laser welded of 316L austenitic stainless steel blanks were carried out. The natural frequency of welded samples was obtained via an experimental set-up coupled with LabView software. The morphological and metallurgical changes in the welded region were examined using the optical microscopy and the SEM. Microhardness distribution across the fusion zone was measured. The sequential-coupled thermo-mechanical analysis was modeled using the finite element method (FEM). The FEM Software Ansys APDL was used to execute the simulations.

It was found that the difference between the natural frequencies of the "as received" and welded samples reached a maximum of about 12%. The modification of the elastic modulus at the welded region and the subsequent effect on the moment of inertia of the system during the laser welding process are responsible for the new natural frequencies. The parametric study revealed that higher beam power favors the natural frequency due to grain coarsening accompanying increased heat dissipation on the workpiece. Also, a direct relationship was also observed for the sample thickness which is associated with an increase in the moment of inertia. Increasing the welding speed was found to vary inversely with the natural frequency, but further increases caused an insignificant attenuation of the energy plasma resulting in high heat input, hence, the natural frequency increased. Natural frequencies of the welded samples are correspondingly similar to that of the "as received" samples for all samples investigated, this confirms the absence of defects and voids within the welded region. The analysis of the experimental results indicated that sample thickness is the most influential parameters that affect the natural frequency.

The post-weld microstructural examination was conducted and the influence of the welding parameters was considered. It is observed that at high laser beam power, evaporation of the sample material occurred in the irradiated surface. This caused the formation of a cavity as the laser power intensity further increased, and similar observation was true at a lesser welding speed. This situation resulted from the excessive laser heating and recoil developed in between the vapor front and the liquid layer. From the optical microscope and SEM microstructure observation, a grain coarsening was evident in the HAZ while highly directional fine grains existed in the fusion zone. Moreover, it was found that dendritic and cellular structures are formed in the weld fusion zone. In addition, detailed examination of welded region revealed that the fusion zone was free from cracks, defects and voids. Increasing laser beam power and welding speed was found to cause grain coarsening and grain refining, respectively. The sample thickness also influenced the heat distribution, microstructural development and the weld bead width.

The observed enlargement of the weld bead width at the top of the welding section is a result of the intermittent variation in the laser power intensity and welding speed at the onset of the welding process. Despite this, no cracks or voids were noticed across this section of the weld. Solidification resulted in the formation of bainite at the fusion zone with noticeable cementite due to concentration of carbon in this region. While near the neighborhood of the fusion zone, dendritic microstructures were observed due to the relatively higher cooling rate than that in the fusion zone. The mechanical properties of laser welded butt joints of austenitic steel AISI 316L banks were higher than the properties of the base material.

The temperature distribution and Stress field developed in the welding zone was modeled using the finite element method (FEM) ANSYS software. A double ellipsoidal heat source model was used to model the moving heat source. The temperature profile revealed a high temperature gradient across the fusion zone. The weld bead width was determined from the isotherm of the liquids temperature of bulk material. The simulated weld bead width agrees well with the measured width from the SEM micrographs. Moreover, once the laser beam scans over the welded region the temperature decays sharply. This caused a sharp increase in von Mises stress due to the attainment of high temperature gradient in this region. In general, tensile stresses occurred within the fusion zone and compressive stresses are in the bulk material. However, the magnitude of tensile stresses exceeds the compressive stresses for all samples investigated. The compressive stresses in the bulk material gradually decreased from the peak values (close to the fusion boundary) to the minimum at both ends of the welded samples. The Von Mises stress of welded samples with a welding speed of 500 mm/min approach the yield stress of the material for different laser beam power studied, and it's maximum value was about 285 MPa for all samples investigated, which is still below the material's yield strength.

The invention claimed is:

1. A process for determining the quality of a laser weld-seam, comprising:
   subjecting a welded plate comprising the laser weld-seam and a geometrically equivalent non-welded plate to a physical impact to generate a natural vibration frequency;
   measuring the natural vibration frequency of the welded plate and, separately; measuring the natural vibration frequency of the non-welded plate, with an accelerometer;
   comparing the natural vibration frequency of the welded plate to the natural vibration frequency obtained from the geometrically equivalent non-welded plate;
   determining a uniformity of the laser weld-seam by the similarity between the natural vibration frequency of the welded plate and the geometrically equivalent non-welded plate; and
   based on the determined uniformity of the laser weld-seam, welding a second plate with at least one welding parameter that differs from welding parameters used to weld the welded plate when the laser weld-seam is determined to be non-uniform.

2. The process of claim 1, wherein the welded and non-welded plate comprise a low-carbon steel, and the process is non-destructive.

3. The process of claim 2, wherein the low-carbon steel is 316L austenitic stainless steel.

4. The process of claim 1, wherein the welded plate and a geometrically equivalent non-welded plate are oriented in a cantilever beam configuration with a fixed end, and the physical impact is imparted on the plates at a distance ranging from greater than x to less than L, wherein x is a distance of the weld from the fixed end, and L is a total length of the plate from the fixed end.

5. The process of claim 4, wherein, during the subjecting and measuring, the accelerometer is disposed on a top side of the welded plate and, separately, a top side of the non-welded plate, in the cantilever beam configuration.

6. The process of claim 5, wherein the physical impact is imparted to the top side of the welded plate and the non-welded plate.

7. The process of claim 1, further comprising comparing the natural vibration frequency of the welded plate to a theoretical fundamental natural frequency of the geometrically equivalent non-welded plate obtained through mathematical analysis to validate the process.

8. The process of claim 7, wherein the theoretical fundamental natural frequency ($\omega_{nf1}$) is calculated by the formula $$\omega_{nf1} = \sqrt{\frac{K}{M_1}}$$

wherein K is the stiffness and $M_1 = m_{c1} + m_{ac}$, where $m_{c1}$ is the effective mass at the tip of the plate, and $m_{ac}$ is the mass of the accelerometer at the free end of the plate.

9. The process of claim 7, wherein the process is validated when the natural vibration frequency of the welded plate does not differ by more than 10% from the theoretical fundamental natural frequency of the non-welded plate with plate thickness ranging from 1.5-3.0 mm.

10. The process of claim 1, wherein the laser-weld seam is considered non-uniform when the % difference between the natural vibration frequency of the welded plate and the geometrically equivalent non-welded plate is greater than 13%, in the frequency range between 70-260 Hz.

11. The process of claim 1, wherein the welded plate and the non-welded plate have a thickness ranging from 1.5-3.0 mm and a natural vibration frequency of 100-300 Hz.

12. The process of claim 1, wherein the welded plate is obtained with a welding speed of 200-400 mm/min and has a natural vibration frequency of 100-140 Hz.

13. The process of claim 1, wherein the welded plate is obtained with a laser beam power of 2-4 KW and has a natural vibration frequency of 90-140 Hz.

14. The process of claim 1, wherein the physical impact is generated by an impact hammer.

15. The process of claim 1, wherein the second plate is welded with a welding speed and/or a laser beam power that differs from the welding speed and/or laser beam power used to weld the welded plate.

16. The process of claim 1, wherein the second plate is welded with a welding speed that differs from the welding speed used to weld the welded plate.

17. The process of claim 1, wherein the second plate is welded with a laser beam power that differs from the laser beam power used to weld the welded plate.

18. The process of claim 1, wherein the laser weld-seam of the welded plate forms a butt-joint.

* * * * *